US009434993B2

(12) United States Patent
Binder et al.

(10) Patent No.: US 9,434,993 B2
(45) Date of Patent: Sep. 6, 2016

(54) SYSTEMS FOR IDENTIFYING COSMETIC AGENTS FOR SKIN CARE COMPOSITIONS

(71) Applicant: The Procter & Gamble Company, Cincinnati, OH (US)

(72) Inventors: Robert Lloyd Binder, Montgomery, OH (US); Robert Scott Youngquist, Mason, OH (US); Jun Xu, Cincinnati, OH (US); Kenton Duane Juhlin, Milford, OH (US); Rosemarie Osborne, Cincinnati, OH (US); Scott Michael Hartman, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/749,717

(22) Filed: Jun. 25, 2015

(65) Prior Publication Data

US 2015/0292017 A1    Oct. 15, 2015

Related U.S. Application Data

(62) Division of application No. 13/402,102, filed on Feb. 22, 2012, now abandoned.

(60) Provisional application No. 61/445,315, filed on Feb. 22, 2011.

(51) Int. Cl.
*C40B 60/12* (2006.01)
*C12Q 1/68* (2006.01)
(Continued)

(52) U.S. Cl.
CPC ............. *C12Q 1/6883* (2013.01); *G06F 19/18* (2013.01); *G06F 19/20* (2013.01); *G06F 19/28* (2013.01); *C12Q 2600/148* (2013.01); *C12Q 2600/158* (2013.01)

(58) Field of Classification Search
CPC .............................. C07K 16/18; G06F 19/18
See application file for complete search history.

(56) References Cited

U.S. PATENT DOCUMENTS 2,694,668 A   11/1954   Fricke
2,809,971 A   10/1957   Bernstein
(Continued)

FOREIGN PATENT DOCUMENTS

EP    2019316      1/2009
GB    849433 A     9/1960
(Continued)

OTHER PUBLICATIONS

"Genomics of Skin Aging: Practical Applications", Journal of Drugs in Dermatology Supplement, vol. 8, Issue 7 (2009).
(Continued)

*Primary Examiner* — Jyoti Nagpaul
(74) *Attorney, Agent, or Firm* — John G. Powell

(57) ABSTRACT

A system for identifying connections between a cosmetic agent and at least one gene associated with a skin aging condition. The system includes a computer readable medium having stored thereon a plurality of instances and a skin aging gene expression signature. Each instance comprises an ordered list of identifiers representing a plurality of differentially expressed genes generated as a result of contact between the cosmetic agent and a human fibroblast cell or a human keratinocyte cell. The computing device includes computer-readable instructions for accessing the plurality of instances and the skin aging gene expression signature stored on the computer readable medium, comparing each of the instances to the skin aging gene expression signature, and assigning a connectivity score to each of the instances based on the comparison.

17 Claims, 9 Drawing Sheets

(51) Int. Cl.
    *G06F 19/18*       (2011.01)
    *G06F 19/20*       (2011.01)
    *G06F 19/28*       (2011.01)

(56)                References Cited

U.S. PATENT DOCUMENTS

| | | |
|---|---|---|
| 2,826,551 A | 3/1958 | Geen |
| 3,152,046 A | 10/1964 | Kapral |
| 3,236,733 A | 2/1966 | Karsten |
| 3,753,196 A | 8/1973 | Kurtz |
| 3,755,560 A | 8/1973 | Dickert |
| 3,761,418 A | 9/1973 | Parran |
| 3,964,500 A | 6/1976 | Drakoff |
| 4,323,683 A | 4/1982 | Bolich, Jr. |
| 4,345,080 A | 8/1982 | Bolich, Jr. |
| 4,364,837 A | 12/1982 | Pader |
| 4,379,753 A | 4/1983 | Bolich, Jr. |
| 4,421,769 A | 12/1983 | Dixon |
| 4,470,982 A | 9/1984 | Winkler |
| 4,677,120 A | 6/1987 | Parish et al. |
| 4,741,855 A | 5/1988 | Grote |
| 4,885,107 A | 12/1989 | Wetzel |
| 4,885,311 A | 12/1989 | Parish et al. |
| 5,049,584 A | 9/1991 | Purcell et al. |
| 5,104,646 A | 4/1992 | Bolich, Jr. |
| 5,106,609 A | 4/1992 | Bolich, Jr. |
| 5,124,356 A | 6/1992 | Purcell et al. |
| RE34,075 E | 9/1992 | Purcell et al. |
| RE34,584 E | 4/1994 | Grote |
| 5,624,666 A | 4/1997 | Coffindaffer |
| D391,162 S | 2/1998 | Kokenge |
| 6,451,300 B1 | 9/2002 | Dunlop |
| 6,974,569 B2 | 12/2005 | Dunlop |
| 7,001,594 B1 | 2/2006 | Peffly |
| D516,436 S | 3/2006 | Campbell |
| 7,101,889 B2 | 9/2006 | Kaczvinsky |
| D535,191 S | 1/2007 | Corker |
| D542,660 S | 5/2007 | Thomas |
| D547,193 S | 7/2007 | Blasko |
| D547,661 S | 7/2007 | Blasko |
| D558,591 S | 1/2008 | Blasko |
| D563,221 S | 3/2008 | Ashiwa |
| D570,707 S | 6/2008 | Blasko |
| 7,531,497 B2 | 5/2009 | Midha |
| 7,585,827 B2 | 9/2009 | Geary |
| 7,654,420 B2 | 2/2010 | Honda |
| 7,704,932 B2 | 4/2010 | Evans |
| 7,709,015 B2 | 5/2010 | Masuda |
| 7,727,516 B2 | 6/2010 | Botchkareva |
| 7,772,214 B2 | 8/2010 | Vatter |
| 8,324,447 B2 | 12/2012 | Goldstein |
| 2002/0012927 A1 | 1/2002 | Burmer |
| 2002/0169562 A1 | 11/2002 | Stephanopoulos |
| 2003/0170739 A1 | 9/2003 | Iobst |
| 2003/0223951 A1 | 12/2003 | Geary |
| 2007/0040306 A1 | 2/2007 | Morel |
| 2007/0205226 A1 | 9/2007 | Honda et al. |
| 2009/0017080 A1 | 1/2009 | Tanner |
| 2009/0064349 A1 | 3/2009 | Goldstein |
| 2009/0110709 A1 | 4/2009 | Mitts |
| 2009/0220488 A1* | 9/2009 | Gardner .......... C07K 16/18 514/1.1 |
| 2009/0298113 A1 | 12/2009 | Vielhaber |
| 2011/0150798 A1 | 6/2011 | Bacus |
| 2011/0269852 A1 | 11/2011 | McDaniel |
| 2012/0283112 A1 | 11/2012 | Binder |
| 2013/0337087 A1 | 12/2013 | Finlay et al. |

FOREIGN PATENT DOCUMENTS

| | | |
|---|---|---|
| JP | 2003245097 | 9/2003 |
| JP | 2008245558 | 10/2008 |
| JP | 2010172240 A | 8/2010 |
| JP | 2011019414 A | 2/2011 |
| WO | 02090934 | 11/2002 |
| WO | WO 03/100557 | 12/2003 |
| WO | WO 2005/040416 | 5/2005 |
| WO | 2011087523 | 1/2011 |
| WO | 2012011904 A1 | 1/2012 |
| WO | 2012116081 A2 | 8/2012 |
| WO | WO2013192076 | 12/2013 |
| WO | WO 2014/028572 | 2/2014 |

OTHER PUBLICATIONS

Bissett el al. "Niacinamide: A B Vitamin that Improves Aging Facial Skin Appearance" American Society for Dermatologic Surgery Inc., Dermatol Surg 2005; 31:860-865.

Draelos "Clinical Situations Conducive to Proactive Skin Health and Anti-Aging Improvement", The Society for Investigative Dermatology 2008, pp. 25-27.

In Vitro Biomarker Responses to a New Anti-Aging Peptide, PAL-KT, Osborne et al, American Academy of Dermatology 67th Annual Meeting Media Resources, 2009.

Skin Biomarkers Confirm the Anti-Oxidant Activity of Olive Derivatives and Yeast Ferment Filtrate, Finlay et al., P&G 67th Annual Meeting of American Academy of Dermatology (2009).

Jensen, et al. "Acid and neutral sphingomyelinase, cermide synthase, and acid ceramidase activities in cutaneous aging" Experimental Dermatology 2005p. 609-616.

Pels, et al. "Clobetasol Propionate—Where, When, Why?", Drugs of Today 2008, 44(7): 547-557.

Tjabringa, G et al. "Development and Validation of Human Psoriatic Skin Equivalents"; The American Journal of Pathology, vol. 173, No. 3, Sep. 2008, 9 pps.

Arsic, I, et al. "Preparation of Novel Apigenin-Enriched, Liposomal and Non-Liposomal, Antiinflammatory Topical Formulations as Substitutes for Corticosteroid Therapy" Phytotherapy Research, 25: 228-233 (2011), 6 pps.

Hegyi, A. et al. "Vitamin D Analog Calcipotriol Suppresses the Th17 Cytokine-Induced Proinflammatory S100 "Alarmins" Psoriasin (S100A7) and Koebnerisin *S100A15 in Psoriasis" Journal of Investigative Dermatology 2012, vol. 132, 9 pages.

International Search Report; PCT/US2013/055138, Mailing Date Nov. 12, 2013; 15 pages.

Millikin, Cheri et al. "Topical N-acetyl glucosamine and niacinamide affect pigmentation relevant gene expression in in vitro geonomics experimentation" Journal American Acadamy of Dermatology, Feb. 2007.

Bissett, Donald, et al. "Genomic Expression Changes Induced by Topical N-acetyl Glucosamine in Skin Equivalent Cultures in Vitro" Journal of Cosmetic Dermatology.

Yumiko, I., et al. "Identification of Novel Hair-Growth Inducers by means of Connectivity Mapping", FASEB Journal, vol. 24, May 2010.

Hughes, T.R. et al. "Functional discovery via a compendium of expression profiles" Cell vol. 102, 109-126 (2000).

Jagetia G. C. et al, "Genotoxic Effect of Hydroquinone on the Cultured Mouse Spleenocytes" Toxicology Letter 121(1):15-20, 2001.

Lamb, Justin, et al. "Connectivity Map: Gene Expression Signatures to Connect Small Molecules, Genes, and Disease", Science, vol. 313, 2006.

M. Hollander et al. "Nonparametric Statistical Methods"; Wiley, New York, ed. 2, 1999 see, e.g., pp. 178-185.

Raynaud E. et al., "Depigmentation for cosmetic purposes: prevalence and side-effects in a female population in Senegal" Ann Dermatol Venereol 128(6-7):720-724, 2001 (abstract).

Shimizu K. et al., "The skin-lightening effects of artocarpin on UVB-induced pigmentation" Planta Med 68(1):79-81, 2002.

Sivapirabu, G. et al., "Topical Nicotinamide Modulates Cellular Energy Metabolism and Provides Broad-Spectrum Protection Against Ultraviolet Radiation-Induced Immunosuppression in Humans", British Journal of Dermatology 2009.

Subramanian,, A. et al, Gene set enrichment analysis: A knowledge-based approach for interpreting genome-wide expression profiles. (2005) Proc.Natl.Acad Sci U.S.A, 102, 15545-15550.

(56) References Cited

OTHER PUBLICATIONS

International Search Report; PCT/US2013/034055; Mailing Date Jun. 11, 2013; 17 pages.
International Search Report PCT/US2013/034052; Mailing Date Jun. 11, 2013; 18 pages.
International Search Report PCT/US2013/034054; Mailing Date Jun. 13, 2013; 18 pages.
International Search Report PCT/US2013/034055; Mailing Date Jun. 11, 2013; 17 pages.
International Search Report PCT/US2013/034117; Mailing Date Jun. 11, 2013; 17 pages.
Johnson, "Skin conditions and related need for medical care amount persons 1-74 years, United States, 1971-1974." Vital and Health Statistics, Series 11, No. 212, DHEW publication No. (PHS) 79-1660, U.S. Department of Health, Education and Welfare, National Center for Health Statistics 1978: 1-72.
Smith et al.,"The effect of a high-protein, low glycemic-load diet versus a conventional, high glycemic-load diet on biochemical parameters associated with acne vulgaris: A randomized, investigator-masked, controlled trial" Journal of the American Academy of Dermatology vol. 57 (2): 247-56 (2007).
Kluken et al., "Atopic eczema/dermatitis syndrome—a genetically complex disease. New advances in discovering the genetic contribution" Allergy, 58(1):5-12 (2003).
Cork et al., "Epidermal barrier dysfunction in atopic dermatitis" J Invest Dermatol., 129(8):1892-908 (2009).
Kimata et al., "Enhancement of Allergic Skin Wheal Responses by Microwave Radiation from Mobile Phones in Patients with Atopic Eczema/Dermatitis Syndrome" Int Arch of Allergy and Immunology, 129 (4):348-350 (2002).
Wang et al., "Environmental risk factors for early infantile atopic dermatitis" Pediatr Allergy Immunol., 18(5):441-7 (2007).
Hughes, Timothy et al. "Functional discovery via a compendium of expression profiles" Cell vol. 102, 2000, pp. 109-126.
Lamb, Justin, et al. "Connectivity Map: Gene Expression Signatures to Connect Small Molecules, Genes, and Disease," Science, vol. 313, 2006; 8 pages.
Bier et al., "DNA Microarrays" Adv. Biochem. Eng. Biotechnol., 109:433-53 (2008).
Hoheisel, "Microarray Technology: Beyond Transcript Profiling and Genotype Analysis" Nat. Rev. Genet., 7:200-10 (2006).
Fan et al., "Illumina universal bead arrays" Methods Enzymol., 410:57-73 (2006).
Raqoussis & Elvidger, "Affymetrix GeneChip system: moving from research to the Clinic" Expert Rev. Mol. Diagn., 6:145-52 (2006).
Mockler et al., "Applications of DNA tiling arrays for whole-genome analysis" Genomics, 85:1-15 (2005).
Hollander, M. et al. "Nonparametric Statistical Methods"; Wiley, New York, ed. 2, 1999 pp. 178-185.
Trivedi, N. et al., "Gene array expression profiling in acne lesions reveals marked upregulation of genes involved in inflammation and matrix remodeling," J Invest Dermatol;126(5):1071-9 (2006).
Plager, D. et al. "Early cutaneous gene transcription changes in adult atopic dermatitis and potential clinical implications," Exp Dermatol;16(1):28-36 (2007).
Olsson, M. et al. "Increased expression of aquaporin 3 in atopic eczema," Allergy; 61(9):1132-7.

Mobini, R. et al. "A module-based analytical strategy to identify novel disease-associated genes shows an inhibitory role for interleukin 7 Receptor in allergic inflammation," BMC Syst Biol; 3:19 (2009).
Nair et al., "Genome-wide scan reveals association of psoriasis with IL-23 and NF-kappaB pathways," Nat Genet; 41(2):199-204(2009).
Swindell et al., "Genome-wide expression profiling of five mouse models identifies similarities and differences with human psoriasis," PLoS One; 6(4); Apr. 2011; 20 pages.
Lamb et al. "Gene Set Enrichment Analysis: A Knowledge Based Approach for Interpreting Genome-wide Expression profiles", Proc. Natl.Acad Sci U.S.A, 102, 15545-15550.
Nair et al., "Genome-wide scan reveals association of psoriasis with IL-23 and N-kappaB pathways," Nat Genet; 41(2):199-204(2009).
Fisher, G.J. "Pathophysiology of Premature Skin Aging Induced by Ultraviolet Light" The New England Journal of Medicine; vol. 337 No. 20; Nov. 13, 1997; 10 pages.
Zouboulis, C.C. et al. "Clinical Aspects and Molecular Diagnostics of Skin Aging" Clinics in Dermatology (2011)29, 12 pages.
Choi, H. et al. "Labisia Pumila Extract Protects Skin Cells From Photoaging Caused by UVB Irradiation" Journal of Bioscience and Bioengineering, vol. 109, No. 3. 2010; 6 pages.
Gilcrest, B.A. "Ageing and Photoageing of the Skin: Observations at the Cellular and Molecular Level" British Journal of Dermatology (1992) 127, Supplement 41; 6 pages.
Lamb, J. "The Connnectivity Map" A New Tool for Biomedical Research Nature Reviews Cancer, vol. 7, Jan. 2007; 8 pages.
Lamore, S.D. et al. "The Topical Antimicrobial Zinc Pyrithione is a Heat Shock Response Indicator that causes DNA damage and PARP-dependent evergy Crisis in Human Skin Cells" Cell Stress and Chaperones (2010) 15: 309-322.
Magalhaes, J. P. "Ageing Research in the post-genome era: New technologies for an old problem" Redox Metabolism and Longevity Relationships in Animal and Plants, vol. 62, Feb. 16, 2009, pp. 99-115.
International Search Report PCT/US2012/026145; Mailing Date Apr. 5, 2013; 8 pages.
PCT International Preliminary Report; PCT/US2012/02614; Mailing Date Feb. 22, 2011; 13 pages.
International Search Report PCT/US2013/055138; Mailing Date Nov. 12, 2013; 15 pages.
Mills, K.J. "Dandruff/seborrhoeic dermatitis is characterized by an inflammatory genomic signature and possible immune dysfunction" Transcriptional Analysis of the condition and treatment effects of zinc pyrithione 2012 British Association of Dermatologists 166 (Suppl 2), pp. 33-40.
Mihaly, J. "Decreased retinoid concentration and retinoid signaling pathways in human atopic dermatitis" 2011 John Wiley & Sons, Experimental Dermatology, 20, pp. 326-330.
Ding-Dar, L. "Retinoid-Responsive Trascriptional Changes in Epidermal Keratinocytes" J. Cellular Physiology 220: pp. 427-329; 2009.
Guttman-Yassky E., et al., "Major differences in inflammatory dendritic cells and their products distinguish atopic dermatitis from psoriasis", J. Allergy Clin. Immunol., vol. 119, No. 5, pp. 1210-1217, May, 2007, USA.

\* cited by examiner

SYSTEMS FOR IDENTIFYING COSMETIC AGENTS FOR SKIN CARE COMPOSITIONS

FIELD

The present application is generally directed to a system for identifying cosmetic agents for use in skin care compositions. More specifically, the present application discloses a system for identifying connections between a cosmetic agent and at least one gene associated with a skin aging condition and incorporating the cosmetic agent into a skin care composition.

BACKGROUND

Connectivity mapping is a well-known hypothesis generating and testing tool having successful application in the fields of operations research, computer networking and telecommunications. The undertaking and completion of the Human Genome Project, and the parallel development of very high throughput high-density DNA microarray technologies enabling rapid and simultaneous quantization of cellular mRNA expression levels, resulted in the generation of an enormous genetic database. At the same time, the search for new pharmaceutical actives via in silico methods such as molecular modeling and docking studies stimulated the generation of vast libraries of potential small molecule actives. The amount of information linking disease to genetic profile, genetic profile to drugs, and disease to drugs grew exponentially, and application of connectivity mapping as a hypothesis testing tool in the medicinal sciences ripened.

The general notion that functionality could be accurately determined for previously uncharacterized genes, and that potential targets of drug agents could be identified by mapping connections in a data base of gene expression profiles for drug-treated cells, was spearheaded in 2000 with publication of a seminal paper by T. R. Hughes et al. ["Functional discovery via a compendium of expression profiles" Cell 102, 109-126 (2000)], followed shortly thereafter with the launch of The Connectivity Map (-map Project by Justin Lamb and researchers at MIT ("Connectivity Map: Gene Expression Signatures to Connect Small Molecules, Genes, and Disease", Science, Vol 313, 2006.) In 2006, Lamb's group began publishing a detailed synopsis of the mechanics of C-map construction and installments of the reference collection of gene expression profiles used to create the first generation C-map and the initiation of an ongoing large scale community C-map project, which is available under the "supporting materials" hyperlink at http://www.sciencemag.org/content/313/5795/1929/suppl/DC1.

The basic paradigm of predicting novel relationships between disease, disease phenotype, and drugs employed to modify the disease phenotype, by comparison to known relationships has been practiced for centuries as an intuitive science by medical clinicians. Modern connectivity mapping, with its rigorous mathematical underpinnings and aided by modern computational power, has resulted in confirmed medical successes with identification of new agents for the treatment of various diseases including cancer. Nonetheless, certain limiting presumptions challenge application of C-map with respect to diseases of polygenic origin or syndromic conditions characterized by diverse and often apparently unrelated cellular phenotypic manifestations. According to Lamb, the challenge to constructing a useful C-map is in the selection of input reference data which permit generation of clinically salient and useful output upon query. For the drug-related C-map of Lamb, strong associations comprise the reference associations, and strong associations are the desired output identified as hits.

Noting the benefit of high-throughput, high density profiling platforms which permit automated amplification, labeling hybridization and scanning of 96 samples in parallel a day, Lamb nonetheless cautioned: "[e]ven this much firepower is insufficient to enable the analysis of every one of the estimated 200 different cell types exposed to every known perturbagen at every possible concentration for every possible duration . . . compromises are therefore required" (page 54, column 3, last paragraph). Hence, Lamb confined his C-map to data from a very small number of established cell lines. This leads to heightened potential for in vitro to in vivo mismatch, and limits information to the context of a particular cell line. Selection of cell line, therefore, may be critical to the utility of a resulting C-map.

Lamb stresses that particular difficulty is encountered if reference connections are extremely sensitive and at the same time difficult to detect (weak), and Lamb adopted compromises aimed at minimizing numerous, diffuse associations. Since the regulatory scheme for drug products requires high degrees of specificity between a purported drug agent and disease state, and modulation of disease by impacting a single protein with a minimum of tangential associations is desired in development of pharmaceutical actives, the Lamb C-map is well-suited for screening for potential pharmaceutical agents despite the Lamb compromises.

The connectivity mapping protocols of Lamb would not be predicted, therefore, to have utility for hypothesis testing/generating in the field of cosmetics. Cosmetic formulators seek agents or compositions of agents capable of modulating multiple targets and having effects across complex phenotypes and conditions. Further, the phenotypic impact of a cosmetic agent must be relatively low by definition, so that the agent avoids being subject to the regulatory scheme for pharmaceutical actives. Nonetheless, the impact must be perceptible to the consumer and preferably empirically confirmable by scientific methods. Gene transcription/expression profiles for cosmetic conditions are generally diffuse, comprising many genes with low to moderate fold differentials. Cosmetic agents, therefore, provide more diverse and less acute effects on cellular phenotype and generate the sort of associations expressly taught by Lamb as unsuitable for generating connectivity maps useful for confident hypothesis testing.

Contrary to the teachings of Lamb and the prior art in general, the present inventors surprisingly discovered that useful connectivity maps could be developed from cosmetic active—cellular phenotype—gene expression data associations in particular with respect to skin care cosmetics. Specifically, certain aspects of the present invention are based on the surprising discovery that selection of human dermal fibroblast cells as the relevant cell line resulted in construction of connectivity maps useful for hypothesis generating and testing relating to cosmetic agents in treatment of photo-damaged/photo-aged skin, while a combination of fibroblast and keratinocyte cells appeared most suitable for intrinsically aged skin. Skin is a highly complex system, and the effects of aging conditions, whether intrinsic or photo-induced, on skin are diffuse and not fully understood. Therefore, it could not be predicted that a fibroblast cell or a keratinocyte cell, or any combination thereof, could be used to construct a connectivity map effective for generating and testing hypotheses relating to cosmetic actives and genes associated with skin aging.

Skin is a complex, multi-layered and dynamic system that provides a protective covering defining the interactive boundary between an organism and the environment. It is the largest organ of the body and is vitally important to both our health and our self image. As shown in FIG. 1, skin comprises three principal layers, the epidermis, the dermis, and a layer of subcutaneous fat. The majority of cells in the epidermis are keratinocytes that produce a family of proteins called keratins. Keratins contribute to the strength of the epidermis. The epidermis itself may be divided into multiple layers with the outermost layer referred to as the stratum corneum, and the innermost layer referred to as the basal layer. All epidermal cells originate from the basal layer and undergo a process known as differentiation as they gradually displace outward to the stratum corneum, where they fuse into squamous sheets and are eventually shed. In healthy, normal skin, the rate of production equals the rate of shedding (desquamation).

The differentiating epidermal cells form distinct though naturally blended layers. As the cells displace outward, they flatten and become joined by spiny processes forming the stratum spinosum, or spinous layer. The cells manufacture specialized fats called sphingolipids, and begin to express keratins associated with terminal differentiation. As keratin is produced, it is incorporated into the cellular matrix, strengthening the skin and providing structural support to the outer layers. As the cells migrate further outward and develop characteristic granules that contain proteins which contribute to the aggregation of keratins; they now form part of the granular layer. Cells lose their nuclei in the outer part of this layer, and the granules release their contents contributing to cornification. Vesicles containing lipids discharge into the spaces between the cells, creating a barrier structure that has been suggested to function like bricks (cells) and mortar (lipids). As the cells rise into the outermost layer of the epidermis—the stratum corneum, sometimes called the horny layer or the cornified layer—they take the form of flattened discs, tightly packed together. These flattened cells, called corneocytes, are effectively dead. The lipids of the epidermis play an important role in maintaining skin health, as they help the stratum corneum to regulate water loss while providing a virtually impermeable hydrophobic barrier to the environment. Fully mature keratinocytes function to protect the skin from UV light damage, and help effectuate immune response to environmental stimuli.

The dermis, which lies just beneath the epidermis, is composed largely of the protein collagen. Most of the collagen is organized in bundles which run horizontally through the dermis and which are buried in a jelly-like material called the ground substance. Collagen accounts for up to 75% of the weight of the dermis, and is responsible for the resilience and elasticity of skin. The collagen bundles are held together by elastic fibers running through the dermis. The fibers are comprised of a protein called elastin, and make up less than 5% of the weight of the dermis. Fibroblasts function to synthesize collagen and the dermis ground substance, including components glycoproteins and glycosaminoglycans such as hyaluronic acid (which is able to bind water). The junction between the epidermis and the dermis is not straight but undulates—more markedly so in some areas of the body than others. A series of finger-like structures called rete pegs project up from the dermis, and similar structures project down from the epidermis. These projections increase the area of contact between the layers of skin, and help to prevent the epidermis from being sheared off. As skin ages, the projections get smaller and flatter. Networks of tiny blood vessels run through the rete pegs, bringing nutrients, vitamins and oxygen to the epidermis, although the epidermis itself is avascular and nourished by diffusion from the rete pegs. The dermis also contains the pilobaceous units comprising hair follicles and sebaceous glands, apocrine and eccrine sweat glands, lymphatic vessels, nerves, and various sensory structures, including the mechano-sensing Pacinian and Meissner's corpuscles.

Beneath the dermis lies the hypodermis, which comprises subcutaneous fat that cushions the dermis from underlying tissues such as muscle and bones. The fat is contained in adipose cells embedded in a connective tissue matrix. This layer may also house the hair follicles when they are in the growing phase.

Thus, skin is a multilayered complex organ comprising a wide variety of cellular types and structures, including epidermal and dermal connective tissue with blood and lymphatic vessels, the pilosebaceous units, glands, nerves, various sensory structures, the hypodermal adipose tissue, and the elastic fascia beneath the hypodermis. In turn, these structures are composed of a number of different cell types including keratinocytes, melanocytes, neuroendocrine Merkel cells, sebocytes, fibroblasts, endothelial cells, pericytes, neurons, adipocytes, myocytes and resident immunocytes including Langerhans cells, other dendritic cells, T cells and mast cells. Two of the main cell lineages in the skin are epithelial cells, which in general form the linings of the body and the parenchyma of many organs and glands, and mesenchymal cells, which form connective tissue, blood vessels and muscle. Dermal fibroblasts are mesenchymal cells, and keratinocytes are epithelial cells, which comprise most of the structure of the epidermis.

Skin aging is likewise a complex multi-factorial process that results from unrepaired cellular and tissue damage leading to impaired functional capacity. The aging process in skin is the result of both intrinsic and extrinsic factors occurring over decades. Skin is subject to many of the same intrinsic aging processes as other organs, but is also exposed to solar radiation, an important extrinsic factor that contributes to premature skin aging or photo-aging. Another important extrinsic factor potentially contributing to skin aging is smoking. There have been major advances in the understanding of the aging process with the identification of cellular pathways and genes associated with longevity and aging. Several theories have been proposed to explain intrinsic aging, including cellular senescence resulting from telomere shortening, mutations in nuclear and mitochondrial DNA, hormonal insufficiency and oxidative stress. Reactive active oxygen species and the direct effects of ultraviolet radiation (UVR) appear to play major roles in photo-aging. As is the case for aging in general, an integrated understanding of skin aging has not been developed.

Skin researchers have categorized age-inducing factors as either intrinsic or extrinsic, although these are interdependent, reflected for example by the fact that extrinsic factors may accelerate intrinsic aging. One example of the complex interplay of factors involves free radicals, which are both generated internally through normal metabolic processes and produced as a consequence of external factors, including UVR exposure. As a result of the age-associated decline in protective internal antioxidant mechanisms, free radicals can reach higher and sustained levels in cells and alter both proteins and DNA in skin. Levels of altered protein and DNA may accumulate causing damage. In addition, ongoing accumulation of damage secondary to internally-generated free radicals combined with those generated from UVR and other external assaults (surfactants, allergens, and other irritants) can promote a chronic inflammatory state. This chronic inflammation compromises skin health and may accelerate the aging process; for example, proteolytic enzymes are produced, resulting in collagen degradation. Activated inflammatory cells resulting from elevations in circulating pro-inflammatory mediators (e.g., prostaglandins, cytokines, histamines) produce reactive oxygen species that can cause oxidative damage to nucleic acids, cellular proteins and lipids. Accumulated damage caused by reactive oxygen species may stimulate a host of cytokine cascades that results in photo-aging and photo-carcinogenesis. These changes may be tied to the appearance of aging skin.

Other changes resulting from the complex interplay between intrinsic and extrinsic factors that may impact the appearance of fine lines, wrinkles and texture include the following:

Epidermal thickness and cellular turnover rate of both the epidermis and the stratum corneum declines and epidermal differentiation is altered.

The dermis becomes thinner as major structural molecules including collagen, elastin and glycosaminoglycans decrease in amount. The elastic network in photo-damaged skin becomes disorganized and aggregated and the various structural proteins may be modified by glycation. Metalloproteinase activity increases in photo-damaged skin, contributing to the degradation of collagen and elastin.

Convolution of dermal-epidermal junction (rete ridges) flattens with age, resulting in a loss of mechanical strength. This also leads to decreased microcirculation to the upper dermis and, thus, decreased nourishment to the epidermis.

Age-related changes in inter- and intra-cellular signaling lead to decreases in collagen synthesis.

Changes in hyaluronic acid content within the skin occur with age. Hyaluronic acid is a natural moisturizer within the skin, binding up to 1000 times its weight in water. Age-related declines result in compromised moisturization and firmness.

Decreased intracellular energy sources including ATP and NADH lead to an inability of skin cells to sustain youthful skin biochemistry, thereby reducing the skin's ability to maintain and restore youthful skin structure.

In the epidermis, a lack of estrogen slows the activity of the basal keratinocytes, and consequently leads to epidermal atrophy. This atrophic, fragile skin is less well protected by the normal surface film of lipids, because of the slow decline in sebum secretion experienced by everyone as they age. The stratum corneum barrier is less effective, and the skin may develop reactions to irritants, particularly if skin care has been inadequate or too aggressive.

The time necessary to repair the stratum corneum barrier increases considerably with age: the replacement of skin cells takes about twice as long for people over 75 as for those around 30.

These changes may compromise skin's elasticity, firmness and structure—contributing to areas of collapse and irregularity and ultimately manifesting as fine lines, wrinkles and texture problems.

There are many skin care products available to consumers which are directed to improving the health and/or physical appearance of skin tissue, such as keratinous tissue. Many of such products are directed to delaying, minimizing or even eliminating changes typically associated with one or both of aging and environmental damage to skin. Such products may include one or more of the numerous cosmetic agents known to be useful in improving the health and/or appearance of keratinous tissue. Although many such agents are known, an ongoing need exists to identify cosmetic agents that can provide new or improved benefits to skin tissue. There is also a need to identify additional cosmetic agents that provide similar or improved benefits as compared to existing products but which are easier to formulate, produce, and/or market.

Successful identification of anti-aging cosmetic agents has proven to be difficult due to the multi-cellular, multi-factorial processes that occur in skin over the course of decades. In addition, many desirable cosmetic agents may comprise a mixture of compounds with effects and interactions that may not be fully understood. This is often the case with a botanical or other natural extract that may affect many cellular/pathways. An additional challenge for cosmetic formulators is that cosmetics must be very safe and adverse effects generally are not acceptable. Further, while much is known about skin aging, there is much that is still poorly understood or unknown. Conventional in vitro studies of biological responses to potential cosmetic agents involve testing hundreds or thousands of potential agents in various cell types before an agent that gives the desired result can be identified and moved into a next stage of testing. However, such studies can be hindered by the complex or weakly detectable responses typically induced and/or caused by cosmetic agents. Such weak responses arise, in part, due to the great number of genes and gene products involved, and cosmetic agents may affect multiple genes in multiple ways. Moreover, the degree of bioactivity of cosmetic agents may differ for each gene and be difficult to quantify.

For example, niacinamide is a well-known cosmetic agent producing skin benefits such as improved barrier function and anti-inflammatory activity. Niacinamide is a precursor of NADH, which is involved in more than 100 reactions in cellular metabolism. In contrast to drug agents, which are selected for specificity and which are intended to have measurable effects on structure and function of the body, cosmetic agents are selected for effect on appearance and may not effect structure and function of the body to a measurable degree. Cosmetic agents tend to be non-specific with respect to effect on cellular phenotype, and administration to the body is generally limited to application on or close to the body surface.

The value of a connectivity map approach to discover functional connections among cosmetic phenotypes such as aged skin, gene expression perturbation, and cosmetic agent action is counter-indicated by the progenors of the drug-based C-map. The relevant phenotypes are very complex, the genetic perturbations are numerous and weak, and cosmetic agent action is likewise diffuse and by definition, relatively weak. It is unclear whether statistically valid data may be generated from cosmetic C-maps and it is further unclear whether a cell line exists which may provide salient or detectable cosmetic data.

Surprisingly, the present inventors have provided a C-map approach that is generalizable and biologically relevant for identification of potential cosmetic actives, and demonstrate that the C-map concept is viable by use of benchmark cosmetic actives to query the reference data and by identification of new cosmetic actives.

SUMMARY

Accordingly, disclosed herein are novel systems useful for generating potential new actives for the treatment of aged and photo-damaged skin. In particular, by careful selection of cell type, and by generation of a reference collection of gene-expression profiles for known cosmetic actives, the present inventors were surprisingly able to create system that utilizes a connectivity map for testing and generating hypotheses about cosmetic actives and cosmetic conditions. The present investigators confirmed the validity of connectivity mapping as a tool for identifying cosmetic agents efficacious in the treatment of aged and photo-damaged skin. Potentially efficacious cosmetic agents were identified using gene expression signatures derived from multi-cellular, full thickness human skin biopsies that were compared to short term in vitro experiments of simple cell culture systems. Based on the counter-intuitive and surprising discovery that a fibroblast cell line appears particularly predicative for use with some skin aging gene expression signatures (e.g., a photo-aging gene expression signature), while a combination of fibroblast and keratinocyte cell lines appears more predictive for other skin aging conditions (e.g., intrinsically aged skin), the invention provides methods and systems uniquely suited for desired treatment targets.

It has been discovered that it is possible to derive unique photo-aging and intrinsic aging gene expression signatures for use in a connectivity map, particularly where the photo-aging gene expression signature is derived from a full thickness biopsy of skin that was chronologically or intrinsically aged. It has also been surprisingly discovered that that by utilizing a plurality of unique skin aging gene expression signatures in a connectivity map, useful cosmetic skin care agents can be identified.

Disclosed herein are methods and systems for determining relationships between a skin aging tissue condition of interest and one or more cosmetic agents, one or more genes associated with the skin aging tissue condition, and one or more cells associated with the skin aging tissue condition. Such methods and systems may be used to identify cosmetic agents without detailed knowledge of the mechanisms of biological processes associated with a skin aging condition of interest, all of the genes associated with such a condition, or the cell types associated with such a condition.

A system for identifying connections between a cosmetic agent and at least one gene associated with a skin aging condition is disclosed herein. According to one embodiment, the system comprises (a) at least one computer readable medium having stored thereon a plurality of instances and a skin aging gene expression signature, wherein each instance comprises an ordered list comprising a plurality of identifiers representing a plurality of up-regulated and a plurality of down regulated genes differentially expressed in response to contact between the cosmetic agent and a human fibroblast cell or a human keratinocyte cell, and wherein the skin aging gene expression signature comprises one or more lists comprising a plurality of identifiers representing a plurality of up-regulated genes and a plurality of down-regulated genes associated with a skin aging condition; and (b) a first computing device comprising computer-readable instructions that cause the computing device to: (i) access the plurality of instances and the skin aging gene expression signature stored on the computer readable medium; (ii) comparing each of the instances to the skin aging gene expression signature, wherein the comparison comprises comparing each identifier in the gene expression signature list(s) with the position of the same identifier in the instance list; and (iii) assigning a connectivity score to each of the plurality of instances based on the comparison in (ii).

In other aspects, the invention provides inventive gene expression signatures which may exist tangibly in various forms known in the art. For example, a gene expression signature may exist as a set of immobilized oligonucleotides wherein each oligonucleotide uniquely hybridizes to a nucleotide sequence identifying a region of a gene in the signature. In a specific embodiment, a gene expression signature for intrinsically aged skin consisting of genes selected from the genes set forth in Table E is provided. In another specific embodiment, a gene expression signature for photoaged skin consisting of genes selected from the genes set forth in Table F is provided. It is understood that the "genes set forth" in a table refers to gene identifiers designating the genes, and that a genetic signature as set forth herein is set forth according to a gene identifier.

According to yet another embodiment, a computer readable medium comprising the inventive data architecture is provided. The computer readable medium comprises a first digital file stored in a spreadsheet file format, a word processing file format, or a database file format suitable to be read by a respective spreadsheet, word processing, or database computer program, the first digital file comprising data arranged to provide one or more gene expression signature lists comprising a plurality of identifiers when read by the respective spreadsheet, word processing, or database computer program; and wherein each identifier is selected from the group consisting of a microarray probe set ID, a human gene name, a human gene symbol, and combinations thereof representing a gene set forth in Table E and wherein the gene expression signature list comprises between about 50 and about 600 identifiers.

These and additional objects, embodiments, and aspects of the invention will become apparent by reference to the Figures and Detailed Description below.

DETAILED DESCRIPTION

Figure 1:
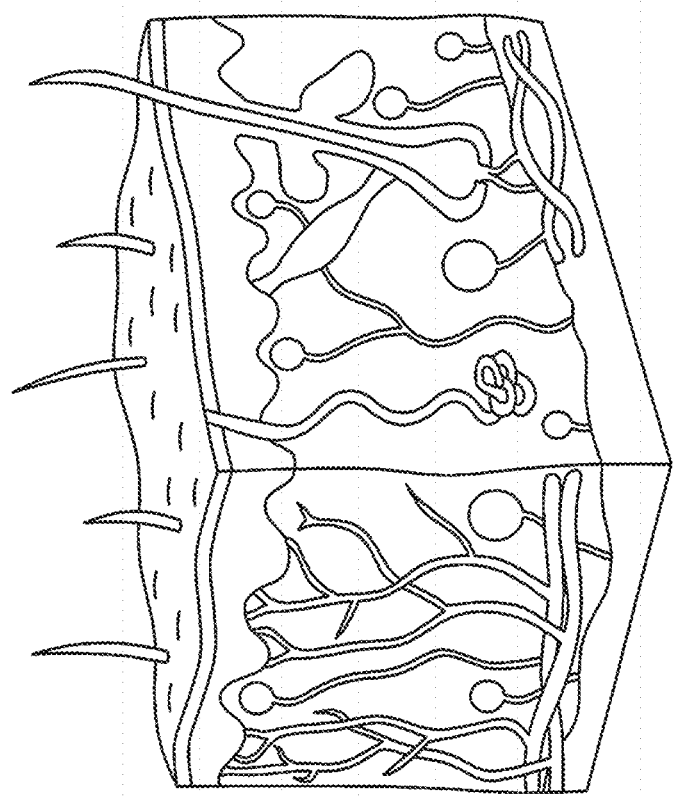
FIG. 1 is a schematic illustration of the epidermal, dermal, and subcutaneous skin layers.

The present invention will now be described with occasional reference to the specific embodiments of the invention. This invention may, however, be embodied in different forms and should not be construed as limited to the embodiments set forth herein. Rather, these embodiments are provided so that this disclosure will be thorough and complete, and to fully convey the scope of the invention to those skilled in the art.

Tables A through J are submitted herewith as .txt files in accordance with large tabled data submission guidelines. Tables A through J in the .txt file format are incorporated herein, in their entirety, by this reference. Table A is a table of 300 identifiers for genes up-regulated in response to skin intrinsic aging conditions. Table B is a table of 300 identifiers for genes down-regulated in response to skin intrinsic aging conditions. Table C is a table of 300 identifiers for genes up-regulated in response to skin photo-aging conditions. Table D is a table of 300 identifiers for genes down-regulated in response to skin photo-aging conditions. Table E reflects an exemplary instance according to certain embodiments of the invention and includes a rank-ordered list of identifiers (chip probe set ID) for an illustrative number of high, middle and low ranked genes profiled by the 22,214 probe sets on Affymetrix chip model HG-U133A2.0 in response to exposure of human dermal fibroblast cells to the perturbagen *Cynara scolymus* (artichoke) leaf extract (instance CMP_62_13). Table F reflects an exemplary instance according to certain embodiments of the invention and includes a rank-ordered list of the identifiers (chip probe set ID) for an illustrative number of high, middle and low ranked genes profiled by the 22,214 probe sets on Affymetrix chip model HG-U133A2.0 in response to exposure of human keratinocyte cells to the perturbagen artichoke leaf extract (instance CMP_62_13). Table G reflects an exemplary instance according to certain embodiments of the invention and includes a rank-ordered list of the identifiers (chip probe et ID) for an illustrative number of high, middle and low ranked genes profiled by the 22,214 probe sets on Affymetrix chip model HG-U133A2.0 in response to exposure of human dermal fibroblast cells to the perturbagen carob leaf extract (instance CMP_62_24). Table H reflects an exemplary instance according to certain embodiments of the invention and includes a rank-ordered list of the identifiers (chip probe set ID) for an illustrative number of high, middle and low ranked genes profiled by the 22,214 probe sets on Affymetrix chip model HG-U133A2.0 in response to exposure of human keratinocyte cells to the perturbagen carob leaf extract (instance CMP_61_23). Table I is a list of identifiers for up-regulated Signature 3, a set of genes up-regulated under photo-aging conditions, optimized for fibroblasts. Table J is a list of identifiers for down-regulated Signature 3, a set of genes down-regulated under photo-aging conditions, optimized for fibroblasts.

Unless otherwise defined, all technical and scientific terms used herein have the same meaning as commonly understood by one of ordinary skill in the art to which this invention pertains. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

As used interchangeably herein, the terms "connectivity map" and "C-map" refer broadly to devices, systems, articles of manufacture, and methodologies for identifying relationships between cellular phenotypes or cosmetic conditions, gene expression, and perturbagens, such as cosmetic actives.

As used herein, the term "cosmetic agent" means any substance, as well any component thereof, intended to be rubbed, poured, sprinkled, sprayed, introduced into, or otherwise applied to a mammalian body or any part thereof. Cosmetic agents may include substances that are Generally Recognized as Safe (GRAS) by the US Food and Drug Administration, food additives, and materials used in non-cosmetic consumer products including over-the-counter medications. In some embodiments, cosmetic agents may be incorporated in a cosmetic composition comprising a dermatologically acceptable carrier suitable for topical application to skin. A cosmetic agent includes, but is not limited to, (i) chemicals, compounds, small or large molecules, extracts, formulations, or combinations thereof that are known to induce or cause at least one effect (positive or negative) on skin tissue; (ii) chemicals, compounds, small molecules, extracts, formulations, or combinations thereof that are known to induce or cause at least one effect (positive or negative) on skin tissue and are discovered, using the provided methods and systems, to induce or cause at least one previously unknown effect (positive or negative) on the skin tissue; and (iii) chemicals, compounds, small molecules, extracts, formulations, or combinations thereof that are not known have an effect on skin tissue and are discovered, using the provided methods and systems, to induce or cause an effect on skin tissue.

Some examples of cosmetic agents or cosmetically actionable materials can be found in: the PubChem database associated with the National Institutes of Health, USA (http://pubchem.ncbi.nlm.nih.gov); the Ingredient Database of the Personal Care Products Council (http://online.personalcarecouncil.org/jsp/Home.jsp); and the 2010 International Cosmetic Ingredient Dictionary and Handbook, 13$^{th}$ Edition, published by The Personal Care Products Council; the EU Cosmetic Ingredients and Substances list; the Japan Cosmetic Ingredients List; the Personal Care Products Council, the SkinDeep database (URL: http://www.cosmeticsdatabase.com); the FDA Approved Excipients List; the FDA OTC List; the Japan Quasi Drug List; the US FDA Everything Added to Food database; EU Food Additive list; Japan Existing Food Additives, Flavor GRAS list; US FDA Select

TABLES

The patent contains table(s) that have been included at the end of the specification.

Committee on GRAS Substances; US Household Products Database; the Global New Products Database (GNPD) Personal Care, Health Care, Food/Drink/Pet and Household database (URL: http://www.gnpd.com); and from suppliers of cosmetic ingredients and botanicals.

Other non-limiting examples of cosmetic agents include botanicals (which may be derived from one or more of a root, stem bark, leaf, seed or fruit of a plant). Some botanicals may be extracted from a plant biomass (e.g., root, stem, bark, leaf, etc.) using one more solvents. Botanicals may comprise a complex mixture of compounds and lack a distinct active ingredient. Another category of cosmetic agents are vitamin compounds and derivatives and combinations thereof, such as a vitamin B3 compound, a vitamin B5 compound, a vitamin B6 compound, a vitamin B9 compound, a vitamin A compound, a vitamin C compound, a vitamin E compound, and derivatives and combinations thereof (e.g., retinol, retinyl esters, niacinamide, folic acid, panthenol, ascorbic acid, tocopherol, and tocopherol acetate). Other non-limiting examples of cosmetic agents include sugar amines, phytosterols, hexamidine, hydroxy acids, ceramides, amino acids, and polyols.

The terms "gene expression signature," and "gene-expression signature" refer to a rationally derived list, or plurality of lists, of genes representative of a skin tissue condition or a skin agent. In specific contexts, the skin agent may be a benchmark skin agent or a potential skin agent. Thus, the gene expression signature may serve as a proxy for a phenotype of interest for skin tissue. A gene expression signature may comprise genes whose expression, relative to a normal or control state, is increased (up-regulated), whose expression is decreased (down-regulated), and combinations thereof. Generally, a gene expression signature for a modified cellular phenotype may be described as a set of genes differentially expressed in the modified cellular phenotype over the cellular phenotype. A gene expression signature can be derived from various sources of data, including but not limited to, from in vitro testing, in vivo testing and combinations thereof. In some embodiments, a gene expression signature may comprise a first list representative of a plurality of up-regulated genes of the condition of interest and a second list representative of a plurality of down-regulated genes of the condition of interest.

As used herein, the term "benchmark skin agent" refers to any chemical, compound, small or large molecule, extract, formulation, or combinations thereof that is known to induce or cause a superior effect (positive or negative) on skin tissue. Non-limiting examples of benchmark skin agents include niacinamide, trans-retinoic acid, and hexamidine.

As used herein, the term "query" refers to data that is used as an input to a Connectivity Map and against which a plurality of instances are compared. A query may include a gene expression signature associated with one or both of a skin aging condition and a benchmark skin agent.

The term "instance," as used herein, refers to data from a gene expression profiling experiment in which skin cells are dosed with a perturbagen. In some embodiments, the data comprises a list of identifiers representing the genes that are part of the gene expression profiling experiment. The identifiers may include gene names, gene symbols, microarray probe set IDs, or any other identifier. In some embodiments, an instance may comprise data from a microarray experiment and comprises a list of probe set IDs of the microarray ordered by their extent of differential expression relative to a control. The data may also comprise metadata, including but not limited to data relating to one or more of the perturbagen, the gene expression profiling test conditions, the skin cells, and the microarray.

The term "keratinous tissue," as used herein, refers to keratin-containing layers disposed as the outermost protective covering of mammals which includes, but is not limited to, skin, hair, nails, cuticles, horns, claws, beaks, and hooves. With respect to skin, the term refers to one or all of the dermal, hypodermal, and epidermal layers, which includes, in part, keratinous tissue.

As used herein, the term "skin aging" refers to a human skin tissue condition resulting from the expression or repression of genes, environmental factors (e.g., sun exposure, UVA and/or UVB exposure, smoking), intrinsic factors (e.g. endogenous free radical production or cellular senescence) or interactions there between that produces one or more of fine lines and/or wrinkles, dry skin, inflamed skin, rough skin, sallow skin, telangectasia, sagging skin, enlarged pores, and combinations thereof.

The term "perturbagen," as used herein, means anything used as a challenge in a gene expression profiling experiment to generate gene expression data for use in the present invention. In some embodiments, the perturbagen is applied to fibroblast and/or keratinocyte cells and the gene expression data derived from the gene expression profiling experiment may be stored as an instance in a data architecture. Any substance, chemical, compound, active, natural product, extract, drug [e.g. Sigma-Aldrich LOPAC (Library of Pharmacologically Active Compounds) collection], small molecule, and combinations thereof used as to generate gene expression data can be a perturbagen. A perturbagen can also be any other stimulus used to generate differential gene expression data. For example, a perturbagen may also be UV radiation, heat, osmotic stress, pH, a microbe, a virus, and small interfering RNA. A perturbagen may be, but is not required to be, any cosmetic agent.

The term "dermatologically acceptable," as used herein, means that the compositions or components described are suitable for use in contact with human skin tissue.

As used herein, the term "computer readable medium" refers to any electronic storage medium and includes but is not limited to any volatile, nonvolatile, removable, and non-removable media implemented in any method or technology for storage of information such as computer readable instructions, data and data structures, digital files, software programs and applications, or other digital information. Computer readable media includes, but are not limited to, application-specific integrated circuit (ASIC), a compact disk (CD), a digital versatile disk (DVD), a random access memory (RAM), a synchronous RAM (SRAM), a dynamic RAM (DRAM), a synchronous DRAM (SDRAM), double data rate SDRAM (DDR SDRAM), a direct RAM bus RAM (DRRAM), a read only memory (ROM), a programmable read only memory (PROM), an electronically erasable programmable read only memory (EEPROM), a disk, a carrier wave, and a memory stick. Examples of volatile memory include, but are not limited to, random access memory (RAM), synchronous RAM (SRAM), dynamic RAM (DRAM), synchronous DRAM (SDRAM), double data rate SDRAM (DDR SDRAM), and direct RAM bus RAM (DRRAM). Examples of non-volatile memory include, but are not limited to, read only memory (ROM), programmable read only memory (PROM), erasable programmable read only memory (EPROM), and electrically erasable programmable read only memory (EEPROM). A memory can store processes and/or data. Still other computer readable media include any suitable disk media, including but not limited to, magnetic disk drives, floppy disk drives, tape drives, Zip drives, flash memory cards, memory sticks, compact disk ROM (CD-ROM), CD recordable drive (CD-R drive), CD rewriteable drive (CD-RW drive), and digital versatile ROM drive (DVD ROM).

As used herein, the terms "software" and "software application" refer to one or more computer readable and/or executable instructions that cause a computing device or other electronic device to perform functions, actions, and/or behave in a desired manner. The instructions may be embodied in one or more various forms like routines, algorithms, modules, libraries, methods, and/or programs. Software may be implemented in a variety of executable and/or loadable forms and can be located in one computer component and/or distributed between two or more communicating, co-operating, and/or parallel processing computer components and thus can be loaded and/or executed in serial, parallel, and other manners. Software can be stored on one or more computer readable medium and may implement, in whole or part, the methods and functionalities of the present invention.

As used herein, the term "intrinsic aging gene expression signature" refers to a gene expression signature derived from gene expression profiling of an intrinsic aging skin condition.

As used herein, the term "intrinsic aging skin condition" refers to a skin aging condition that derives, in whole or part, from chronological aging of the skin.

As used herein, the term "photo-aging skin condition" refers to a skin aging condition that derives, in whole or part, from exposure to sunlight and/or ultraviolet light (e.g., UVR, UVA, UVB, and/or UVC).

As used herein, the term "photo-aging gene expression signature" refers to a gene expression signature derived from gene expression profiling of a photo-aging skin condition.

As used herein, the term "connectivity score" refers to a derived value representing the degree to which an instance correlates to a query.

As used herein, the term "data architecture" refers generally to one or more digital data structures comprising an organized collection of data. In some embodiments, the digital data structures can be stored as a digital file (e.g., a spreadsheet file, a text file, a word processing file, a database file, etc.) on a computer readable medium. In some embodiments, the data architecture is provided in the form of a database that may be managed by a database management system (DBMS) that is be used to access, organize, and select data (e.g., instances and gene expression signatures) stored in a database.

As used herein, the terms "gene expression profiling" and "gene expression profiling experiment" refer to the measurement of the expression of multiple genes in a biological sample using any suitable profiling technology. For example, the mRNA expression of thousands of genes may be determined using microarray techniques. Other emerging technologies that may be used include RNA-Seq or whole transcriptome sequencing using NextGen sequencing techniques.

As used herein, the term "microarray" refers broadly to any ordered array of nucleic acids, oligonucleotides, proteins, small molecules, large molecules, and/or combinations thereof on a substrate that enables gene expression profiling of a biological sample. Non-limiting examples of microarrays are available from Affymetrix, Inc.; Agilent Technologies, Inc.; Ilumina (two "1"'s?), Inc.; GE Healthcare, Inc.; Applied Biosystems, Inc.; Beckman Coulter, Inc.; etc.

Unless otherwise indicated, all numbers expressing quantities of ingredients, properties such as molecular weight, reaction conditions, and so forth as used in the specification and claims are to be understood as being modified in all instances by the term "about". Additionally, the disclosure of any ranges in the specification and claims are to be understood as including the range itself and also anything subsumed therein, as well as endpoints. All numeric ranges are inclusive of narrower ranges; delineated upper and lower range limits are interchangeable to create further ranges not explicitly delineated. Unless otherwise indicated, the numerical properties set forth in the specification and claims are approximations that may vary depending on the desired properties sought to be obtained in embodiments of the present invention. Notwithstanding that numerical ranges and parameters setting forth the broad scope of the invention are approximations, the numerical values set forth in the specific examples are reported as precisely as possible. Any numerical values, however, inherently contain certain errors necessarily resulting from error found in their respective measurements.

In accordance with one aspect of the present invention, provided are devices, systems and methods for implementing a connectivity map utilizing one or more query signatures associated with a skin aging condition. The query signatures may be derived in variety of ways. In some embodiments, the query signatures may be gene expression signatures derived from gene expression profiling of full thickness skin biopsies of skin exhibiting a skin aging condition of interest compared to a control (e.g.,photo-damaged skin compared to sun protected skin). The gene expression profiling can be carried out using any suitable technology, including but not limited to microarray analysis or NextGen sequencing. Some examples of gene expression signatures include a photo-aging gene expression signature and an intrinsic aging gene expression signature, examples of which are described more fully hereafter. In other embodiments, the query signature may be derived from benchmark agents known to positively affect, treat, or reverse a skin aging condition, wherein the query signature is derived from a fibroblast and/or keratinocyte cell line exposed to the benchmark skin agent. These query signatures may be used singularly or in combination.

In accordance with another aspect of the present invention, provided are devices, systems, and methods for implementing a connectivity map utilizing one or more instances derived from a perturbagen, such as a cosmetic agent, exposed to a fibroblast (e.g., BJ fibroblasts) and/or keratinocyte (e.g., telomerized human keratinocytes) skin cell line. Instances from more complex cell culture systems may also be used, such as skin organotypic cultures containing both keratinocytes and fibroblasts or ex vivo human skin. Instances from a plurality of cell lines may be used with the present invention.

In accordance with yet another aspect of the present invention, provided are devices, systems and methods for identification of relationships between a skin aging query signature and a plurality of instances. For example, it may be possible to ascertain perturbagens that give rise to a statistically significant activity on a statistically significant number of genes associated with a skin aging tissue condition of interest, leading to the identification of new cosmetic agents for treating a skin condition or new uses of known cosmetic agents.

I. Systems and Devices

Figure 2:
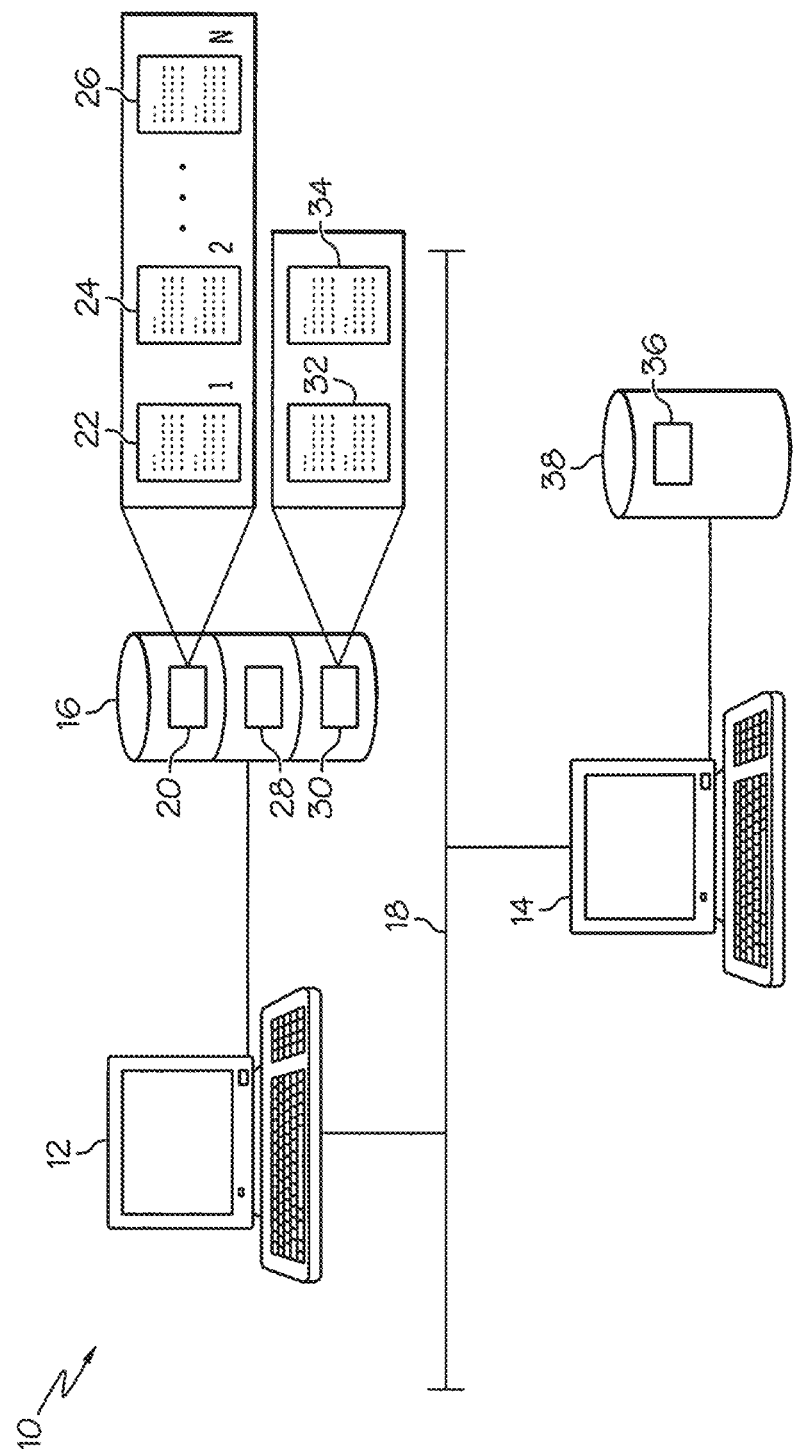
FIG. 2 is a schematic illustration of a computer system suitable for use with the present invention.
Figure 4:
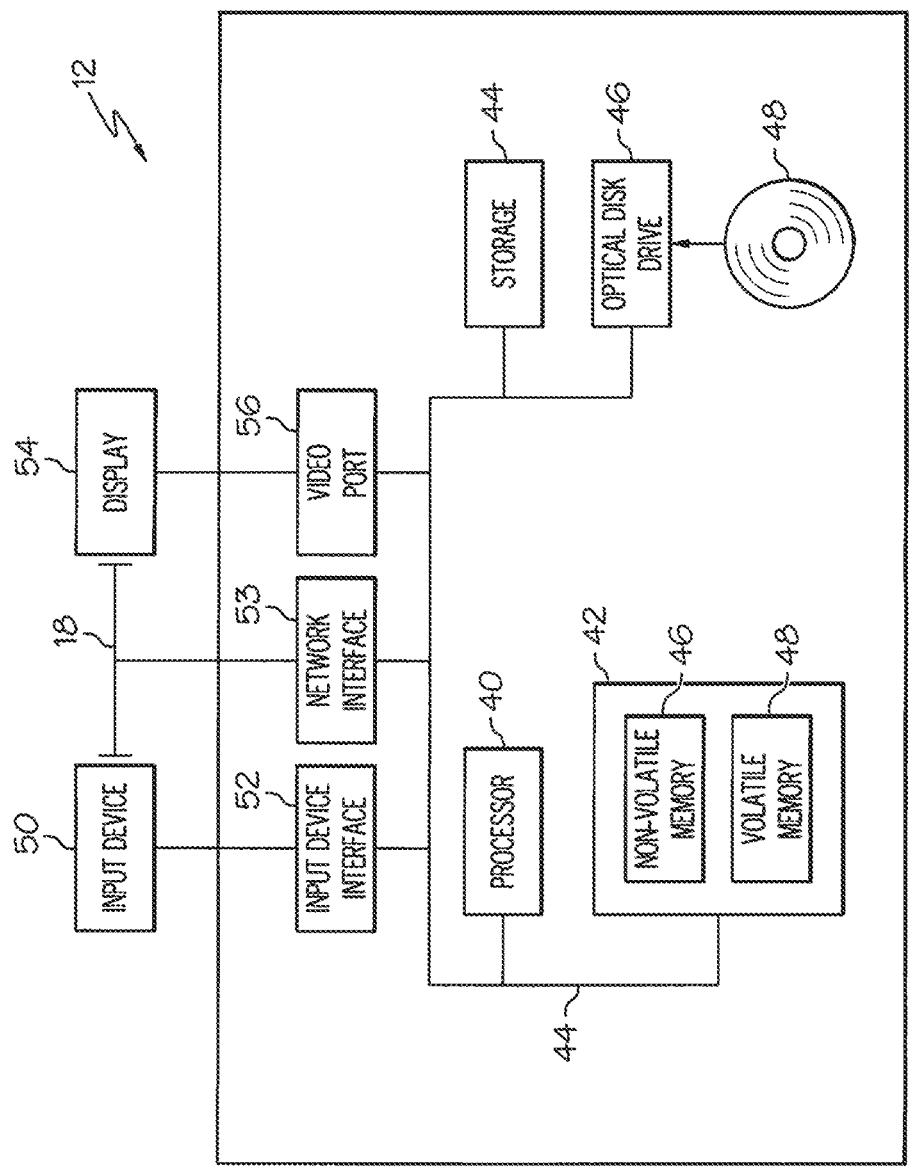
FIG. 4 is a schematic illustration of a programmable computer suitable for use with the present invention.
Figure 5:
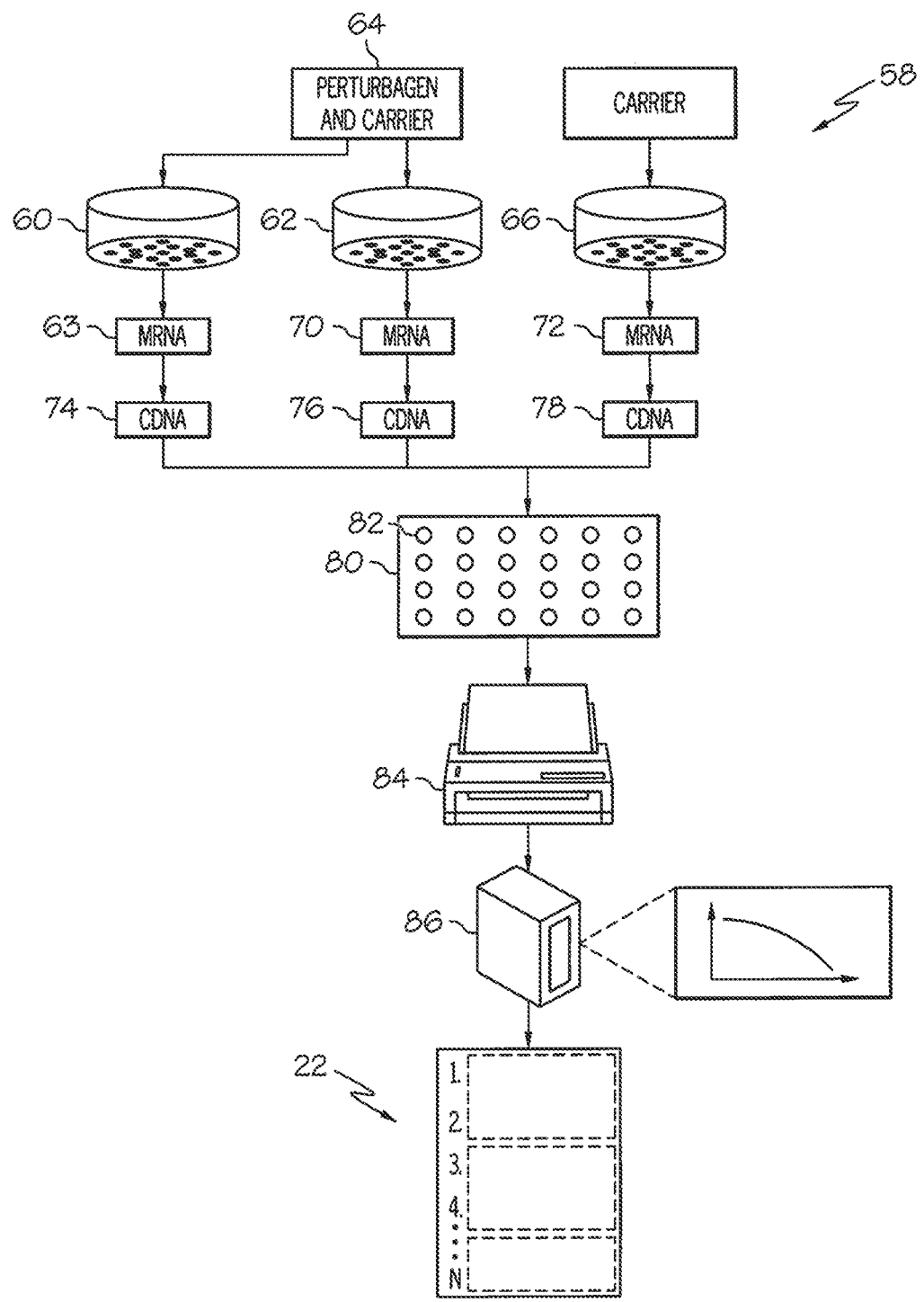
FIG. 5 is a schematic illustration of an exemplary system for generating an instance.

Referring to FIGS. 2, 4 and 5, some examples of systems and devices in accordance with the present invention for use in identifying relationships between perturbagens, skin aging tissue conditions, and genes associated with the skin aging tissue condition will now be described. System 10 comprises one or more of computing devices 12, 14, a computer readable medium 16 associated with the computing device 12, and communication network 18.

The computer readable medium 16, which may be provided as a hard disk drive, comprises a digital file 20, such as a database file, comprising a plurality of instances 22, 24, and 26 stored in a data structure associated with the digital file 20. The plurality of instances may be stored in relational tables and indexes or in other types of computer readable media. The instances 22, 24, and 26 may also be distributed across a plurality of digital files, a single digital file 20 being described herein however for simplicity.

The digital file 20 can be provided in wide variety of formats, including but not limited to a word processing file format (e.g., Microsoft Word), a spreadsheet file format (e.g., Microsoft Excel), and a database file format. Some common examples of suitable file formats include, but are not limited to, those associated with file extensions such as *.xls, *.xld, *.xlk, *.xll, *.xlt, *.xlxs, *.dif, *.db, *.dbf, *.accdb, *.mdb, *.mdf, *.cdb, *.fdb, *.csv, *sql, *.xml, *.doc, *.txt, *.rtf, *.log, *.docx, *.ans, *.pages, *.wps, etc.

Figure 3:
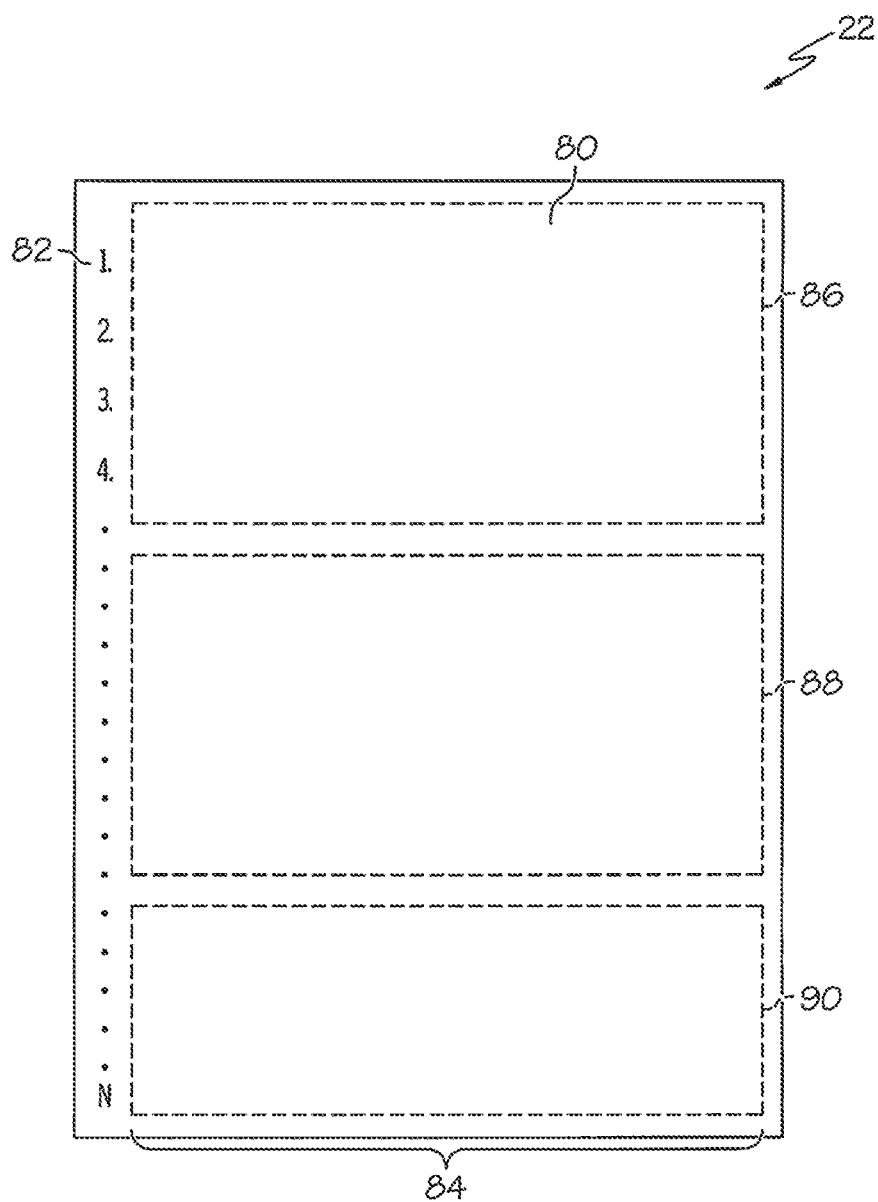
FIG. 3 is a schematic illustration of an instance associated with a computer readable medium of the computer system of FIG. 2.

Referring to FIG. 3, in some embodiments the instance 22 may comprise an ordered listing of microarray probe set IDs, wherein the value of N is equal to the total number of probes on the microarray used in analysis. Common microarrays include Affymetrix GeneChips and Illumina BeadChips, both of which comprise probe sets and custom probe sets. To generate the reference gene profiles according to the invention, preferred chips are those designed for profiling the human genome. Examples of Affymetrix chips with utility in the instant invention include model Human Genome (HG)-U133 Plus 2.0. A specific Affymetrix chip employed by the instant investigators is HG-U133A2.0, however it will be understood by a person or ordinary skill in the art that any chip or microarray, regardless of proprietary origin, is suitable so long as the probe sets of the chips used to construct a data architecture according to the invention are substantially similar.

Instances derived from microarray analyses utilizing Affymetrix GeneChips may comprise an ordered listing of gene probe set IDs where the list comprises 22,000+ IDs. The ordered listing may be stored in a data structure of the digital file 20 and the data arranged so that, when the digital file is read by the software application 28, a plurality of character strings are reproduced representing the ordered listing of probe set IDs. An example of an ordered listing of probe set IDs for a perturbagen having the INCI name *Cynara scolymus* (artichoke leaf extract) is set forth in Table E, which specifically includes an ordered list derived from a microarray analysis of fibroblast cells dosed with *Cynara scolymus*. Table F is a table of rank-ordered identifiers in association with the rank as derived from a microarray analysis of keratinocyte cells dosed with *Cynara scolymus*. While it is preferred that each instance comprise a full list of the probe set IDs, it is contemplated that one or more of the instances may comprise less than all of the probe set IDs of a microarray. It is also contemplated that the instances may include other data in addition to or in place of the ordered listing of probe set IDs. For example, an ordered listing of equivalent gene names and/or gene symbols may be substituted for the ordered listing of probe set IDs. Additional data may be stored with an instance and/or the digital file 20. In some embodiments, the additional data is referred to as metadata and can include one or more of cell line identification, batch number, exposure duration, and other empirical data, as well as any other descriptive material associated with an instance ID. The ordered list may also comprise a numeric value associated with each identifier that represents the ranked position of that identifier in the ordered list.

Referring again to FIGS. 2, 3 and 4, the computer readable medium 16 may also have a second digital file 30 stored thereon. The second digital file 30 comprises one or more lists 32 of microarray probe set IDs associated with one or more skin aging gene expression signatures. The listing 32 of microarray probe set IDs typically comprises a much smaller list of probe set IDs than the instances of the first digital file 20. In some embodiments, the list comprises between 2 and 1000 probe set IDs. In other embodiments the list comprises greater than 10, 50, 100, 200, or 300 and/or less than about 800, 600, or about 400 probe set IDs. The listing 32 of probe set IDs of the second digital file 30 comprises a list of probe set IDs representing up, and/or down-regulated genes selected to represent a skin aging condition of interest. In some embodiments, a first list may represent the up-regulated genes and a second list may represent the down-regulated genes of the gene expression signature. The listing(s) may be stored in a data structure of the digital file 30 and the data arranged so that, when the digital file is read by the software application 28, a plurality of character strings are reproduced representing the list of probe set IDs. Instead of probe set IDs, equivalent gene names and/or gene symbols (or another nomenclature) may be substituted for a list of probe set IDs. Additional data may be stored with the gene expression signature and/or the digital file 30 and this is commonly referred to as metadata, which may include any associated information, for example, cell line or sample source, and microarray identification. Examples of listings of probe set IDs for intrinsic aging gene expression signatures are set forth in Tables A (up-regulated) and B (down-regulated), and an example of listings of probe set IDs for photo-aging gene expression signatures are set forth in Tables C (up-regulated) and D (down-regulated). In some embodiments, one or more skin aging gene expression signatures may be stored in a plurality of digital files and/or stored on a plurality of computer readable media. In other embodiments, a plurality of gene expression signatures (e.g., 32, 34) may be stored in the same digital file (e.g., 30) or stored in the same digital file or database that comprises the instances 22, 24, and 26.

As previously described, the data stored in the first and second digital files may be stored in a wide variety of data structures and/or formats. In some embodiments, the data is stored in one or more searchable databases, such as free databases, commercial databases, or a company's internal proprietary database. The database may be provided or structured according to any model known in the art, such as for example and without limitation, a flat model, a hierarchical model, a network model, a relational model, a dimensional model, or an object-oriented model. In some embodiments, at least one searchable database is a company's internal proprietary database. A user of the system 10 may use a graphical user interface associated with a database management system to access and retrieve data from the one or more databases or other data sources to which the system is operably connected. In some embodiments, the first digital file 20 is provided in the form of a first database and the second digital file 30 is provided in the form of a second database. In other embodiments, the first and second digital files may be combined and provided in the form of a single file.

In some embodiments, the first digital file 20 may include data that is transmitted across the communication network 18 from a digital file 36 stored on the computer readable medium 38. In one embodiment, the first digital file 20 may comprise gene expression data obtained from a cell line (e.g., a fibroblast cell line and/or a keratinocyte cell line) as well as data from the digital file 36, such as gene expression data from other cell lines or cell types, gene expression signatures, perturbagen information, clinical trial data, scientific literature, chemical databases, pharmaceutical databases, and other such data and metadata. The digital file 36 may be provided in the form of a database, including but not limited to Sigma-Aldrich LOPAC collection, Broad Institute C-MAP collection, GEO collection, and Chemical Abstracts Service (CAS) databases.

The computer readable medium 16 (or another computer readable media, such as 16) may also have stored thereon one or more digital files 28 comprising computer readable instructions or software for reading, writing to, or otherwise managing and/or accessing the digital files 20, 30. The computer readable medium 16 may also comprise software or computer readable and/or executable instructions that cause the computing device 12 to perform one or more steps of the methods of the present invention, including for example and without limitation, the step(s) associated with comparing a gene expression signature stored in digital file 30 to instances 22, 24, and 26 stored in digital file 20. In some embodiments, the one or more digital files 28 may form part of a database management system for managing the digital files 20, 28. Non-limiting examples of database management systems are described in U.S. Pat. Nos. 4,967,341 and 5,297,279.

The computer readable medium 16 may form part of or otherwise be connected to the computing device 12. The computing device 12 can be provided in a wide variety of forms, including but not limited to any general or special purpose computer such as a server, a desktop computer, a laptop computer, a tower computer, a microcomputer, a mini computer, and a mainframe computer. While various computing devices may be suitable for use with the present invention, a generic computing device 12 is illustrated in FIG. 4. The computing device 12 may comprise one or more components selected from a processor 40, system memory 42, and a system bus 44. The system bus 44 provides an interface for system components including but not limited to the system memory 42 and processor 40. The system bus 36 can be any of several types of bus structures that may further interconnect to a memory bus (with or without a memory controller), a peripheral bus, and a local bus using any of a variety of commercially available bus architectures. Examples of a local bus include an industrial standard architecture (ISA) bus, a microchannel architecture (MSA) bus, an extended ISA (EISA) bus, a peripheral component interconnect (PCI) bus, a universal serial (USB) bus, and a small computer systems interface (SCSI) bus. The processor 40 may be selected from any suitable processor, including but not limited to, dual microprocessor and other multi-processor architectures. The processor executes a set of stored instructions associated with one or more program applications or software.

The system memory 42 can include non-volatile memory 46 (e.g., read only memory (ROM), erasable programmable read only memory (EPROM), electrically erasable programmable read only memory (EEPROM), etc.) and/or volatile memory 48 (e.g., random access memory (RAM)). A basic input/output system (BIOS) can be stored in the non-volatile memory 38, and can include the basic routines that help to transfer information between elements within the computing device 12. The volatile memory 48 can also include a high-speed RAM such as static RAM for caching data.

The computing device 12 may further include a storage 44, which may comprise, for example, an internal hard disk drive [HDD, e.g., enhanced integrated drive electronics (EIDE) or serial advanced technology attachment (SATA)] for storage. The computing device 12 may further include an optical disk drive 46 (e.g., for reading a CD-ROM or DVD-ROM 48). The drives and associated computer-readable media provide non-volatile storage of data, data structures and the data architecture of the present invention, computer-executable instructions, and so forth. For the computing device 12, the drives and media accommodate the storage of any data in a suitable digital format. Although the description of computer-readable media above refers to an HDD and optical media such as a CD-ROM or DVD-ROM, it should be appreciated by those skilled in the art that other types of media which are readable by a computer, such as Zip disks, magnetic cassettes, flash memory cards, cartridges, and the like may also be used, and further, that any such media may contain computer-executable instructions for performing the methods of the present invention.

A number of software applications can be stored on the drives 44 and volatile memory 48, including an operating system and one or more software applications, which implement, in whole or part, the functionality and/or methods described herein. It is to be appreciated that the embodiments can be implemented with various commercially available operating systems or combinations of operating systems. The central processing unit 40, in conjunction with the software applications in the volatile memory 48, may serve as a control system for the computing device 12 that is configured to, or adapted to, implement the functionality described herein.

A user may be able to enter commands and information into the computing device 12 through one or more wired or wireless input devices 50, for example, a keyboard, a pointing device, such as a mouse (not illustrated), or a touch screen. These and other input devices are often connected to the central processing unit 40 through an input device interface 52 that is coupled to the system bus 44 but can be connected by other interfaces, such as a parallel port, an IEEE 1394 serial port, a game port, a universal serial bus (USB) port, an IR interface, etc. The computing device 12 may drive a separate or integral display device 54, which may also be connected to the system bus 44 via an interface, such as a video port 56.

The computing devices 12, 14 may operate in a networked environment across network 18 using a wired and/or wireless network communications interface 58. The network interface port 58 can facilitate wired and/or wireless communications. The network interface port can be part of a network interface card, network interface controller (NIC), network adapter, or LAN adapter. The communication network 18 can be a wide area network (WAN) such as the Internet, or a local area network (LAN). The communication network 18 can comprise a fiber optic network, a twisted-pair network, a T1/E1 line-based network or other links of the T-carrier/E carrier protocol, or a wireless local area or wide area network (operating through multiple protocols such as ultra-mobile band (UMB), long term evolution (LTE), etc.). Additionally, communication network 18 can comprise base stations for wireless communications, which include transceivers, associated electronic devices for modulation/demodulation, and switches and ports to connect to a backbone network for backhaul communication such as in the case of packet-switched communications.

II. Methods for Creating a Plurality of Instances

In some embodiments, the methods of the present invention may comprise populating at least the first digital file 20 with a plurality of instances (e.g., 22, 24, 26) comprising data derived from a plurality of gene expression profiling experiments, wherein one or more of the experiments comprise exposing dermal fibroblast cells and/or keratinocyte cells (or other skin cells such as human skin equivalent cultures or ex vivo cultured human skin) to at least one perturbagen. For simplicity of discussion, the gene expression profiling discussed hereafter will be in the context of a microarray experiment.

Referring to FIG. 5, one embodiment of a method of the present invention is illustrated. The method 58 comprises exposing a fibroblast cells 60 and/or keratinocyte cells 62 to a perturbagen 64. The perturbagen may be dissolved in a carrier, such as dimethyl sulfoxide (DMSO). After exposure, mRNA is extracted from the cells exposed to the perturbagen and reference cells 66 (e.g., fibroblast or keratinocyte cells) which are exposed to only the carrier. The mRNA 68, 70, 72 may be reverse transcribed to cDNA 64, 76, 78 and marked with different fluorescent dyes (e.g., red and green) if a two color microarray analysis is to be performed. Alternatively, the samples may be prepped for a one color microarray analysis as described in Example 1, and further a plurality of replicates may be processed if desired. The cDNA samples may be co-hybridized to the microarray 80 comprising a plurality of probes 82. The microarray may comprise thousands of probes 82. In some embodiments, there are between 10,000 and 50,000 gene probes 82 present on the microarray 80. The microarray is scanned by a scanner 84, which excites the dyes and measures the amount fluorescence. A computing device 86 may be used to analyze the raw images to determine the expression levels of a gene in the cells 60, 62 relative to the reference cells 66. The scanner 84 may incorporate the functionality of the computing device 86. The expression levels include: i) up-regulation [e.g., greater binding of the test material (e.g., cDNA 74, 76) to the probe than the reference material (e.g., cDNA 78)], or ii) down-regulation [e.g., greater binding of the reference material (e.g., cDNA 78) to the probe than the test material (e.g., cDNA 74, 76)], iii) expressed but not differentially [e.g., similar binding of the reference material (e.g., cDNA 78) to the probe than the test material (e.g., cDNA 74. 76)], and iv) no detectable signal or noise. The up- and down-regulated genes are referred to as differentially expressed. Microarrays and microarray analysis techniques are well known in the art, and it is contemplated that other microarray techniques may be used with the methods, devices and systems of the present invention. For example, any suitable commercial or non-commercial microarray technology and associated techniques may used. Good results have been obtained with Affymetrix GeneChip® technology and Illumina BeadChip™ technology. One illustrative technique is described in Example 1. However, one of skill in the art will appreciate that the present invention is not limited to the methodology of the example and that other methods and techniques are also contemplated to be within its scope.

In a very specific embodiment, an instance consists of the rank ordered data for all of the probe sets on the Affymetrix HG-U133A2.0 GeneChip wherein each probe on the chip has a unique probe set IDentifier. The probe sets are rank ordered by the fold change relative to the controls in the same C-map batch (single instance/average of controls). The probe set IDentifiers are rank-ordered to reflect the most up-regulated to the most down-regulated.

Notably, even for the non-differentially regulated genes the signal values for a particular probe set are unlikely to be identical for the instance and control so a fold change different from 1 will be calculated that can be used for comprehensive rank ordering. In accordance with methods disclosed by Lamb et al. (2006), data are adjusted using 2 thresholds to minimize the effects of genes that may have very low noisy signal values, which can lead to spurious large fold changes. The thresholding is preferably done before the rank ordering. An example for illustrative purposes includes a process wherein a first threshold is set at 20. If the signal for a probe set is below 20, it is adjusted to 20. Ties for ranking are broken with a second threshold wherein the fold changes are recalculated and any values less than 2 are set to 2. For any remaining ties the order depends on the specific sorting algorithm used but is essentially random. The probe sets in the middle of the list do not meaningfully contribute to an actual connectivity score.

The rank ordered data are stored as an instance. The probes may be sorted into a list according to the level of gene expression regulation detected, wherein the list progresses from up-regulated to marginal or no regulation to down-regulated, and this rank ordered listing of probe IDs is stored as an instance (e.g., 22) in the first digital file 20. Referring to FIG. 3, the data associated with an instance comprises the probe ID 80 and a value 82 representing its ranking in the list (e.g., 1, 2, 3, 4 . . . N, where N represents the total number of probes on the microarray). The ordered list 84 may generally comprise approximately three groupings of probe IDs: a first grouping 86 of probe IDs associated with up-regulated genes, a second group 88 of probe IDs associated with genes with marginal regulation or no detectable signal or noise, and a third group 90 of probe IDs associated with down-regulated genes. The most up regulated genes are at or near the top of the list 84 and the most down-regulated genes are at or near the bottom of the list 84. The groupings are shown for illustration, but the lists for each instance may be continuous and the number of regulated genes will depend on the strength of the effect of the perturbagen associated with the instance. Other arrangements within the list 84 may be provided. For example, the probe IDs associated with the down-regulated genes may be arranged at the top of the list 84. This instance data may also further comprise metadata such as perturbagen identification, perturbagen concentration, cell line or sample source, and microarray identification.

In some embodiments, one or more instances comprise at least about 1,000, 2,500, 5,000, 10,000, or 20,000 identifiers and/or less than about 30,000, 25,000, or 20,000 identifiers. In some embodiments, the database comprises at least about 50, 100, 250, 500, or 1,000 instances and/or less than about 50,000, 20,000, 15,000, 10,000, 7,500, 5,000, or 2,500 instances. Replicates of an instance may created, and the same perturbagen may be used to derive a first instance from fibroblast cells and a second instance from keratinocyte cells and a third instance from another skin cell type, such as melanocytes or complex tissue, for example ex vivo human skin.

The present inventors have surprisingly discovered that instances derived from fibroblast cells appear to be more predictive than other cell types when used in combination with a photo-aging gene expression signature. As described more fully hereafter in Example 6, the present inventors compared instances derived from BJ fibroblast cells and keratinocyte cells with a photo-aging gene expression signature and found that instances derived from the fibroblast cells were dramatically over represented in the highest ranking results (the higher the ranking, the more likely the perturbagen is to have a beneficial affect upon the photo aging condition) compared to keratinocyte cells. The inventors also discovered that the up-regulated genes of a photo-aging gene expression signature most closely correlated with instances derived from fibroblast cells. In comparison, the present inventors discovered that a combination of instances derived from fibroblast cells and keratinocyte cells using the same set of perturbagens correlated more closely with an intrinsic aging gene expression signature, with the instances derived from the fibroblast cells being slightly more preferential. The inventors were surprised to find that instances derived from keratinocyte cells were under represented in the top ranking results of the photo-aging gene expression signature, while more equal representation was observed with respect to an intrinsic aging gene expression signature. Still further, both results are surprising considering that the gene expression signatures were derived from full thickness biopsies representing complex, multi-factorial skin aging conditions and further that the photo-aging gene expression signature was derived from a full thickness skin biopsy that was also intrinsically aged. In other words, a photo-aging gene expression signature could be differentiated from biopsy samples containing both intrinsic aging and photo aging phenotypes.

III. Methods for Deriving Skin Aging Gene Expression Signatures

Some methods of the present invention comprise identifying a gene expression signature that represents the up-regulated and down-regulated genes associated with a skin aging condition of interest. A skin aging condition typically involves complex processes involving numerous known and unknown extrinsic and intrinsic factors, as well as responses to such factors that are subtle over a relatively short period of time but non-subtle over a longer period of time. This is in contrast to what is typically observed in drug screening methods, wherein a specific target, gene, or mechanism of action is of interest. Due to the unique screening challenges associated with a skin aging condition, the quality of the gene expression signature representing the condition of interest can be important for distinguishing between the gene expression data actually associated with a response to a perturbagen from the background expression data. One challenge in developing skin aging gene expression signatures is that the number of genes selected needs to be adequate to reflect the dominant and key biology but not so large as to include many genes that have achieved a level of statistical significance by random chance and are non-informative. Thus, query signatures should be carefully derived since the predictive value may be dependent upon the quality of the gene expression signature.

One factor that can impact the quality of the query signature is the number of genes included in the signature. The present inventors have found that, with respect to a cosmetic data architecture and connectivity map, too few genes can result in a signature that is unstable with regard to the highest scoring instances. In other words, small changes to the gene expression signature can result significant differences in the highest scoring instance. Conversely, too many genes may tend to partially mask the dominant biological responses and will include a higher fraction of genes meeting statistical cutoffs by random chance—thereby adding undesirable noise to the signature. The inventors have found that the number of genes desirable in a gene expression signature is also a function of the strength of the biological response associated with the condition and the number of genes needed to meet minimal values (e.g., a p-value less than about 0.05) for statistical significance. When the biology is weaker, such as is the case typically with cosmetic condition phenotypes, fewer genes than those which may meet the statistical requisite for inclusion in the prior art, may be used to avoid adding noisy genes. For example, the gene expression profiling analysis of a photo aging skin condition yielded approximately 4000 genes having a statistical p-value of less than 0.05 and approximately 1000 genes having a p-value of less than 0.001, which could be considered a very strong biological response. The gene expression profiling analysis of an intrinsic aging skin condition yielded approximately 1000 genes have a statistical p-value of less than 0.05 and approximately 400 genes have a p-value of less than 0.001, which could be considered a moderately strong biological response. In these cases, a gene expression signature comprises between about 100 and about 600 genes. Weaker biology may be better represented by a gene expression signature comprising fewer genes.

While a gene expression signature may represent all significantly regulated genes associated with skin aging condition of interest; typically it represents a subset of such genes. The present inventors have discovered that skin aging gene expression signatures comprising between about 200 and about 800 genes of approximately equal numbers of up-regulated and/or down-regulated genes are stable, reliable, and can provide predictive results. For example, a suitable gene expression signature may have from about 200-250 genes, 250-300 genes, 300-350 genes, 350-400 genes, 400-450 genes, 450-500 genes, 500-550 genes, 550-600 genes, 600-650 genes, 650-700 genes, 700-750 genes, and 750-800 genes. However, one of skill in the art will appreciate that gene expression signatures comprising fewer or more genes are also within the scope of the various embodiments of the invention. For purposes of depicting a gene expression signature, the probe set IDs associated with the genes are preferably separated into a first list comprising the most up-regulated genes and a second list comprising the most down-regulated.

Gene expression signatures may be generated from full thickness skin biopsies from skin having the skin aging condition of interest compared to a control. Two gene expression signature types for skin aging can include an intrinsic aging gene expression signature and a photo-aging gene expression signature, which may be derived by comparing gene expression data from a full thickness skin biopsy from skin having the condition of interest and a control. Examples 2 and 3 below describe in greater detail non-limiting methods for deriving these gene expression signatures. Generally, for a photo-aging gene expression signature, biopsies may be taken from sun exposed skin (e.g., extensor forearm) and sun protected skin (e.g., buttocks) of a plurality of older subjects. The subjects may vary in age, but one age range is between about 45 years of age and 70 years of age. A gene expression profiling analysis of the biopsy samples may be performed and one or more photo-aging gene expression signatures derived from a statistical analysis of the results. In some embodiments, the photo-aging gene expression signature comprises about equal numbers of up-regulated and down-regulated genes. In an alternate embodiment, a photo-aging gene expression signature may be derived by comparing a sun exposed site of an older individual (e.g., 45 to 80 y.o.) to a sun exposed site of a younger individual (e.g., 18 to 25 y.o.)

Generally, for an intrinsic aging gene expression signature, biopsies may be taken from sun protected sites (e.g., buttocks) of a plurality of older and younger subjects. The subjects may vary in age, but one age range is between about 45 years of age and 80 years of age for the older subjects and 18 years of age and 25 years of age for the younger subjects. A gene expression profiling analysis of the biopsy samples may be performed and one or more intrinsic aging gene expression signatures derived from a statistical analysis of the microarray results. In some embodiments, the intrinsic aging gene expression signature comprises about equal numbers of up-regulated and down-regulated genes.

In some embodiments, the photo-aging and intrinsic aging gene expression signatures have fewer than 20% of their genes in common, and they reflect different aspects of the biology of aging skin as described. The intrinsic aging gene expression signatures may capture decreased expression of epidermal differentiation markers and down-regulation of pathways involved in the synthesis of lipids important in epidermal barrier function as well as changes related to the dermis, while the photo-aging signatures may be much more reflective of modified biology of the dermis and fibroblasts. Therefore, both photo-aging and intrinsic aging gene expression signatures are useful for identification of cosmetic agents to improve the appearance of aging skin and allow identification of potential perturbagens with differing biological activities.

In other embodiments of the present invention, a gene expression signature may be derived from a gene expression profiling analysis of fibroblast and/or keratinocyte cells treated with a benchmark skin agent to represent cellular perturbations leading to improvement in the skin tissue condition treated with that benchmark skin agent, said signature comprising a plurality of genes up-regulated and down-regulated by the benchmark skin agent in cells in vitro. As one illustrative example, microarray gene expression profile data where the perturbagen is the known skin anti-aging agent all trans-retinoic acid (tRA) may be analyzed using the present invention to determine from the rank-ordered instances in the query results, the genes associated with the highest scoring instances. Thus, a list of genes strongly up-regulated and strongly down-regulated in response to challenge with tRA can be derived, and said list of genes (a proxy for skin anti-aging) can be used as a query signature to screen for skin anti-aging agents. In another embodiment, a signature may be derived to represent more than one aspect of the condition of interest.

Figure 6:
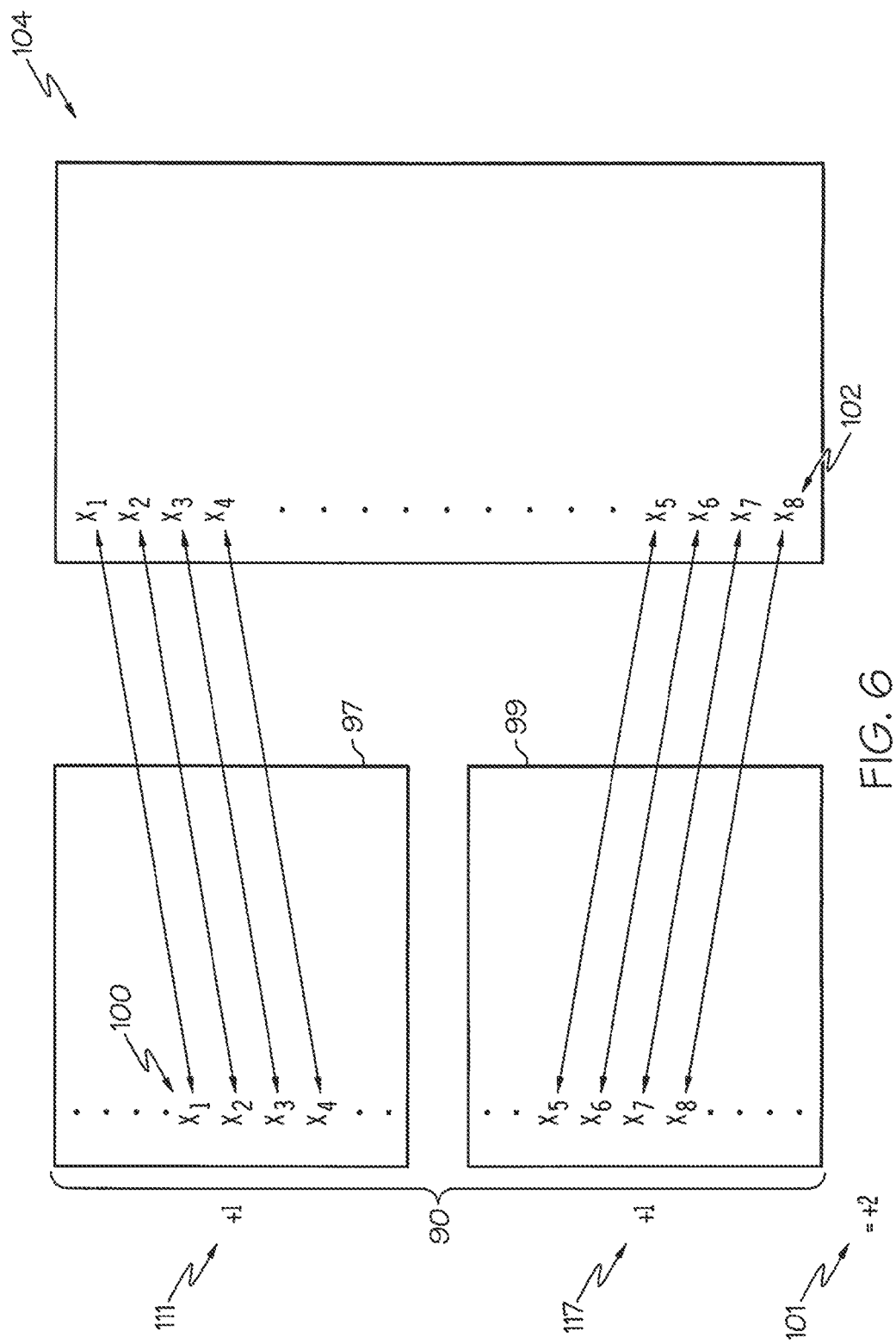
FIG. 6 is a schematic illustration of a comparison between a gene expression signature and an instance, wherein there is a positive correlation between the lists.
Figure 7:
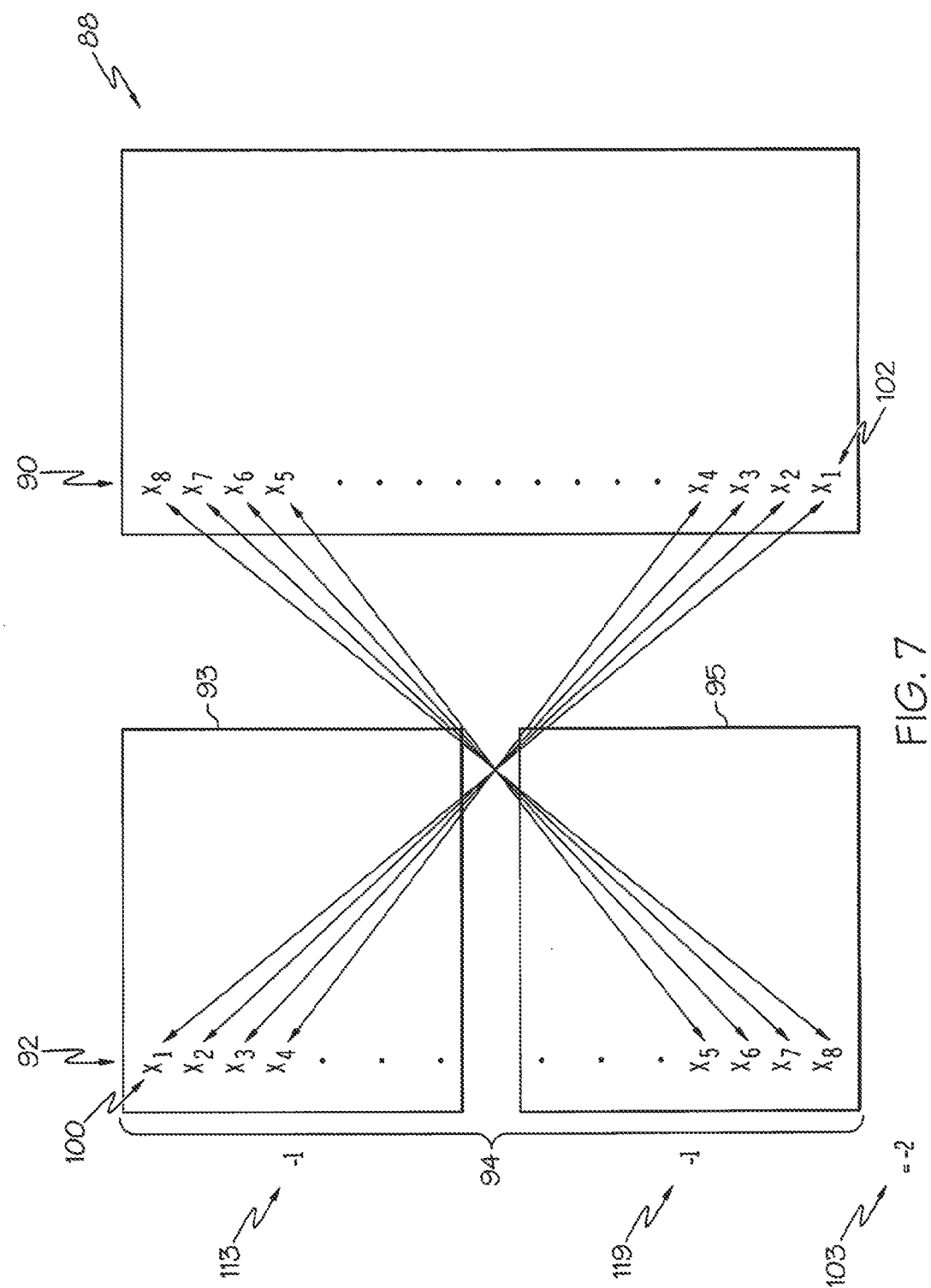
FIG. 7 is a schematic illustration of a comparison between a gene expression signature and an instance, wherein there is a negative correlation between the lists.
Figure 8:
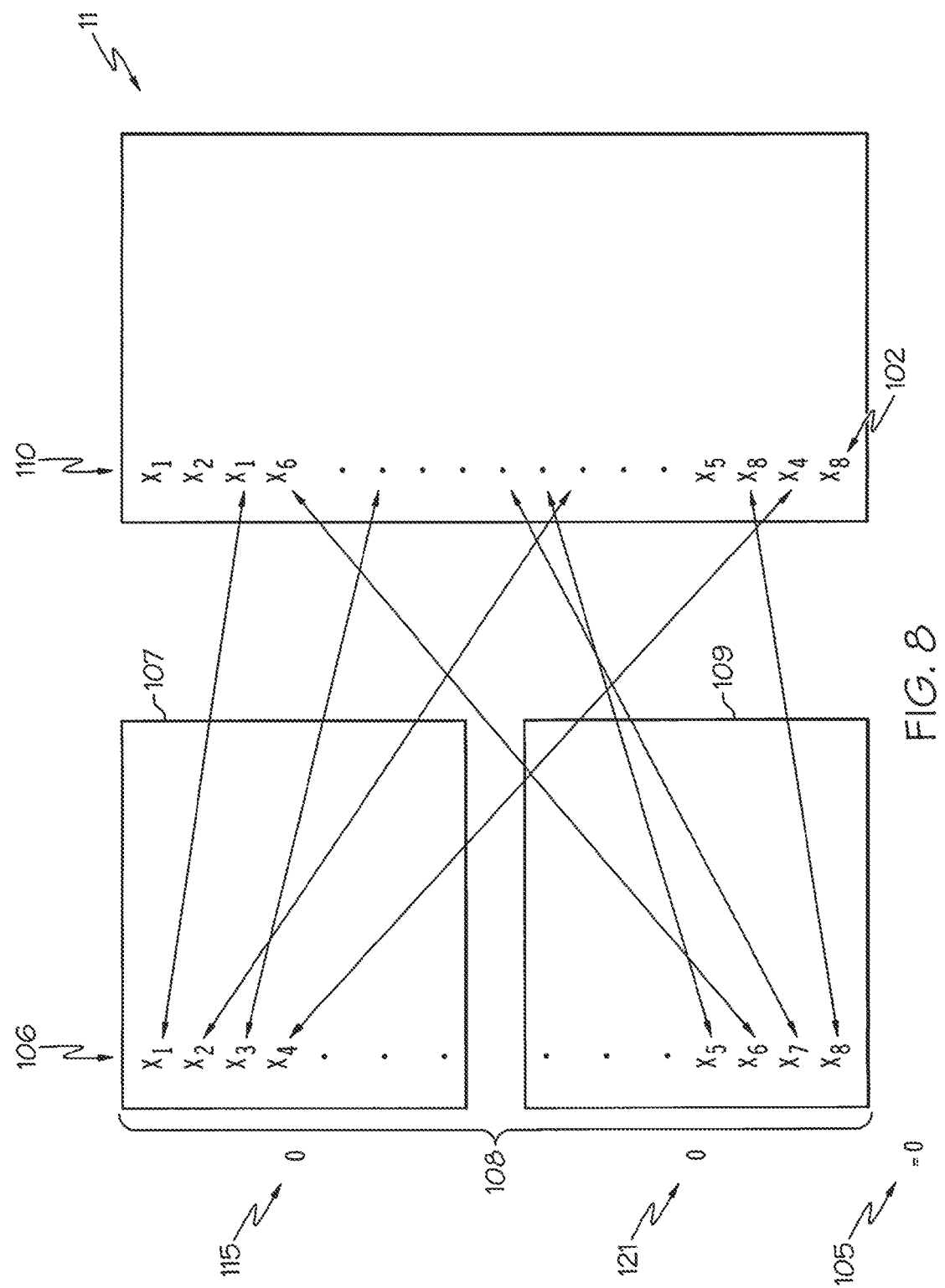
FIG. 8 is a schematic illustration of a comparison between a gene expression signature and an instance, wherein there is a neutral correlation between the lists.

IV. Methods for Comparing a Plurality of Instances to One or More Skin Aging Gene Expression Signatures Referring to FIG. 6 and FIG. 7, a method for querying a plurality of instances with one or more skin aging gene signatures will now be described. Broadly, the method comprises querying a plurality of instances with one or more skin aging gene signatures and applying a statistical method to determine how strongly the signature genes match the regulated genes in an instance. Positive connectivity occurs when the genes in the up-regulated signature list are enriched among the up-regulated genes in an instance and the genes in the down-regulated signature list are enriched among the down-regulated genes in an instance. On the other hand, if the up-regulated genes of the signature are predominantly found among the down-regulated genes of the instance, and vice versa, this is scored as negative connectivity. FIG. 6 schematically illustrates an extreme example of a positive connectivity between signature 90 and the instance 104 comprising the probe IDs 102, wherein the probe IDs of the instance are ordered from most up-regulated to most down-regulated. In this example, the probe IDs 100 (e.g., $X_1$, $X_2$ $X_3$, $X_4$, $X_5$, $X_6$, $X_7$, $X_8$) of the gene signature 90, comprising an up list 97 and a down list 99, have a one to one positive correspondence with the most up-regulated and down-regulated probe IDs 102 of the instance 104, respectively. Similarly, FIG. 7 schematically illustrates an extreme example of a negative connectivity between signature 94 and the instance 88 comprising the probe IDs 90, wherein the probe IDs of the instance are ordered from most up-regulated to most down-regulated. In this example, the probe IDs of the up list 93 (e.g., $X_1$, $X_2$ $X_3$, $X_4$) correspond exactly with the most down-regulated genes of the instance 88, and the probe IDs of the down list 95 (e.g., $X_5$, $X_6$, $X_7$, $X_8$) correspond exactly to the most up-regulated probe IDs of the instance 88. FIG. 8 schematically illustrates an extreme example of neutral connectivity, wherein there is no consistent enrichment of the up- and down-regulated genes of the signature among the up- and down-regulated genes of the instance, either positive or negative. Hence the probe IDs 106 (e.g., $X_1$, $X_2$ $X_3$, $X_4$, $X_5$, $X_6$, $X_7$, $X_8$) of a gene signature 108 (comprising an up list 107 and a down list 109) are scattered with respect to rank with the probe IDs 110 of the instance 112, wherein the probe IDs of the instance are ordered from most up-regulated to most down-regulated. While the above embodiments illustrate process where the gene signature comprises a both an up list and a down list representative of the most significantly up- and down-regulated genes of a skin condition, it is contemplated that the gene signature may comprise only an up list or a down list when the dominant biology associated with a condition of interest shows gene regulation in predominantly one direction.

In some embodiments, the connectivity score can be a combination of an up-score and a down score, wherein the up-score represents the correlation between the up-regulated genes of a gene signature and an instance and the down-score represents the correlation between the down-regulated genes of a gene signature and an instance. The up score and down score may have values between +1 and −1. For an up score (and down score) a high positive value indicates that the corresponding perturbagen of an instance induced the expression of the microarray probes of the up-regulated (or down-regulated) genes of the gene signature, and a high negative value indicates that the corresponding perturbagen associated with the instance repressed the expression of the microarray probes of the up-regulated (or down-regulated) genes of the gene signature. The up-score can be calculated by comparing each identifier of an up list of a gene signature comprising the up-regulated genes (e.g., Tables A, C, I and lists 93, 97, and 107) to an ordered instance list (e.g., Tables E, F, G, H) while the down-score can be calculated by comparing each identifier of a down list of a gene signature comprising the down-regulated genes (see, e.g., Tables B, D, J and down lists 95, 99, and 109) to an ordered instance list (e.g., Tables E, F, G, H). In these embodiments, the gene signature comprises the combination of the up list and the down list.

In some embodiments, the connectivity score value may range from +2 (greatest positive connectivity) to −2 (greatest negative connectivity), wherein the connectivity score (e.g., 101, 103, and 105) is the combination of the up score (e.g., 111, 113, 115) and the down score (e.g., 117, 119, 121) derived by comparing each identifier of a gene signature to the identifiers of an ordered instance list. In other embodiments the connectivity range may be between +1 and −1.

Examples of the scores are illustrated in FIGS. 6, 7 and 8 as reference numerals 101, 103, 105, 111, 113, 115, 117, 119, and 121.

The strength of matching between a signature and an instance represented by the up scores and down scores and/or the connectivity score may be derived by one or more approaches known in the art and include, but are not limited to, parametric and non-parametric approaches. Examples of parametric approaches include Pearson correlation (or Pearson r) and cosine correlation. Examples of non-parametric approaches include Spearman's Rank (or rank-order) correlation, Kendall's Tau correlation, and the Gamma statistic. Generally, in order to eliminate a requirement that all profiles be generated on the same microarray platform, a non-parametric, rank-based pattern matching strategy based on the Kolmogorov-Smirnov statistic (see M. Hollander et al. "*Nonparametric Statistical Methods*"; Wiley, New York, ed. 2, 1999) (see, e.g., pp. 178-185). It is noted, however, that where all expression profiles are derived from a single technology platform, similar results may be obtained using conventional measures of correlation, for example, the Pearson correlation coefficient.

In specific embodiments, the methods and systems of the present invention employ the nonparametric, rank-based pattern-matching strategy based on the Kolmogorov-Smirnov statistic, which has been refined for gene profiling data by Lamb's group, commonly known in the art as Gene Set Enrichment Analysis (GSEA) (see, e.g., Lamb et al. 2006 and Subramanian, A. et al. (2005) *Proc. Natl. Acad Sci U.S.A,* 102, 15545-15550). For each instance, a down score is calculated to reflect the match between the down-regulated genes of the query and the instance, and an up score is calculated to reflect the correlation between the up-regulated genes of the query and the instance. In certain embodiments the down score and up score each may range between −1 and +1. The combination represents the strength of the overall match between the query signature and the instance.

The combination of the up score and down score is used to calculate an overall connectivity score for each instance, and in embodiments where up and down score ranges are set between −1 and +1, the connectivity score ranges from −2 to +2, and represents the strength of match between a query signature and the instance. The sign of the overall score is determined by whether the instance links positivity or negatively to the signature. Positive connectivity occurs when the perturbagen associated with an instance tends to up-regulate the genes in the up list of the signature and down-regulate the genes in the down list. Conversely, negative connectivity occurs when the perturbagen tends to reverse the up and down signature gene expression changes, The magnitude of the connectivity score is the sum of the absolute values of the up and down scores when the up and down scores have different signs. A high positive connectivity score predicts that the perturbagen will tend to induce the condition that was used to generate the query signature, and a high negative connectivity score predicts that the perturbagen will tend to reverse the condition associated with the query signature. A zero score is assigned where the the up and down scores have the same sign, indicating that a perturbagen did not have a consistent impact the condition signature (e.g., up-regulating both the up and down lists).

According to Lamb et al. (2006), there is no standard for estimating statistical significance of connections observed. Lamb teaches that the power to detect connections may be greater for compounds with many replicates. Replicating in this context means that the same perturbagen is profiled multiple times. Where batch to batch variation must be avoided, a perturbagen should be profiled multiple times in each batch. However, since microarray experiments tend to have strong batch effects it is desirable to replicate instances in different batches (i.e., experiments) to have the highest confidence that connectivity scores are meaningful and reproducible.

Each instance may be rank ordered according to its connectivity score to the query signature and the resulting rank ordered list displayed to a user using any suitable software and computer hardware allowing for visualization of data.

In some embodiments, the methods may comprise identifying from the displayed rank-ordered list of instances (i) the one or more perturbagens associated with the instances of interest (thereby correlating activation or inhibition of a plurality of genes listed in the query signature to the one or more perturbagens); (ii) the differentially expressed genes associated with any instances of interest (thereby correlating such genes with the one or more perturbagens, the skin tissue condition of interest, or both); (iii) the cells associated with any instance of interest (thereby correlating such cells with one or more of the differentially expressed genes, the one or more perturbagens, and the skin tissue condition of interest); or (iv) combinations thereof. The one or more perturbagens associated with an instance may be identified from the metadata stored in the database for that instance. However, one of skill in the art will appreciate that perturbagen data for an instance may be retrievably stored in and by other means. Because the identified perturbagens statistically correlate to activation or inhibition of genes listed in the query signature, and because the query signature is a proxy for a skin tissue condition of interest, the identified perturbagens may be candidates for new cosmetic agents, new uses of known cosmetic agents, or to validate known agents for known uses.

In some embodiments, the methods of the present invention may further comprise testing the selected candidate cosmetic agent, using in vitro assays and/or in vivo testing, to validate the activity of the agent and usefulness as a cosmetic agent. Any suitable in vitro test method can be used, including those known in the art, and most preferably in vitro models having an established nexus to the desired in vivo result. For example, MatTek human skin equivalent cultures and skin biopsy assays may be used to evaluate candidate cosmetic agents. In some embodiments, evaluation of selected agents using in vitro assays may reveal, confirm, or both, that one or more new candidate cosmetic agents may be used in conjunction with a known cosmetic agent (or a combination of known cosmetic agents) to regulate a skin aging tissue condition of interest.

V. Cosmetic Compositions and Personal Care Products

Because of the desirability of providing various cosmetic skin anti-aging benefits to a consumer, it may be beneficial to incorporate test agents or compounds identified by one or more of the screening methods described herein into a cosmetic composition suitable for topical application to skin. That is, it may be desirable to include the test agent as an ingredient in the cosmetic composition. In certain embodiments, the cosmetic composition may include a dermatological acceptable carrier, the test agent, and one or more optional ingredients of the kind commonly included in the particular cosmetic compositing being provided.

Dermatologically acceptable carriers should be safe for use in contact with human skin tissue. Suitable carriers may include water and/or water miscible solvents. The cosmetic skin care composition may comprise from about 1% to about 95% by weight of water and/or water miscible solvent. The composition may comprise from about 1%, 3%, 5%, 10%, 15%, 20%, 25%, 30%, 35%, 40%, 45%, 50%, 55%, 60%, 65%, 70%, 75%, 80%, or 85% to about 90%, 85%, 80%, 75%, 70%, 65%, 60%, 55%, 50%, 45%, 40%, 35%, 30%, 25%, 20%, 15%, 10%, or 5% water and/or water miscible solvents. Suitable water miscible solvents include monohydric alcohols, dihydric alcohols, polyhydric alcohols, glycerol, glycols, polyalkylene glycols such as polyethylene glycol, and mixtures thereof. When the skin care composition is in the form of an emulsion, water and/or water miscible solvents are carriers typically associated with the aqueous phase.

Suitable carriers also include oils. The skin care composition may comprise from about 1% to about 95% by weight of one or more oils. The composition may comprise from about 0.1%, 0.5%, 1%, 2%, 5%, 10%, 15%, 20%, 25%, 30%, 35%, 40%, 45%, 50%, 55%, 60%, 65%, 70%, 75%, 80%, 85%, or 90% to about 90%, 85%, 80%, 75%, 70%, 65%, 60%, 55%, 50%, 45%, 40%, 35%, 30%, 25%, 20%, 15%, 10%, 5%, or 3% of one or more oils. Oils may be used to solubilize, disperse, or carry materials that are not suitable for water or water soluble solvents. Suitable oils include silicones, hydrocarbons, esters, amides, ethers, and mixtures thereof. The oils may be volatile or nonvolatile.

Suitable silicone oils include polysiloxanes. Commercially available polysiloxanes include the polydimethylsiloxanes, which are also known as dimethicones, examples of which include the DM-Fluid series from Shin-Etsu, the Vicasil® series sold by Momentive Performance Materials Inc., and the Dow Corning® 200 series sold by Dow Corning Corporation. Specific examples of suitable polydimethylsiloxanes include Dow Corning® 200 fluids (also sold as Xiameter® PMX-200 Silicone Fluids) having viscosities of 0.65, 1.5, 50, 100, 350, 10,000, 12,500 100,000, and 300,000 centistokes.

Suitable hydrocarbon oils include straight, branched, or cyclic alkanes and alkenes. The chain length may be selected based on desired functional characteristics such as volatility. Suitable volatile hydrocarbons may have between 5-20 carbon atoms or, alternately, between 8-16 carbon atoms.

Other suitable oils include esters. The suitable esters typically contained at least 10 carbon atoms. These esters include esters with hydrocarbyl chains derived from fatty acids or alcohols (e.g., mono-esters, polyhydric alcohol esters, and di- and tri-carboxylic acid esters). The hydrocarbyl radicals of the esters hereof may include or have covalently bonded thereto other compatible functionalities, such as amides and alkoxy moieties (e.g., ethoxy or ether linkages, etc.).

Other suitable oils include amides. Amides include compounds having an amide functional group while being liquid at 25° C. and insoluble in water. Suitable amides include N-acetyl-N-butylaminopropionate, isopropyl N-lauroylsarcosinate, and N,N,-diethyltoluamide. Other suitable amides are disclosed in U.S. Pat. No. 6,872,401.

Other suitable oils include ethers. Suitable ethers include saturated and unsaturated fatty ethers of a polyhydric alcohol, and alkoxylated derivatives thereof. Exemplary ethers include $C_{4-20}$ alkyl ethers of polypropylene glycols, and di-$C_{8-30}$ alkyl ethers. Suitable examples of these materials include PPG-14 butyl ether, PPG-15 stearyl ether, dioctyl ether, dodecyl octyl ether, and mixtures thereof.

The skin care composition may comprise an emulsifier. An emulsifier is particularly suitable when the composition is in the form of an emulsion or if immiscible materials are being combined. The skin care composition may comprise from about 0.05%, 0.1%, 0.2%, 0.3%, 0.5%, or 1% to about 20%, 10%, 5%, 3%, 2%, or 1% emulsifier. Emulsifiers may be nonionic, anionic or cationic. Non-limiting examples of emulsifiers are disclosed in U.S. Pat. No. 3,755,560, U.S. Pat. No. 4,421,769, and McCutcheon's, *Emulsifiers and Detergents*, 2010 Annual Ed., published by M. C. Publishing Co. Other suitable emulsifiers are further described in the Personal Care Product Council's *International Cosmetic Ingredient Dictionary and Handbook*, Thirteenth Edition, 2006, under the functional category of "Surfactants—Emulsifying Agents."

Linear or branched type silicone emulsifiers may also be used. Particularly useful polyether modified silicones include KF-6011, KF-6012, KF-6013, KF-6015, KF-6015, KF-6017, KF-6043, KF-6028, and KF-6038 from Shin Etsu. Also particularly useful are the polyglycerolated linear or branched siloxane emulsifiers including KF-6100, KF-6104, and KF-6105 from Shin Etsu. Emulsifiers also include emulsifying silicone elastomers. Suitable silicone elastomers may be in the powder form, or dispersed or solubilized in solvents such as volatile or nonvolatile silicones, or silicone compatible vehicles such as paraffinic hydrocarbons or esters. Suitable emulsifying silicone elastomers may include at least one polyalkyl ether or polyglycerolated unit.

Structuring agents may be used to increase viscosity, thicken, solidify, or provide solid or crystalline structure to the skin care composition. Structuring agents are typically grouped based on solubility, dispersibility, or phase compatibility. Examples of aqueous or water structuring agents include polymeric agents, natural or synthetic gums, polysaccharides, and the like. In one embodiment, the composition may comprises from about 0.0001%, 0.001%, 0.01%, 0.05%, 0.1%, 0.5%, 1%, 2%, 3%, 5% to about 25%, 20%, 10%, 7%, 5%, 4%, or 2%, by weight of the composition, of one or more structuring agents.

Polysaccharides and gums may be suitable aqueous phase thickening agents. Suitable classes of polymeric structuring agents include but are not limited to carboxylic acid polymers, polyacrylamide polymers, sulfonated polymers, high molecular weight polyalkylglycols or polyglycerins, copolymers thereof, hydrophobically modified derivatives thereof, and mixtures thereof. Silicone gums are another oil phase structuring agent. Another type of oily phase structuring agent includes silicone waxes. Silicone waxes may be referred to as alkyl silicone waxes which and are semi-solids or solids at room temperature. Other oil phase structuring agents may be one or more natural or synthetic waxes such as animal, vegetable, or mineral waxes.

The skin care compositions may be generally prepared by conventional methods such as known in the art of making compositions and topical compositions. Such methods typically involve mixing of ingredients in or more steps to a relatively uniform state, with or without heating, cooling, application of vacuum, and the like. Typically, emulsions are prepared by first mixing the aqueous phase materials separately from the fatty phase materials and then combining the two phases as appropriate to yield the desired continuous phase. The compositions are preferably prepared such as to optimize stability (physical stability, chemical stability, photostability, etc.) and/or delivery of active materials. The composition may be provided in a package sized to store a sufficient amount of the composition for a treatment period. The size, shape, and design of the package may vary widely. Certain package examples are described in U.S. Pat. Nos. D570,707; D391,162; D516,436; D535,191; D542,660;

D547,193; D547,661; D558,591; D563,221; 2009/0017080; 2007/0205226; and 2007/0040306.

EXAMPLES

The present invention will be better understood by reference to the following examples which are offered by way of illustration not limitation.

Example 1

Generating Instances

Individual experiments (referred to as batches) generally comprise 30 to 96 samples analyzed using Affymetrix GeneChip® technology platforms, containing 6 replicates of the vehicle control (e.g., DSMO), 2 replicate samples of a positive control that gives a strong reproducible effect in the cell type used (e.g., all trans-retinoic acid for fibroblast cells), and samples of the test material/perturbagen. Replication of the test material is done in separate batches due to batch effects. In vitro testing was performed in 6-well plates to provide sufficient RNA for GeneChip® analysis (2-4 μg total RNA yield/well).

Human telomerized keratinocytes (tKC) were obtained from the University of Texas, Southwestern Medical Center, Dallas, Tex. tKC cells were grown in EpiLife® media with 1× Human Keratinocyte Growth Supplement (Invitrogen, Carlsbad, Calif.) on collagen I coated cell culture flasks and plates (Becton Dickinson, Franklin Lakes, N.J.). Keratinocytes were seeded into 6-well plates at 20,000 cells/cm$^2$ 24 hours before chemical exposure. Human skin fibroblasts (BJ cell line from ATCC, Manassas, Vir.) were grown in Eagle's Minimal Essential Medium (ATCC) supplemented with 10% fetal bovine serum (HyClone, Logan, Utah) in normal cell culture flasks and plates (Corning, Lowell, Mass.). BJ fibroblasts were seeded into 6-well plates at 12,000 cells/cm$^2$ 24 hours before chemical exposure.

All cells were incubated at 37° C. in a humidified incubator with 5% $CO_2$. At t=-24 hours cells were trypsinized from T-75 flasks and plated into 6-well plates in basal growth medium. At t=0 media was removed and replaced with the appropriate dosing solution as per the experimental design. Dosing solutions were prepared the previous day in sterile 4 ml Falcon snap cap tubes. Pure test materials may be prepared at a concentration of 1-200 μM, and botanical extracts may be prepared at a concentration of 0.001 to 1% by weight of the dosing solution. After 6 to 24 hours of chemical exposure, cells were viewed and imaged. The wells were examined with a microscope before cell lysis and RNA isolation to evaluate for morphologic evidence of toxicity. If morphological changes were sufficient to suggest cytotoxicity, a lower concentration of the perturbagen was tested. Cells were then lysed with 350 ul/well of RLT buffer containing β-mercaptoethanol (Qiagen, Valencia, Calif.), transferred to a 96-well plate, and stored at -20° C.

RNA from cell culture batches was isolated from the RLT buffer using Agencourt® RNAdvance Tissue-Bind magnetic beads (Beckman Coulter) according to manufacturer's instructions. 1 μg of total RNA per sample was labeled using Ambion Message Amp™ II Biotin Enhanced kit (Applied Biosystems Incorporated) according to manufacturer's instructions. The resultant biotin labeled and fragmented cRNA was hybridized to an Affymetrix HG-U133A 2.0 GeneChip®, which was then washed, stained and scanned using the protocol provided by Affymetrix.

In one embodiment, an exemplary test perturbagen was *Cynara scolymus* (artichoke) leaf extract obtained from Ichimaru Pharcos, JP. Following generally the procedure described above, a resultant rank-ordered listing of 22,214 probe set IDs (e.g., an instance) for the artichoke leaf perturbagen applied to fibroblast cells was generated and are set forth in Table E. Following generally the procedure described above, a resultant rank-ordered listing of 22,214 probe set IDs (e.g., an instance) for the artichoke leaf extract perturbagen applied to keratinocyte cells was generated and illustrative portions are set forth in Table F. In another aspect, an exemplary test perturbagen was Hydrolyzed *Ceratonia siliqua* (carob) seed extract. Following generally the procedure described above, a resultant rank-ordered listing of 22,214 probe set IDs (e.g., an instance) for the carob seed extract perturbagen applied to fibroblast cells was generated and illustrative portions are set forth in Table G. Following generally the procedure described above, a resultant rank-ordered listing of 22,214 probe set IDs (e.g., an instance) for the carob seed extract perturbagen applied to keratinocyte cells was generated and illustrative portions are set forth in Table H.

Example 2

Deriving a Photo-Aging Gene Expression Signature

A clinical survey study to obtain biopsy specimens for use in the investigation of gene expression patterns associated with sun light-mediated skin aging (photo-aging) was performed. Baseline gene expression patterns were examined in sun-protected and sun-exposed skin from young and aged women to examine gene expression profiles associated with photo-aging. A total of 3 full thickness skin biopsies (~4 mm) were taken from sun-protected (buttocks) and sun-exposed (extensor forearm) body sites from each of 10 young women (aged 18 to 20 years) and 10 older women (aged 60 to 67 years). The older women were selected to have moderate to severe forearm photo-damage. Biopsies were flash frozen in liquid nitrogen and stored at -80° C. until RNA isolation.

Frozen skin biopsies were homogenized in Trizol (Invitrogen) and RNA extracted using the protocol provided by Invitrogen. Since the tissue samples were from full thickness biopsies, RNA was extracted from a variety of cell types within the full-thickness skin sample, including keratinocytes, fibroblasts, melanocytes, endothelial cells, pericytes, nerves, smooth muscle, sebocytes, adipocytes, and immunocytes). RNA was further purified using RNEasy spin columns (Qiagen). Total RNA was quantified using a Nano-Drop spectrophotometer (Thermo Scientific, Waltham, Mass.) and quality was confirmed using an Agilent (Santa Clara, Calif.) 2100 BioAnalyzer. Total RNA (5 μg) was converted to GeneChip targets using the Enzo BioArray labeling procedure (Enzo Life Sciences, Farmingdale, N.Y.) and protocol provided. All biotin-labeled GeneChip targets were hybridized to Affymetrix Human Genome HG-U133 Plus 2.0 GeneChips overnight, which were then washed, stained and scanned using the protocol provided by Affymetrix. Forearm and buttock samples were processed on the same day using the same manufacturing lot of GeneChips.

The samples were analyzed on the Affymetrix HG-U133 Plus 2.0 GeneChips, which contain 54,613 probe sets complementary to the transcripts of more than 20,000 genes. However, instances in the provided database used were derived from gene expression profiling experiments using Affymetrix HG-U133A 2.0 GeneChips, containing 22,214 probe sets, which are a subset of those present on the Plus 2.0 GeneChip. Therefore, in developing gene expression signatures from the clinical data, the probe sets were filtered for those included in the HG-U133A 2.0 gene chips.

Using, generally the following selection process, a statistical analysis of the microarray data was performed to derive a plurality of photo-aging gene expression signatures comprising between about 200 and about 600 up-regulated and down-regulated genes.

a. Filtering based on Absent/Margin/Present Calls. This filter creates a list of potential genes for inclusion in the gene expression signature. For example, a suitable filter may be that at least 50% of the samples in one treatment group must have a Present call for each probe set. Present calls are derived from processing the raw GeneChip data and provide evidence that the gene transcript complementary to a probe set that is actually expressed in the biological sample. The probes that are absent from all samples are likely to be just noisy measurements. This step is important to filter out probe sets that do not contribute meaningful data to the signature. For both photo-aging and intrinsic aging gene expression signatures, the data was filtered for probe sets with at least 10% Present calls provided by the Affymetrix MAS 5 software.

b. Filtering According to a Statistical Measure. For example, a suitable statistical measure may be p-values from a t-test, ANOVA, correlation coefficient, or other model-based analysis. As one example, p-values may be chosen as the statistical measure and a cutoff value of p=0.05 may be chosen. Limiting the signature list to genes that meet some reasonable cutoff for statistical significance compared to an appropriate control is important to allow selection of genes that are characteristic of the biological state of interest. This is preferable to using a fold change value, which does not take into account the noise around the measurements. The t-statistic was used to select the probe sets in the signatures because it is signed and provides an indication of the directionality of the gene expression changes (i.e. up- or down-regulated) as well as statistical significance.

c. Sorting the Probe Sets. All the probe sets are sorted into sets of up-regulated and down-regulated sets using the statistical measure. For example, if a t-test was used to compute p-values, the values (positive and negative) of the t-statistic are used to sort the list since p-values are always positive. The sorted t-statistics will place the sets with the most significant p-values at the top and bottom of the list with the non-significant ones near the middle.

d. Creation of the Gene expression signature. Using the filtered and sorted list created, a suitable number of probe sets from the top and bottom are selected to create a gene expression signature that preferably has approximately the same number of sets chosen from the top as chosen from the bottom. For example, the gene expression signature created may have at least about 10, 50, 100, 200, or 300 and/or less than about 800, 600, or about 400 genes corresponding to a probe set on the chip. The number of probe sets approximately corresponds to the number of genes, but a single gene may be represented by more than one probe set. It is understood that the phrase "number of genes" as used herein, corresponds generally with the phrase "number of probe sets." The number of genes included in the signature was based upon the observations in preliminary studies that indicated signatures with from 200 to 800 probe sets equally divided between up- and down-regulated genes provide stable results with regard to the top scoring chemical instances when using the signature to query the provided database.

For photo-aging, three gene expression signatures were selected as follows:

(i) "Photo-aging 200" signature (P200), which comprises 100 most significant up- and 100 most significant down-regulated probe sets comparing older arm to younger arm as set forth in Tables C and D, respectively;

(ii) "Photo-aging 400" signature (P400), which comprises 200 most significant up- and 200 most significant down-regulated probe sets comparing older arm to younger arm as set forth in Tables C and D, respectively; and (iii) "Photo-aging 600" signature (P600), which comprises 300 most significant up- and 300 most significant down-regulated probe sets comparing older arm to younger arm as set forth in Tables C and D, respectively.

Example 3

Deriving an Intrinsic Aging Gene Expression Signature

A clinical survey study to obtain biopsy specimens for use in the investigation of gene expression patterns associated with chronological (intrinsic) skin aging was performed. Baseline gene expression patterns were examined in sun-protected skin from young and aged women to examine gene expression profiles associated with intrinsic aging. A total of 3 full thickness skin biopsies (~4 mm) were taken from sun-protected (buttocks) body sites from each of 10 young women (aged 18 to 20 years) and 10 older women (aged 60 to 67 years). Biopsies were flash frozen in liquid nitrogen and stored at −80° C. until RNA isolation.

Frozen skin biopsies were homogenized in Trizol (Invitrogen) and RNA extracted using the protocol provided by Invitrogen. Since the tissue samples were from full thickness biopsies, RNA was extracted from a variety of cell types within the full-thickness skin sample, including keratinocytes, fibroblasts, melanocytes, endothelial cells, pericytes, nerves, smooth muscle, sebocytes, adipocytes, and immunocytes). RNA was further purified using RNEasy spin columns (Qiagen). Total RNA was quantified using a NanoDrop spectrophotometer (Thermo Scientific, Waltham, Mass.) and quality was confirmed using an Agilent (Santa Clara, Calif.) 2100 BioAnalyzer. Total RNA (5 μg) was converted to GeneChip targets using the Enzo BioArray labeling procedure (Enzo Life Sciences, Farmingdale, N.Y.) and protocol provided. All biotin-labeled GeneChip targets were hybridized to Affymetrix Human Genome HG-U133 Plus 2.0 gene chips overnight, which were then washed, stained and scanned using the protocol provided by Affymetrix. Samples were processed on the same day using the same manufacturing lot of gene chips.

Using, generally the same sorting process as set forth in Example 2, a statistical analysis of the microarray data was performed to derive intrinsic aging gene expression signatures comprising between about 200 genes and about 600 genes.

(i) "Intrinsic Aging 200" signature (I200), which comprises 100 most significant up- and 100 most significant down-regulated probe sets comparing older buttock to younger buttock as set forth in Table A and B, respectively.

(ii) "Intrinsic Aging 400" signature (I400), which comprises 200 most significant up- and 200 most significant down-regulated probe sets older buttock to younger buttock as set forth in Table A and B, respectively.

(iii) "Intrinsic Aging 600" signature (I600), which comprises 300 most significant up- and 300 most significant down-regulated probe sets older buttock to younger buttock as set forth in Table A and B, respectively.

The photo-aging gene expression signatures and the intrinsic aging gene expression signatures may be used in whole or part, or they may be used in combination as a query in the present invention. In some embodiments, the gene expression signature comprises the set of most up-regulated or most down-regulated genes. In some embodiments, the photo-aging gene expression signature and intrinsic aging gene expression signature may have between about 10% and 50% of their probe set IDs in common. In other embodiments, the photo-aging gene expression signature and the intrinsic aging gene expression signature may have between about 20% and 30% of their probe set IDs in common. Some materials tested in C-map link to only to gene expression signatures developed for one of the types of skin aging because these agents may be affecting different biology. For example, the inventors have found that the photo-aging gene expression signatures show strong preferential linkage to perturbagen instances tested in fibroblasts and the gene expression changes are more reflective of changes in the dermal connective tissue. In contrast, the intrinsic aging gene expression signatures reflect changes in both the epidermis and dermis that occur with aging. Therefore, it is useful to query the connectivity map with separate signatures derived for both intrinsic aging and photo-aging. Also, it is desirable to use signatures with different numbers of genes. Predictions of biological activity based on multiple signatures are more likely to be correct.

Example 4

Photo-Aging Gene Expression Signature and Intrinsic Aging Gene Expression Signature Comparison to Fibroblast and Keratinocyte Instances The inventors observed that photo-aging gene signatures (e.g., Example 2) have a strong preferential connectivity toperturbagen instances tested in BJ fibroblasts. In other words, among the top ranked instances (i.e., with high connectivity scores) resulting from queries with photo-aging signatures BJ fibroblast instances were strongly over-represented. This effect was most dramatic when the genes up-regulated in photoaged skin were used as the query signatures. A similar result, but less strong, was obtained with the intrinsic aging signatures (e.g., Example 3). A summary of the results of comparing a plurality of instances with the Photo-aging 600 signature is shown in Table 1. These results are completely unpredicted and surprising considering that: i) the gene signatures derived from full thickness biopsies comprising a variety of cell types expected to contribute to the skin aging phenotype, and ii) skin aging is a complex multi-factorial condition involving changes in most of the tissues and structures of skin,

TABLE 1

Distribution of fibroblast (BJ and keratinocyte (tKC) instances in the top ranked instances from a C-map query with the Photo-aging 600 signature[1]

| | Chemical instances tested in each cell type | | | | | |
|---|---|---|---|---|---|---|
| | Complete signature | | Up list [3] | | Down list [3] | |
| Rank [2] | BJ | tKC | BJ | tKC | BJ | tKC |
| 1-100 | 79 | 21 | 100 | 0 | 36 | 64 |
| 101-200 | 60 | 40 | 100 | 0 | 36 | 64 |
| 201-300 | 57 | 43 | 100 | 0 | 41 | 59 |
| 301-400 | 51 | 49 | 96 | 4 | 34 | 66 |
| 401-500 | 38 | 62 | 85 | 15 | 15 | 72 |

[1]This signature comprises the 300 most statistically significant up-regulated and the 300 most significant down-regulated Affymetrix probe sets in the older arm to younger arm comparison described in Example 2, above.

[2] Instances were ranked from the most negatively scoring to most positive (i.e., 1 was the most negatively scoring instance). Chemicals scoring negatively are predicted to have beneficial effects on photo-aging.

[3] The up list results are from querying a database of instances with only up-regulated probe sets in the gene expression signature. Similarly, the down list results are from querying with a gene expression signature comprising only probe sets that are down-regulated.

Among the top 300 ranked instances linking to the complete photo-aging signature, 196 (65.3%) were with respect to BJ fibroblasts and only 34.7% were with respect to keratinocytes. This was more than a 2-fold over-representation of fibroblasts, since they comprised only 31% of the instances in the database. The preferential connectivity of fibroblasts to the photo-aging signature was much more dramatic when only the up list was used for the query. Remarkably, in that case all of the top 300 instances were in fibroblasts. The up signature contribution accounted for the preferential connectivity of fibroblasts to the complete photo-aging signature, because querying with the down signature alone gave a distribution of top scoring instances more proportional to the percentages of the two cell lines instances in the database. Similar results were obtained with the Photo-aging P200 and P400 signatures described in Example 2. Overall, the strong preferential connectivity of fibroblast instances to the photo-aging signatures is surprising because keratinocytes are expected to contribute to the photo-aging phenotype and all of the materials tested in BJ fibroblasts were also tested in keratinocytes (i.e., the effect is not due to any chemical specificity).

A similar but subtly different pattern was observed when the provided database was queried with intrinsic aging gene expression signatures. Table 2 shows results obtained with the Intrinsic Aging 600 signature (Example 3). Again there was an over-representation of fibroblasts among the top ranked instances with the complete signature, and this effect was due to the up-regulated probe sets in the signature, but the effect was not as strong as with the photo-aging signatures. Furthermore, the top ranking instances connecting to the down list showed some over-representation of keratinocytes relative to their proportion of the samples tested (Table 2).

TABLE 2

Distribution of fibroblast (BJ) and keratinocyte (tKC) instances in the top ranked instances from a C-map query with the Intrinsic Aging 600 signature.[1]

| | Chemical instances tested in each cell type | | | | | |
|---|---|---|---|---|---|---|
| | Complete signature | | Up list [3] | | Down list [3] | |
| Rank [2] | BJ | tKC | BJ | tKC | BJ | tKC |
| 1-100 | 68 | 32 | 95 | 5 | 13 | 87 |
| 101-200 | 55 | 45 | 84 | 16 | 17 | 83 |
| 201-300 | 38 | 62 | 72 | 28 | 17 | 83 |
| 301-400 | 37 | 63 | 67 | 33 | 21 | 79 |
| 401-500 | 31 | 69 | 57 | 43 | 26 | 74 |

[1] This signature comprises the 300 most statistically significant up- and 300 most significant down-regulated Affymetrix probe sets in the older buttock to younger buttock comparison in the clinical study described in Example 3.
[2] Instances were ranked as in Table 1.
[3] The up list results are from querying the C-Map database with only the up-regulated probe sets in the signature. Similarly, the down list results are from querying only with the down list.

Unexpectedly, the gene expression signatures generated from clinical samples of photo-aged skin show very strong preferential connectivity to chemical instances tested in dermal fibroblasts compared to epidermal keratinocytes. Furthermore, this preferential connectivity was observed with signatures generated from gene expression profiling done on RNA extracted from full thickness biopsies of skin, which comprise a composite sample of all of the cell types within the complex structure of skin. Analysis of the biological processes associated with the genes differentially expressed in photo-aged skin indicated that many of the processes were related to the dermis and fibroblasts including wound healing (see Theme Analysis, Example 5). These results support the hypothesis that the dominant gene expression changes in photo-aged skin occur in dermal fibroblasts. Furthermore, in clinical testing statistically significant anti-wrinkle results were obtained with two botanical extracts predicted to have skin anti-aging activity based on C-Map queries of fibroblast instances (e.g. Examples 6 and 7). In contrast, the keratinocytes instances of these materials did not predict their anti-aging activities.

These differences between the photo-aging and intrinsic aging signatures may be accounted for by the fact that they represent overlapping but different biological changes in aging skin (see Theme Analysis, Example 5). Photo-aging is due to a combination of the effects of UV radiation exposure and intrinsic factors, while intrinsic aging lacks the solar/UV component. Fewer than 20% of the genes in the photo-aging and intrinsic aging signatures were observed to be in common. These results point to the value of using both photo-aging and intrinsic aging signatures when applying C-map to identify cosmetic agents to improve aging skin, because the signatures will allow detection of materials that affect different aspects of the complex aging process.

The under-representation of telomerized keratinocytes in the top ranked C-map instances with queries using the complete photo-aging and intrinsic aging gene expression signatures was not due to a lack of responsiveness of the cells under the conditions of testing. Table 3 sets forth gene expression outlier numbers for 493 chemicals that were tested in both BJ fibroblasts and telomerized keratinocytes using the same stock solutions. Outlier numbers were calculated for each singleton C-map instance and are a measure of the number of probe sets regulated by treatment. In this probe set-by-probe set analysis, the 6 vehicle control samples in a C-map batch are used to form a prediction interval for each probe set, and then for each chemical instance in the batch the probe sets falling outside the interval are counted. This statistic is used because chemical replication is usually done in different C-map batches due to batch effects on the scoring.

TABLE 3

Gene expression outlier numbers for 493 materials tested in both BJ fibroblasts and telomerized keratinocytes.[1]

| | Number of C-MAP instances | |
|---|---|---|
| Range of outliers | BJ fibroblasts | Telomerized-keratinocytes |
| ≥2000 | 123 | 245 |
| 1000-1999 | 711 | 725 |
| <1000 | 292 | 234 |
| Totals: | 1126 | 1204 |

[1]Materials from the same stock tubes were tested in both types of cells. Outlier numbers were calculated for each singleton C-map instance and are a measure of the number of probe sets regulated by treatment. In this probe set-by-probe set analysis, the 6 vehicle control samples in a C-map batch are used to form a prediction interval for each probe set, and then for each chemical instance in the batch the probe sets falling outside the interval are counted. This statistic is used because chemical replication is usually done in different C-map batches due to batch effects on the scoring.

Figure 9:
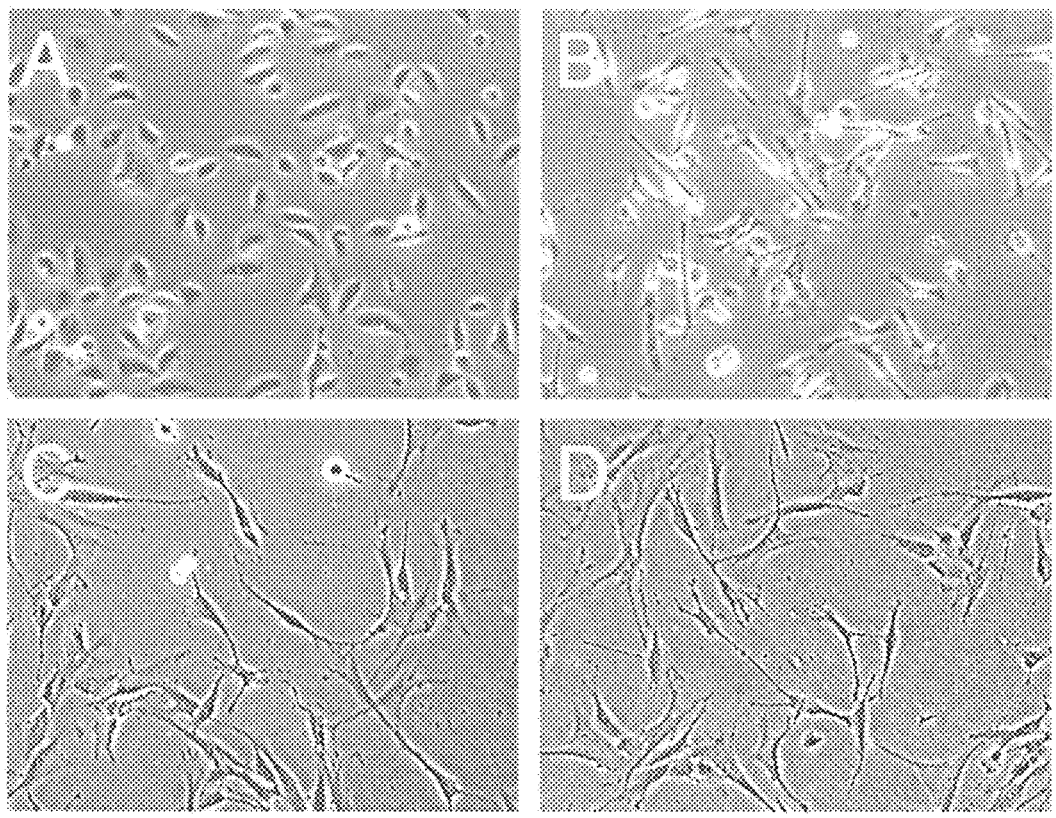
FIG. 9 illustrates morphology of A: telomerized-keratinocytes treated with 0.1% DMSO for 6 hr (vehicle control); B: telomerized-keratinocytes treated with 10 µM all-trans-retinoic acid (tRA) in DMSO for 6 hr; C: BJ fibroblasts treated with 0.1% DMSO for 6 hr (vehicle control); and D: BJ fibroblasts treated with 10 µM tRA in DMSO for 6 hr; wherein the control keratinocytes are observed to have a cobblestone-like morphology, the control fibroblasts are observed to have a spindly morphology; and wherein treatment with 10 µM tRA caused dramatic morphologic changes in the keratinocytes (B compared to A) but had no apparent morphologic effect on the fibroblasts (D compared to C).

Based on outlier numbers, the keratinocytes tended to be more responsive to treatment than fibroblasts and there were about twice as many keratinocyte instances with high outlier numbers (≥2,000) compared to those with fibroblasts. Additional indications of cellular responsiveness to treatment are morphologic changes. Altered morphology in telomerized keratinocytes treated with various chemicals has been observed. In contrast, morphologic changes in BJ fibroblasts have rarely been observed under the same conditions. A fairly dramatic comparative example is shown in FIG. 9, which documents the morphology of cells treated with 10 μM all-trans-retinoic acid (tRA). This treatment caused marked morphologic changes in the keratinocytes, but had no apparent effect on the morphology of the fibroblasts. Therefore it is surprising that the more responsive keratinocytes were less predictive than fibroblasts with respect to photo-aging.

Example 5

Theme Analysis of Age-Related Gene Expression Signatures

Theme analysis was used as a tool to understand better the results obtained using BJ fibroblasts instances. Theme analysis is a statistical analysis-based method for detecting biological patterns in gene expression profiling data. The method uses an ontology of controlled vocabulary terms developed by the Gene Ontology (GO) Consortium [Ashburner, M. et al. (2000) Gene ontology: tool for the unification of biology. The Gene Ontology Consortium. Nat Genet, 25, 25-29] that describes the biological processes, molecular functions and cellular components associated with gene products. Analysis involves statistical comparison of a regulated list of genes and a larger reference list of all the expressed genes, to determine if genes annotated to specific GO terms are significantly enriched in the regulated list. This analysis reveals biological patterns when multiple genes associated with a given GO term occur on the regulated list at a frequency greater than expected by chance. Such analysis was performed using Theme Extractor proprietary software and an algorithm that calculates the p value for each ontology term. Data were analyzed for statistical significance by the Fisher's exact test. The approach used here and statistical methods are very similar to Gene Set Enrichment Analysis, which has been described in the literature [Subramanian, A. et al. (2005) Gene set enrichment analysis: a knowledge-based approach for interpreting genome-wide expression profiles. *Proc. Natl. Acad Sci U.S.A*, 102, 15545-15550].

Table 4 shows GO Biological Process terms that are significantly enriched in the comparison of the older arm to younger arm (photo-aging) results from the clinical gene expression study described in Example 3. This involved the analysis of approximately 12,500 expressed genes. Only the most highly significant themes are shown ($p \leq 1 \times 10^{-4}$), and the theme analysis was done separately for the up- and down-regulated genes. The level of indentation in the terms column generally indicates the level in the GO hierarchy and parent/child relationships between terms. In other words, indented terms often are related to the term above them and describe a more specific process. The numbers of asterisks indicate the p value ranges for each term.

TABLE 4

Theme analysis of genes regulated in photo-aging.

| Gene Ontology Biological Process Terms | Old Arm to Young Arm Comparison[1] | | Terms related to dermis |
|---|---|---|---|
| | Up | Down | |
| ...GO: 0006956 complement activation | * | | |
| .GO: 0032501 multicellular organismal process | **** | | |
| ..GO: 0007275 multicellular organismal development | *** | | |
| ...GO: 0035295 tube development | * | | |
| ....GO: 0030323 respiratory tube development | * | | |
| .....GO: 0048754 branching morphogenesis of a tube | * | | |
| ...GO: 0048731 system development | *** | | |
| ....GO: 0048513 organ development | * | | |
| .....GO: 0048568 embryonic organ development | * | | |
| .....GO: 0009887 organ morphogenesis | * | | |
| .....GO: 0009888 tissue development | * | | |
| ....GO: 0007399 nervous system development | ** | | |
| ....GO: 0001501 skeletal system development | ** | | X |
| .....GO: 0048706 embryonic skeletal system development | * | | X |
| ...GO: 0048736 appendage development | ** | | X |
| ....GO: 0035107 appendage morphogenesis | * | | X |
| ....GO: 0060173 limb development | * | | X |
| ...GO: 0007389 pattern specification process | * | | |
| .GO: 0032502 developmental process | *** | | |
| ..GO: 0048856 anatomical structure development | *** | | |
| ...GO: 0009653 anatomical structure morphogenesis | *** | | |
| ...GO: 0016477 cell migration | * | | |
| ......GO: 0002541 activation of plasma proteins involved in acute inflammat... | * | | |
| ...GO: 0009611 response to wounding | **** | | X |
| ....GO: 0042060 wound healing | **** | | X |
| ..GO: 0009605 response to external stimulus | **** | | |
| ...GO: 0019222 regulation of metabolic process | | * | |
| .......GO: 0045941 positive regulation of transcription | | * | |
| ........GO: 0045893 positive regulation of transcription, DNA-dependent | | * | |
| ........GO: 0045944 positive regulation of transcription from RNA polym... | | * | |
| .......GO: 0006355 regulation of transcription, DNA-dependent | | * | |
| ........GO: 0045892 negative regulation of transcription, DNA-dependent | | * | |
| .........GO: 0000122 negative regulation of transcription from RNA polym... | | ** | |
| ........GO: 0006357 regulation of transcription from RNA polymerase II pr... | | ** | |
| .......GO: 0016481 negative regulation of transcription | | * | |
| .......GO: 0051253 negative regulation of RNA metabolic process | | * | |
| ......GO: 0051252 regulation of RNA metabolic process | | * | |
| .......GO: 0051254 positive regulation of RNA metabolic process | | * | |
| ......GO: 0045935 positive regulation of nucleobase, nucleoside, nucleotide... | | ** | |
| .....GO: 0031324 negative regulation of cellular metabolic process | | * | |
| ......GO: 0031327 negative regulation of cellular biosynthetic process | | ** | |
| .....GO: 0031325 positive regulation of cellular metabolic process | | * | |
| ......GO: 0031328 positive regulation of cellular biosynthetic process | | * | |
| .....GO: 0051173 positive regulation of nitrogen compound metabolic process | | ** | |
| ....GO: 0060255 regulation of macromolecule metabolic process | | * | |

TABLE 4-continued

| | | |
|---|---|---|
| ......GO: 0010628 positive regulation of gene expression | * | |
| ......GO: 0010629 negative regulation of gene expression | * | |
| ......GO: 0010557 positive regulation of macromolecule biosynthetic process | * | |
| ......GO: 0010558 negative regulation of macromolecule biosynthetic process | * | |
| .....GO: 0010604 positive regulation of macromolecule metabolic process | * | |
| .....GO: 0010605 negative regulation of macromolecule metabolic process | * | |
| .....GO: 0009890 negative regulation of biosynthetic process | ** | |
| .....GO: 0009891 positive regulation of biosynthetic process | * | |
| ....GO: 0009892 negative regulation of metabolic process | * | |
| ....GO: 0048522 positive regulation of cellular process | * | |
| ......GO: 0002053 positive regulation of mesenchymal cell proliferation | * | X |
| ....GO: 0048634 regulation of muscle organ development | * | X |
| .....GO: 0016202 regulation of striated muscle tissue development | * | X |
| .....GO: 0010464 regulation of mesenchymal cell proliferation | ** | X |
| ....GO: 0007165 signal transduction | * | * |
| .....GO: 0009966 regulation of signal transduction | * | |
| ..GO: 0043062 extracellular structure organization | * | |
| ...GO: 0030198 extracellular matrix organization | ** | X |
| .....GO: 0006350 transcription | | * |
| ..GO: 0006928 cellular component movement | * | |
| ....GO: 0006325 chromatin organization | | * |
| .....GO: 0016568 chromatin modification | | ** |
| ..GO: 0007154 cell communication | * | |
| .....GO: 0016485 protein processing | * | |
| ......GO: 0051605 protein maturation by peptide bond cleavage | * | |

[1]Statistical significance is as follows.
P-Value Legend

| | | | |
|---|---|---|---|
| 1.00E−4< | p | | |
| 1.00E−5< | p | <=1.00E−4 | * |
| 1.00E−6< | p | <=1.00E−5 | ** |
| 1.00E−7< | p | <=1.00E−6 | *** |
| | p | <=1.00E−7 | **** |

This analysis revealed that up- and down-regulated genes in photo-aging were associated with quite distinct biological processes. A number of biological processes closely associated with fibroblasts and connective tissue were up-regulated in photo-aging. It is notable that the Gene Ontology terms "response to wounding" and "wound healing" were among the most statistically significant terms ($p \leq 1 \times 10^{-7}$) for the up-regulated gene list. Other terms clearly associated with fibroblasts or mesenchymal cells are marked in Table 4 and these all were significant for the up list. Most of these other terms associated with the up-regulated list relate to developmental processes in which mesenchymal cells play important roles. The genes down-regulated in photo-aging were associated with more general processes such as gene transcription and various aspects of metabolism and signal transduction that relate to various cell types.

The Photo-aging 600 signature gene lists (see Example 2) were also subject to theme analysis (not shown), which revealed a pattern of significant terms quite similar to that obtained with the entire photo-aging data set. The up-regulated gene list contains genes involved in biological processes closely associated with fibroblasts or mesenchymal cells. Again among the most significant terms for the up list included "response to wounding" and "wound healing" ($P \leq 1 \times 10^{-5}$). The results of these theme analyses provide a clear rationale for the specific linkage of fibroblasts to the photo-aging up-regulated gene expression signature and the strong linkage to the overall signature.photo-aging It appears that the dominant processes that are up-regulated in photo-aging involve the dermis and fibroblasts. Overall, the photo-aging gene signatures reflect this dominant biology observed in the gene expression profiling of the photo-aging skin condition.

Theme analysis was also performed on the genes regulated in intrinsic aging, which involved approximately 12,500 expressed genes. Table 5 shows GO Biological Process terms that are significantly enriched in the comparison of the older buttock to younger buttock (intrinsic aging) from the clinical gene expression study described in Example 3. Similarly with respect to Table 4, only the most highly significant themes are shown ($p \leq 1 \times 10^{-4}$) to keep the size of this table manageable.

TABLE 5

Theme analysis of genes regulated in intrinsic aging

| | Old Buttock to Young Buttock Comparison[1] | | Terms related to epi- |
|---|---|---|---|
| Gene Ontology Biological Process Terms | Up | Down | dermis |
| .GO: 0032501 multicellular organismal process | * | | |
| ...GO: 0022600 digestive system process | | * | |
| ...GO: 0003012 muscle system process | * | | |
| ..GO: 0007275 multicellular organismal development | * | | |
| ...GO: 0048731 system development | *** | | |
| ....GO: 0048513 organ development | *** | | |
| ......GO: 0007398 ectoderm development | | * | X |
| ......GO: 0021846 cell proliferation in forebrain | | * | |

TABLE 5-continued

Theme analysis of genes regulated in intrinsic aging

| Gene Ontology Biological Process Terms | Old Buttock to Young Buttock Comparison[1] | | Terms related to epi-dermis |
|---|---|---|---|
| | Up | Down | |
| ....GO: 0007399 nervous system development | | * | |
| .....GO: 0007417 central nervous system development | | ** | |
| ..GO: 0007586 digestion | | * | |
| ..GO: 0001503 ossification | * | | |
| .GO: 0032502 developmental process | * | | |
| ..GO: 0048856 anatomical structure development | ** | | |
| ...GO: 0060021 palate development | * | | |
| ...GO: 0061061 muscle structure development | * | | |
| .....GO: 0043434 response to peptide hormone stimulus | | ** | |
| ....GO: 0042127 regulation of cell proliferation | * | | |
| ...GO: 0042180 cellular ketone metabolic process | | * | |
| ....GO: 0043436 oxoacid metabolic process | | * | X |
| .....GO: 0019752 carboxylic acid metabolic process | | * | X |
| .......GO: 0006631 fatty acid metabolic process | | * | X |
| ........GO: 0006633 fatty acid biosynthetic process | | * | X |
| ......GO: 0046394 carboxylic acid biosynthetic process | | * | X |
| ....GO: 0042438 melanin biosynthetic process | | * | |
| ....GO: 0051188 cofactor biosynthetic process | | * | |
| ....GO: 0016053 organic acid biosynthetic process | | * | X |
| ...GO: 0044255 cellular lipid metabolic process | | *** | X |
| ...GO: 0051186 cofactor metabolic process | | ** | |
| ....GO: 0006732 coenzyme metabolic process | | * | |
| ...GO: 0006082 organic acid metabolic process | | * | X |
| ..GO: 0019748 secondary metabolic process | | * | |
| ...GO: 0006582 melanin metabolic process | | * | X |
| ...GO: 0006629 lipid metabolic process | | **** | X |
| ....GO: 0008202 steroid metabolic process | | * | X |
| .....GO: 0006694 steroid biosynthetic process | | ** | X |
| ......GO: 0016126 sterol biosynthetic process | | ** | X |
| .......GO: 0006695 cholesterol biosynthetic process | | ** | X |
| .....GO: 0016125 sterol metabolic process | | * | X |
| ....GO: 0008610 lipid biosynthetic process | | **** | X |
| ..GO: 0044281 small molecule metabolic process | | **** | |
| ...GO: 0044283 small molecule biosynthetic process | | * | |
| ...GO: 0006066 alcohol metabolic process | | * | |
| ..GO: 0055114 oxidation reduction | | ** | |

[1]Statistical significance is as described in Table 4.

The theme analysis of the genes regulated in intrinsic aging, like that for photo-aging, revealed that the up- and down-regulated genes were associated with very different processes. The down-regulated genes in intrinsic skin aging were associated with a number of processes related to the epidermis and keratinocytes. Most dominant were terms related to lipid biosynthetic pathways that are involved in the synthesis of lipids important in epidermal barrier function. A more specific term related to epithelial biology, "ectoderm development," was associated with the down-regulated genes. The related term "epidermal development" (p<0.001) was not included in the table because it did not make the p value cutoff, but it was also associated with the down-regulated genes. Terms related to regulation of pigmentation (melanogenesis), which is an epidermal function, were also significant for the down list analysis. As seen in the analysis of photo-aging, up-regulated themes included various developmental processes related to mesenchymal cells. The appearance of terms such as "ossification," which may seem irrelevant to skin, was due to the fact that various regulatory pathways and related genes are involved in a number of processes associated with cell lineages. Bone matrix cells are of mesenchymal origin. The term "regulation of mesenchymal cell proliferation" (highly significant in the photo-aging analysis) was not included in the table because it did not make the p value cutoff, but was significant at p<0.001 for the up list in intrinsic aging.

The Intrinsic Aging 600 signature gene lists (described in Example 3 and defined as the top 300 up- and down-regulated genes set forth in Tables A and B) were also subjected to theme analysis (not shown), which revealed a pattern of significant terms similar to that obtained with the entire intrinsic aging data set. The up-regulated gene list contains genes involved in biological processes associated with fibroblasts or mesenchymal cells, and the down-regulated list contained genes more closely associated with epidermal processes and keratinocytes. The results of these theme analyses suggest a rationale for the strong connectivity of fibroblasts to the intrinsic aging up-regulated gene expression signature and their preferential linkage to the overall signature, as well as the preferential connectivity of keratinocyte instances to the down-regulated gene expression signature. Overall, the intrinsic aging signatures reflect the biology in intrinsic aging.

The biological theme analyses performed on the genes regulated in photo-aging and intrinsic aging demonstrate differences in the dominant biology in these two aspects of skin aging. The major differences related to an apparently greater down-regulation of processes associated with keratinocyte differentiation in intrinsic aging. These analyses further support the value of using signatures for both photo-aging and intrinsic aging in querying the C-map database to identify cosmetic materials to treat aging skin. These analyses also further support the non-intuitive finding that fibroblasts cell lines are more useful than keratinocyte cell lines for identifying cosmetic agents to improve photo-aged skin. The studies described herein also demonstrate that cell type-specific signals can be detected from full thickness biopsies using the C-map method and system.

Example 6

Connectivity Map Results for Artichoke Leaf Extract and Carob Seed Extract

In this example, 20 materials that were candidates for an anti-aging facial benefit study were tested in fibroblasts and keratinocytes. A microarray analysis was conducted for each sample compound and ordered lists of the probe set IDs were stored as instances in a database. Photo-aging and intrinsic aging gene expression signatures were compared against the instances and connectivity scores were derived.

Of the 20 candidates screened, 2 showed consistent connections to the photo-aging gene expression signatures when tested in BJ fibroblasts. The detailed results for these materials, artichoke leaf extract and carob seed extract, are shown in Table 6. Since both intrinsic aging and photo-aging are considered adverse conditions, it is preferential to find materials that tend to reverse one or both of the gene expression signatures. Such materials will have negative connectivity score, and the more negative the score the stronger the negative connection. It can be seen in Table 6 that all fibroblast instances of artichoke leaf extract consistently linked negatively to the 3 photo-aging gene expression signatures. Artichoke leaf extract also consistently scored negatively with the intrinsic aging signatures when tested in fibroblasts, but the scores were weaker and there were some null or zero scores. Null scores are not considered inconsistent with other scores all showing the same directionality. When tested in keratinocytes, artichoke leaf extract showed generally weak positive connections to both the photo-aging and intrinsic aging gene expression signatures. Therefore, the testing in fibroblasts and keratinocytes gave inconsistent results. Similarly, carob seed extract fibroblast instances showed a pattern of negative connections to the photo-aging gene expression signatures and inconsistent results were obtained with keratiocyte instances with both sets of gene signatures.

Present calls, wherein the microarray analysis of the BJ fibroblast cells was derived from data from 30 control and chemically-treated cultures. This filter was added so that the modified gene expression signature would only contain probes complementary to genes actually expressed in the fibroblasts. Additionally, the probes used in the modified gene expression signature were identified using the following filters.

TABLE 6

C-MAP scores for two cosmetic supplier materials, Biobenefity™ and Glyco-repair™, tested in fibroblasts and keratinocytes.

| GeneChip ID | Material [1] | Cell Line Utilized for Instance Data | Intrinsic Aging Clinical Signatures | | | Photo-aging Clinical Signatures | | |
|---|---|---|---|---|---|---|---|---|
| | | | Intrinsic 200 | Intrinsic 400 | Intrinsic 600 | Photo-aging 200 | Photo-aging 400 | Photo-aging 600 |
| CMP_62_13 | Artichoke | BJ | −0.403 | 0 | −0.333 | −0.551 | −0.553 | −0.547 |
| CMP_62_14 | Leaf | fibroblasts | −0.211 | −0.198 | −0.235 | −0.251 | −0.298 | −0.299 |
| CMP_65_51 | Extract[2] | | 0 | −0.222 | 0 | −0.31 | −0.264 | −0.295 |
| CMP_61_13 | | Telomerized- | 0 | 0 | 0 | 0 | 0 | 0.19 |
| CMP_61_14 | | keratinocytes | 0.401 | 0.346 | 0.316 | 0.293 | 0.268 | 0.284 |
| CMP_68A_27 | | | −0.251 | 0 | 0.137 | 0.209 | 0.156 | 0.149 |
| CMP_62_23 | Carob | BJ | 0 | 0 | 0 | −0.342 | −0.288 | −0.325 |
| CMP_62_24 | Seed | fibroblasts | 0 | 0 | 0 | −0.41 | −0.327 | −0.325 |
| CMP_65_55 | Extract[3] | | 0 | 0 | 0.151 | 0 | 0 | 0 |
| CMP_61_23 | | Telomerized- | −0.321 | −0.286 | −0.248 | −0.44 | −0.438 | −0.404 |
| CMP_61_24 | | keratinocytes | 0.27 | 0.25 | 0.226 | −0.374 | −0.349 | 0 |
| CMP_68A_31 | | | 0.287 | 0.263 | 0.268 | 0.347 | 0.348 | 0.346 |

[1] Test compositions were prepared using a concentration of 0.01% of one of artichoke leaf extract or carob seed extract.
[2] One example of Artichoke leaf extract is available from Ichimaru Pharcos, Japan under the tradename Biobenifity™
[3] One example of carob seed extract is available from Silab, France under the tradename Glyco-Repair™

In view of the discovery that there is a strong preferential linkage of the skin aging gene expression signatures to instances derived from fibroblasts, additional gene expression signatures optimized for the fibroblast linkage were also generated to screen the cosmetic materials. Only the photo-aging data from the aging skin genomics study in Example 2 were used because the fibroblast linkage to the photo-aging gene expression signature was stronger than that to intrinsic aging gene expression signature. The modified gene expression signatures were generated similarly to the photo-aging signatures in Example 3, except that the microarray probe sets were also filtered for genes selected from a microarray analysis of BJ fibroblast cells that had ≥10%

(i) "Signature 1" Filtered on log t-test rank; best ranked 100 up-regulated and 100 down-regulated probe sets in the arm old to young comparison.

(ii) "Signature 2" Filtered on log t-test rank; best ranked 150 up-regulated and 150 down-regulated probe sets in the arm old to young comparison.

(iii) "Signature 3" (identifiers set forth in Table I) Filtered on log t-test rank; best ranked 200 up-regulated and 200 down-regulated probe sets in the arm old to young comparison.

TABLE 7

Connectivity scores derived from a comparison of artichoke leaf extract and carob seed extract instances tested in fibroblast cells compared to the fibroblast-optimized photo-aging signatures.

| | | | Photo-aging signatures optimized for fibroblasts | | |
|---|---|---|---|---|---|
| GeneChip ID | Material[1] | Cell Line | Signature 1 | Signature 2 | Signature 3 |
| CMP_62_13 | Artichoke leaf | BJ | −0.721 | −0.707 | −0.684 |
| CMP_62_14 | extract | fibroblasts | −0.341 | −0.366 | −0.375 |
| CMP_65_51 | | | −0.417 | −0.38 | −0.365 |
| CMP_62_23 | Carob seed | BJ | −0.482 | −0.43 | −0.415 |
| CMP_62_24 | extract | fibroblasts | −0.48 | −0.41 | −0.416 |
| CMP_65_55 | | | 0 | 0 | 0 |

[1] The C-map instances are the same as in Table 6. Only results with fibroblasts are shown.

The results set forth in Table 7 are similar to those for the photo-aging signatures shown in Table 6 except that the scores are stronger.

An overall weighting of the C-map scores was used to determine whether the materials tested were considered hits against the gene expression signatures. For each signature in a category (e.g. photo-aging or intrinsic aging), the hits were identified and given a weight using the criteria in Table 8. The desired directionality of the scores depends on whether the analysis is intended to identify materials that will ameliorate a condition like photo-aging (negative scores) or that are similar to a known benefit agent (positive scores). This heuristic approach was applied because of the limited number of replicates available for the materials in the C-map database.

TABLE 8

| Weight | Criteria |
|---|---|
| 3 | At least 2 instances in the top 5% of all C-map instances[1] based on C-map score, all instances with correct directionality or null. Non-null instances >50%. |
| 2 | At least 1 instance in the top 5% of all C-map instances based on C-map score, all instances with correct directionality or null. Non-null instances >50%. |
| 2 | At least 2 instances in the top 10% of all C-map instances based on C-map score, all instances with correct directionality or null. Non-null instances >50%. |
| 1 | 1 instance in the top 5% of all C-map instances, all instances with correct directionality or null. Non-null instances ≥40% AND ≤50%.. |

[1]There were more than 4000 chemical instances in the C-map database when these analyses were done.

The average weight was calculated for each set of signatures (e.g. the 3 photo-aging signatures described in Example 2 and derived from Tables C and D). Materials were considered a hit if their average weights across signatures were as described in Table 9.

TABLE 9

| Weighting of hits | Average hit weights |
|---|---|
| Strong hit | value = 3 |
| Hit | 2 ≤ value < 3 |
| Weak hit | 1 < value < 2 |
| Weak linkage | 0 < value ≤ 1 |

The results of the weighted analysis for artichoke leaf extract and carob seed extract are shown in Table 10. Based on the average hit weights artichoke leaf extract was considered an overall negative hit against the photo-aging signatures and a weak negative hit against the intrinsic aging signatures when tested in fibroblasts. Carob seed extract was a weak negative hit against the photo-aging signatures optimized for fibroblasts. Considering the strong preferential linkage of the photo-aging signatures to instances derived from fibroblasts (described above), the keratinocyte data were discounted and only the fibroblast data were used as part of the weight of evidence to determine whether artichoke leaf extract and carob seed extract should be advanced to in vivo testing.

TABLE 10

Weighting of the C-map scores from Table 6 and Table 7 to determine hits.

| | | Average hit weights | | |
|---|---|---|---|---|
| Material | Cell Line | Intrinsic Aging Signatures (I200, I400, I600) | Photo-aging Signatures (P200, P400, P600) | Fibroblast Optimized Photo-aging Signatures (Signatures 1-3) |
| Artichoke leaf extract | BJ fibroblasts | 1.33 | 2 | 2 |
| | Telomerized-keratinocytes | 0 | 0 | 0 |
| Carob seed extract | BJ fibroblasts | 0 | 0 | 1.33 |
| | Telomerized-keratinocytes | 0 | 0 | 0 |

Example 7

In vitro and In vivo Results for Artichoke Leaf Extract and Carob Seed Extract

C-map is a hypothesis-generating tool whose predictiveness for identifying agents that can improve aging skin should be validated through clinical testing. Artichoke leaf extract and carob seed extract were subjected to in vitro testing to establish a weight of evidence before submitting them for clinical tests. Skin equivalent cultures were treated with the materials as described below and assayed for endpoints related to cosmetic benefits including: procollagen, hyaluronic acid, fibronectin, and inhibition of matrix metalloprotease 1 (MMP1) activity.

In Vitro Testing Procedures:

Human skin equivalent cultures (EFT-400 Full-Thickness Skin Model, MatTek Corporation, Ashland Mass.) were equilibrated overnight at 37° C. and 5% $CO_2$. Cultures were treated topically with 40 µl of test material for 24 hours. The test materials evaluated were aqueous solutions of 3.0% of a commercial preparation of hydrolyzed carob seed extract or 3.5% of a commercial preparation of artichoke leaf extract. Control cultures were treated with water vehicle alone. After treatment with test material, the cultures were rinsed with PBS. A 5-mm punch biopsy sample was taken for procollagen and hyaluronic acid measurements and the remaining quantities of each culture were used for cell viability (MTT) analysis.

Cultures to be tested for cell viability were transferred to new six-well plates containing 2 ml of MTT solution (MTT kit, MatTek Corporation) in each well and incubated for 3 hours. Cultures were then removed from wells, blotted dry, and transferred to new six-well plates containing 3 ml of extraction solution in each well. One ml of extraction solution was added topically to each culture, and the plates were placed on a shaker for 2 hours at room temperature. An aliquot (200 µl) of extraction solution was removed from each culture well, transferred to a 96-well flat bottom plate, and read at $A_{570}$.

Culture samples for procollagen and hyaluronic acid analysis were incubated with 1 ml of mild protein extraction reagent (T-per, Pierce Protein Research Products, Thermo Fisher Scientific Inc., Rockford, Ill.), then homogenized with a mixer mill (Model MM 300, Qiagen Inc., Valencia, Calif.) for 6 minutes. Samples were then centrifuged at 10,000 rpm for 15 minutes at 4° C. and the soluble fractions collected. Supernatants were analyzed with a Micro BCA Protein Assay Kit (Pierce Protein Research Products, Thermo Fisher Scientific Inc., Rockford, Ill.) to quantify protein concentrations. For analysis of procollagen 1, supernatant samples were diluted 1:5 in assay buffer and analyzed with a commercially available ELISA kit (Takara Bio Inc., Shiga, Japan). For hyaluronic acid analysis, supernatant samples were diluted 1:300 in assay buffer and analyzed with a commercially available ELISA kit (Corgenix, Broomfield Colo.). Procollagen and hyaluronic acid were normalized to protein levels for each culture, and expressed as a % of the vehicle control. Statistical comparisons to vehicle control were made using the Students t-test.

In Vitro Testing Results:

TABLE 11

In vitro Skin Biomarker Responses

| Compound | Level (%) | Hyaluronic Acid (% control) | Procollagen (% control) | Other (% control) |
|---|---|---|---|---|
| Carob Seed Extract | 3.0 | 139* | 354* | — |
| Artichoke Leaf Extract | 3.5 | 160* | 270* | MMP-1: 64* |

*indicates $p < 0.05$;
nc = no change vs Control

These results indicate that human skin cultures treated with 3.0% of a commercial preparation of hydrolyzed carob seed extract significantly ($p<0.05$) increased expression of procollagen (the precursor of dermal matrix collagens) and hyaluronic acid (a matrix component that binds water and hydrates the skin). Cultures treated with 3.5% of a commercial preparation of artichoke leaf extract produced significantly increased expression of procollagen and hyaluronic acid, and also significantly reduced MMP-1 expression (an enzyme increased in skin aging and inflammation that damages dermal matrix).

In Vivo Testing Procedures

The study design was a 13-week, randomized, double-blinded, vehicle controlled, split-face study to evaluate fine lines and wrinkles in 40 to 65 year old women, Fitzpatrick skin type I to III, with moderate to moderately-severe photo-aged facial skin. The duration of the study included 1-week preconditioning with vehicle product, followed by 12 weeks of test product application to the facial skin twice each day. High density digital images of subject facial skin were captured with a Fuji S2 Pro digital SLR camera with a 60 mm Nikon lens. Images were taken at baseline, 4, 8 and 12 weeks. Coded images were evaluated on a 0 to 8 grading scale by expert graders to determine the degree of change in eye area fine lines and wrinkles at 4, 8 or 12 weeks as compared to the matching baseline image for each subject.

The test products used by the panelists contained a commercial preparation of 3.0% hydrolyzed carob seed extract or 3.5% artichoke leaf extract, each prepared in an oil-in-water formulation. The control was the oil-in-water formulation alone.

In Vivo Test Results:

TABLE 12

Eye Area Fine Lines & Wrinkle Grades at 4, 8 and 12 Weeks of Test Product Use

| | | 8 Weeks | | | 12 Weeks | | |
|---|---|---|---|---|---|---|---|
| Facial Product | Level (%) | FLW Grade | Statistical Grouping | p value vs Vehicle | FLW Grade | Statistical Grouping | p value vs Vehicle |
| Vehicle | — | 0.137 | a | — | 0.230 | a | — |
| Carob Seed extract | 3.0% | 0.741 | bc | 0.0302 | 0.799 | bc | 0.0213 |
| Artichoke Leaf extract | 3.5% | 0.503 | ab | 0.1207 | 0.924 | c | 0.0059 |

These results indicate that test product containing 3.0% of a commercial preparation of carob seed extract produced a significant ($p<0.05$) improvement in eye area fine lines and wrinkles as compared to the concurrent vehicle control product at 4, 8 and 12 weeks. Test product containing 3.5% of a commercial preparation of artichoke leaf extract produced a significant improvement in eye area fine lines and wrinkles as compared to the concurrent vehicle control product at 12 weeks. Overall, the in vivo test results demonstrate the predictiveness of the methods described here to identify skin anti-aging agents.

Every document cited herein is hereby incorporated herein by reference in its entirety unless expressly excluded or otherwise limited. In particular, U.S. Ser. No. 13/402,102 and U.S. Provisional Ser. No. 61/445,315 are incorporated herein in their entirety. The citation of any document is not an admission that it is prior art with respect to any invention disclosed or claimed herein or that it alone, or in any combination with any other reference or references, teaches, suggests or discloses any such invention. Further, to the extent any meaning or definition of a term in this document conflicts with any meaning or definition of the same term in a document incorporated by reference, the meaning or definition assigned to that term in this document shall govern.

The values disclosed herein are not to be understood as being strictly limited to the exact numerical values recited. Instead, unless otherwise specified, each such value is intended to mean both the recited value and a functionally equivalent range surrounding that value.

The present invention should not be considered limited to the specific examples described herein, but rather should be understood to cover all aspects of the invention. Various modifications, equivalent processes, as well as numerous structures and devices to which the present invention may be applicable will be readily apparent to those of skill in the art. Those skilled in the art will understand that various changes may be made without departing from the scope of the invention, which is not to be considered limited to what is described in the specification.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

TABLE A

| Probe Set ID | Gene Symbol | Gene Name | Representative Public ID | p value |
|---|---|---|---|---|
| 212134_at | PHLDB1 | pleckstrin homology-like domain family B member 1 | AB014538 | 2.5989E-07 |
| 203384_s_at | GOLGA1 | golgi autoantigen golgin subfamily a 1 | NM_002077 | 8.8180E-07 |
| 203812_at | | null | AB011538 | 2.6720E-06 |
| 218418_s_at | KANK2 | KN motif and ankyrin repeat domains 2 | NM_015493 | 2.9847E-06 |
| 210619_s_at | HYAL1 | hyaluronoglucosaminidase 1 | AF173154 | 4.4879E-06 |
| 213891_s_at | TCF4 | transcription factor 4 | AI927067 | 7.1351E-06 |
| 40665_at | FMO3 | flavin containing monooxygenase 3 | M83772 | 7.4313E-06 |
| 218007_s_at | RPS27L | ribosomal protein S27-like | NM_015920 | 9.9049E-06 |
| 218986_s_at | DDX60 | DEAD (Asp-Glu-Ala-Asp) box polypeptide 60 | NM_017631 | 1.3762E-05 |
| 204112_s_at | HNMT | histamine N-methyltransferase | NM_006895 | 1.5543E-05 |
| 202510_s_at | TNFAIP2 | tumor necrosis factor alpha-induced protein 2 | NM_006291 | 1.5736E-05 |
| 205236_x_at | SOD3 | superoxide dismutase 3 extracellular | NM_003102 | 2.1085E-05 |
| 204940_at | PLN | phospholamban | NM_002667 | 2.4429E-05 |
| 204742_s_at | PDS5B | PDS5 regulator of cohesion maintenance homolog B (S. cerevisiae) | NM_015032 | 3.5542E-05 |
| 217721_at | | null | BE551361 | 3.9171E-05 |
| 61732_r_at | IFT74 | intraflagellar transport 74 homolog (Chlamydomonas) | AI610355 | 4.0031E-05 |
| 220276_at | RERGL | RERG/RAS-like | NM_024730 | 4.0141E-05 |
| 210147_at | ART3 | ADP-ribosyltransferase 3 | U47054 | 4.0793E-05 |
| 203874_s_at | SMARCA1 | SWI/SNF related matrix associated actin dependent regulator of chromatin subfamily a member 1 | NM_003069 | 4.2533E-05 |
| 218718_at | PDGFC | platelet derived growth factor C | NM_016205 | 4.7811E-05 |
| 216321_s_at | NR3C1 | nuclear receptor subfamily 3 group C member 1 (glucocorticoid receptor) | X03348 | 4.8089E-05 |
| 203083_at | THBS2 | thrombospondin 2 | NM_003247 | 4.9034E-05 |
| 212798_s_at | ANKMY2 | ankyrin repeat and MYND domain containing 2 | AK001389 | 4.9281E-05 |
| 213435_at | SATB2 | SATB homeobox 2 | AB028957 | 5.2665E-05 |
| 212796_s_at | TBC1D2B | TBC1 domain family member 2B | BF195608 | 5.3819E-05 |
| 218901_at | PLSCR4 | phospholipid scramblase 4 | NM_020353 | 5.3859E-05 |
| 208792_s_at | CLU | clusterin | M25915 | 5.5727E-05 |
| 204457_s_at | GAS1 | growth arrest-specific 1 | NM_002048 | 5.9563E-05 |
| 203906_at | IQSEC1 | IQ motif and Sec7 domain 1 | AI652645 | 6.1904E-05 |
| 204963_at | SSPN | sarcospan (Kras oncogene-associated gene) | AL136756 | 6.1925E-05 |
| 218854_at | DSE | dermatan sulfate epimerase | NM_013352 | 6.4684E-05 |
| 200771_at | LAMC1 | laminin gamma 1 (formerly LAMB2) | NM_002293 | 6.7641E-05 |
| 212195_at | IL6ST | interleukin 6 signal transducer (gp130 oncostatin M receptor) | AL049265 | 6.9132E-05 |
| 212914_at | CBX7 | chromobox homolog 7 | AV648364 | 7.2463E-05 |
| 204719_at | ABCA8 | ATP-binding cassette sub-family A (ABC1) member 8 | NM_007168 | 7.2719E-05 |
| 213397_x_at | RNASE4 | ribonuclease RNase A family 4 | AI761728 | 7.3945E-05 |
| 209613_s_at | ADH1B | alcohol dehydrogenase 1B (class I) beta polypeptide | M21692 | 7.4466E-05 |
| 205361_s_at | PFDN4 | prefoldin subunit 4 | AI718295 | 7.5317E-05 |
| 212713_at | MFAP4 | microfibrillar-associated protein 4 | R72286 | 7.6567E-05 |
| 218285_s_at | BDH2 | 3-hydroxybutyrate dehydrogenase type 2 | NM_020139 | 7.8227E-05 |
| 65472_at | C2orf68 | chromosome 2 open reading frame 68 | AI161338 | 8.0285E-05 |
| 221747_at | TNS1 | tensin 1 | AL046979 | 8.1012E-05 |
| 204944_at | PTPRG | protein tyrosine phosphatase receptor type G | NM_002841 | 8.5062E-05 |
| 205803_s_at | TRPC1 | transient receptor potential cation channel subfamily C member 1 | NM_003304 | 9.1121E-05 |
| 202664_at | WIPF1 | WAS/WASL interacting protein family member 1 | AW058622 | 9.5200E-05 |
| 212386_at | TCF4 | transcription factor 4 | BF592782 | 9.6608E-05 |
| 202598_at | S100A13 | S100 calcium binding protein A13 | NM_005979 | 9.9951E-05 |
| 209375_at | XPC | xeroderma pigmentosum complementation group C | D21089 | 1.0203E-04 |
| 221611_s_at | PHF7 | PHD finger protein 7 | AY014283 | 1.0523E-04 |
| 203638_s_at | FGFR2 | fibroblast growth factor receptor 2 | NM_022969 | 1.1006E-04 |
| 209990_s_at | GABBR2 | gamma-aminobutyric acid (GABA) B receptor 2 | AF056085 | 1.1153E-04 |
| 204446_s_at | ALOX5 | arachidonate 5-lipoxygenase | NM_000698 | 1.1577E-04 |
| 212530_at | NEK7 | NIMA (never in mitosis gene a)-related kinase 7 | AL080111 | 1.2283E-04 |
| 211675_s_at | MDFIC | MyoD family inhibitor domain containing | AF054589 | 1.3221E-04 |
| 222103_at | ATF1 | activating transcription factor 1 | AI434345 | 1.3421E-04 |
| 209763_at | CHRDL1 | chordin-like 1 | AL049176 | 1.3715E-04 |
| 216840_s_at | LAMA2 | laminin alpha 2 | AK026829 | 1.3816E-04 |
| 210664_s_at | TFPI | tissue factor pathway inhibitor (lipoprotein-associated coagulation inhibitor) | AF021834 | 1.3910E-04 |
| 222043_at | CLU | clusterin | AI982754 | 1.5732E-04 |

TABLE A-continued

| Probe Set ID | Gene Symbol | Gene Name | Representative Public ID | p value |
|---|---|---|---|---|
| 208747_s_at | C1S | complement component 1 s subcomponent | M18767 | 1.6336E-04 |
| 210129_s_at | TTLL3 | tubulin tyrosine ligase-like family member 3 | AF078842 | 1.6579E-04 |
| 204136_at | COL7A1 | collagen type VII alpha 1 | NM_000094 | 1.6678E-04 |
| 218168_s_at | CABC1 | chaperone ABC1 activity of bc1 complex homolog (*S. pombe*) | NM_020247 | 1.6820E-04 |
| 212690_at | DDHD2 | DDHD domain containing 2 | AB018268 | 1.6898E-04 |
| 203799_at | CD302 | CD302 molecule | NM_014880 | 1.7414E-04 |
| 209086_x_at | MCAM | melanoma cell adhesion molecule | BE964361 | 1.7613E-04 |
| 206227_at | CILP | cartilage intermediate layer protein nucleotide pyrophosphohydrolase | NM_003613 | 1.7709E-04 |
| 205498_at | GHR | growth hormone receptor | NM_000163 | 1.8023E-04 |
| 204939_s_at | PLN | phospholamban | NM_002667 | 1.8529E-04 |
| 209737_at | MAGI2 | membrane associated guanylate kinase WW and PDZ domain containing 2 | AB014605 | 1.9535E-04 |
| 207606_s_at | ARHGAP12 | Rho GTPase activating protein 12 | NM_018287 | 1.9567E-04 |
| 206502_s_at | INSM1 | insulinoma-associated 1 | NM_002196 | 2.0132E-04 |
| 201811_s_at | SH3BP5 | SH3-domain binding protein 5 (BTK-associated) | NM_004844 | 2.0465E-04 |
| 221530_s_at | BHLHE41 | basic helix-loop-helix family member e41 | BE857425 | 2.0872E-04 |
| 203177_x_at | TFAM | transcription factor A mitochondrial | NM_003201 | 2.1048E-04 |
| 202142_at | COPS8 | COP9 constitutive photomorphogenic homolog subunit 8 (*Arabidopsis*) | BC003090 | 2.1440E-04 |
| 221950_at | EMX2 | empty spiracles homeobox 2 | AI478455 | 2.1866E-04 |
| 205116_at | LAMA2 | laminin alpha 2 | NM_000426 | 2.2469E-04 |
| 218456_at | CAPRIN2 | caprin family member 2 | NM_023925 | 2.2868E-04 |
| 211340_s_at | MCAM | melanoma cell adhesion molecule | M28882 | 2.3165E-04 |
| 213247_at | SVEP1 | sushi von Willebrand factor type A EGF and pentraxin domain containing 1 | AA716107 | 2.3856E-04 |
| 209210_s_at | FERMT2 | fermitin family homolog 2 (*Drosophila*) | Z24725 | 2.4012E-04 |
| 201313_at | ENO2 | enolase 2 (gamma neuronal) | NM_001975 | 2.4732E-04 |
| 203884_s_at | RAB11FIP2 | RAB11 family interacting protein 2 (class I) | NM_014904 | 2.6635E-04 |
| 204853_at | ORC2L | origin recognition complex subunit 2-like (yeast) | NM_006190 | 2.6654E-04 |
| 221230_s_at | ARID4B | AT rich interactive domain 4B (RBP1-like) | NM_016374 | 2.6997E-04 |
| 212970_at | APBB2 | amyloid beta (A4) precursor protein-binding family B member 2 | AI694303 | 3.0394E-04 |
| 203446_at | OCRL | oculocerebrorenal syndrome of Lowe | NM_000276 | 3.0709E-04 |
| 203217_s_at | ST3GAL5 | ST3 beta-galactoside alpha-23-sialyltransferase 5 | NM_003896 | 3.1215E-04 |
| 221748_s_at | TNS1 | tensin 1 | AL046979 | 3.1441E-04 |
| 218087_s_at | SORBS1 | sorbin and SH3 domain containing 1 | NM_015385 | 3.1579E-04 |
| 203689_s_at | FMR1 | fragile X mental retardation 1 | AI743037 | 3.1785E-04 |
| 221218_s_at | TPK1 | thiamin pyrophosphokinase 1 | NM_022445 | 3.2805E-04 |
| 208669_s_at | EID1 | EP300 interacting inhibitor of differentiation 1 | AF109873 | 3.6197E-04 |
| 212736_at | C16orf45 | chromosome 16 open reading frame 45 | BE299456 | 3.6201E-04 |
| 218204_s_at | FYCO1 | FYVE and coiled-coil domain containing 1 | NM_024513 | 3.8403E-04 |
| 213373_s_at | CASP8 | caspase 8 apoptosis-related cysteine peptidase | BF439983 | 3.8971E-04 |
| 218625_at | NRN1 | neuritin 1 | NM_016588 | 4.0450E-04 |
| 210788_s_at | DHRS7 | dehydrogenase/reductase (SDR family) member 7 | AF126782 | 4.1440E-04 |
| 205612_at | MMRN1 | multimerin 1 | NM_007351 | 4.1487E-04 |
| 209335_at | DCN | decorin | AI281593 | 4.1933E-04 |
| 213519_s_at | LAMA2 | laminin alpha 2 | AI078169 | 4.2572E-04 |
| 217504_at | ABCA6 | ATP-binding cassette sub-family A (ABC1) member 6 | AA099357 | 4.3088E-04 |
| 203983_at | TSNAX | translin-associated factor X | NM_005999 | 4.3798E-04 |
| 202979_s_at | CREBZF | CREB/ATF bZIP transcription factor | NM_021212 | 4.3846E-04 |
| 207317_s_at | CASQ2 | calsequestrin 2 (cardiac muscle) | NM_001232 | 4.4266E-04 |
| 213480_at | VAMP4 | vesicle-associated membrane protein 4 | AF052100 | 4.4528E-04 |
| 203661_s_at | TMOD1 | tropomodulin 1 | BC002660 | 4.4930E-04 |
| 212764_at | ZEB1 | zinc finger E-box binding homeobox 1 | AI806174 | 4.5363E-04 |
| 209332_s_at | MAX | MYC associated factor X | BC003525 | 4.6003E-04 |
| 209732_at | CLEC2B | C-type lectin domain family 2 member B | BC005254 | 4.7151E-04 |
| 201648_at | JAK1 | Janus kinase 1 (a protein tyrosine kinase) | AL039831 | 4.7270E-04 |
| 214151_s_at | CCPG1 | cell cycle progression 1 | AU144243 | 4.8468E-04 |
| 221958_s_at | GPR177 | G protein-coupled receptor 177 | AA775681 | 4.9941E-04 |
| 212805_at | PRUNE2 | prune homolog 2 (*Drosophila*) | AB002365 | 5.0295E-04 |
| 213415_at | CLIC2 | chloride intracellular channel 2 | AI768628 | 5.1005E-04 |
| 213262_at | SACS | spastic ataxia of Charlevoix-Saguenay (sacsin) | AI932370 | 5.1009E-04 |
| 39582_at | CYLD | cylindromatosis (turban tumor syndrome) | AL050166 | 5.1801E-04 |
| 209265_s_at | METTL3 | methyltransferase like 3 | BC001650 | 5.2345E-04 |
| 201581_at | TMX4 | thioredoxin domain containing 13 | BF572868 | 5.3682E-04 |
| 213429_at | BICC1 | bicaudal C homolog 1 (*Drosophila*) | AW025579 | 5.4069E-04 |
| 203662_s_at | TMOD1 | tropomodulin 1 | NM_003275 | 5.4629E-04 |
| 206496_at | FMO3 | flavin containing monooxygenase 3 | NM_006894 | 5.4990E-04 |
| 40446_at | PHF1 | PHD finger protein 1 | AL021366 | 5.5428E-04 |
| 209467_s_at | MKNK1 | MAP kinase interacting serine/threonine kinase 1 | BC002755 | 5.5795E-04 |
| 219949_at | LRRC2 | leucine rich repeat containing 2 | NM_024512 | 5.6098E-04 |
| 218957_at | PAAF1 | proteasomal ATPase-associated factor 1 | NM_025155 | 5.6482E-04 |
| 201237_at | CAPZA2 | capping protein (actin filament) muscle Z-line alpha 2 | AV685920 | 5.9285E-04 |
| 209568_s_at | RGL1 | ral guanine nucleotide dissociation stimulator-like 1 | AF186779 | 5.9347E-04 |
| 212163_at | KIDINS220 | kinase D-interacting substrate 220kDa | AB033076 | 5.9605E-04 |
| 221757_at | PIK3IP1 | phosphoinositide-3-kinase interacting protein 1 | BE042976 | 6.0094E-04 |
| 204779_s_at | HOXB7 | homeobox B7 | NM_004502 | 6.0694E-04 |
| 221139_s_at | CSAD | cysteine sulfinic acid decarboxylase | NM_015989 | 6.1189E-04 |
| 218946_at | NFU1 | NFU1 iron-sulfur cluster scaffold homolog (*S. cerevisiae*) | NM_015700 | 6.2140E-04 |
| 201753_s_at | ADD3 | adducin 3 (gamma) | NM_019903 | 6.2561E-04 |

TABLE A-continued

| Probe Set ID | Gene Symbol | Gene Name | Representative Public ID | p value |
|---|---|---|---|---|
| 219895_at | FAM70A | family with sequence similarity 70 member A | NM_017938 | 6.2596E-04 |
| 202074_s_at | OPTN | optineurin | NM_021980 | 6.2626E-04 |
| 221556_at | CDC14B | CDC14 cell division cycle 14 homolog B (S. cerevisiae) | BF792631 | 6.3179E-04 |
| 213194_at | ROBO1 | roundabout axon guidance receptor homolog 1 (Drosophila) | BF059159 | 6.3295E-04 |
| 205986_at | AATK | apoptosis-associated tyrosine kinase | NM_004920 | 6.4921E-04 |
| 212558_at | SPRY1 | sprouty homolog 1 antagonist of FGF signaling (Drosophila) | BF508662 | 6.5829E-04 |
| 209787_s_at | HMGN4 | high mobility group nucleosomal binding domain 4 | BC001282 | 6.6274E-04 |
| 205083_at | AOX1 | aldehyde oxidase 1 | NM_001159 | 6.6633E-04 |
| 203427_at | ASF1A | ASF1 anti-silencing function 1 homolog A (S. cerevisiae) | NM_014034 | 6.6918E-04 |
| 209822_s_at | VLDLR | very low density lipoprotein receptor | L22431 | 6.7088E-04 |
| 217967_s_at | FAM129A | family with sequence similarity 129 member A | AF288391 | 6.7923E-04 |
| 203131_at | PDGFRA | platelet-derived growth factor receptor alpha polypeptide | NM_006206 | 6.9010E-04 |
| 210150_s_at | LAMA5 | laminin alpha 5 | BC003355 | 6.9685E-04 |
| 212675_s_at | CEP68 | centrosomal protein 68kDa | AB011154 | 6.9915E-04 |
| 219700_at | PLXDC1 | plexin domain containing 1 | NM_020405 | 7.0728E-04 |
| 47608_at | TJAP1 | tight junction associated protein 1 (peripheral) | AI697401 | 7.1269E-04 |
| 218288_s_at | CCDC90B | coiled-coil domain containing 90B | NM_021825 | 7.1308E-04 |
| 209285_s_at | C3orf63 | chromosome 3 open reading frame 63 | N38985 | 7.1497E-04 |
| 215245_x_at | FMR1 | fragile X mental retardation 1 | AA830884 | 7.1688E-04 |
| 212913_at | C6orf26 | chromosome 6 open reading frame 26 | BE674960 | 7.3457E-04 |
| 214086_s_at | PARP2 | poly (ADP-ribose) polymerase 2 | AK001980 | 7.4675E-04 |
| 218656_s_at | LHFP | lipoma HMGIC fusion partner | NM_005780 | 7.5779E-04 |
| 213800_at | CFH | complement factor H | X04697 | 7.6114E-04 |
| 212126_at | CBX5 | chromobox homolog 5 (HP1 alpha homolog Drosophila) | BG391282 | 7.6440E-04 |
| 206958_s_at | UPF3A | UPF3 regulator of nonsense transcripts homolog A (yeast) | AF318575 | 7.6790E-04 |
| 219848_s_at | ZNF432 | zinc finger protein 432 | NM_014650 | 7.6977E-04 |
| 212653_s_at | EHBP1 | EH domain binding protein 1 | AB020710 | 7.7156E-04 |
| 216044_x_at | FAM69A | family with sequence similarity 69 member A | AK027146 | 7.7784E-04 |
| 219161_s_at | CKLF | chemokine-like factor | NM_016951 | 7.8299E-04 |
| 210102_x_at | VWA5A | von Willebrand factor A domain containing 5A | BC001234 | 7.9257E-04 |
| 210155_at | MYOC | myocilin trabecular meshwork inducible glucocorticoid response | D88214 | 7.9752E-04 |
| 202409_at | IGF2 | insulin-like growth factor 2 (somatomedin A) | X07868 | 8.0081E-04 |
| 218501_at | ARHGEF3 | Rho guanine nucleotide exchange factor (GEF) 3 | NM_019555 | 8.2089E-04 |
| 212535_at | MEF2A | myocyte enhancer factor 2A | AA142929 | 8.2429E-04 |
| 214453_at | IFI44 | interferon-induced protein 44 | NM_006417 | 8.4432E-04 |
| 212368_at | ZNF292 | zinc finger protein 292 | AA972711 | 8.4711E-04 |
| 205011_at | VWA5A | von Willebrand factor A domain containing 5A | NM_014622 | 8.5033E-04 |
| 214684_at | MEF2A | myocyte enhancer factor 2A | X63381 | 8.5065E-04 |
| 208683_at | CAPN2 | calpain 2 (m/II) large subunit | M23254 | 8.5570E-04 |
| 205547_s_at | TAGLN | transgelin | NM_003186 | 8.6781E-04 |
| 218303_x_at | KRCC1 | lysine-rich coiled-coil 1 | NM_016618 | 8.7453E-04 |
| 201384_s_at | LOC100133166 | similar to neighbor of BRCA1 gene 1 | NM_005899 | 8.8284E-04 |
| 212589_at | RRAS2 | related RAS viral (r-ras) oncogene homolog 2 | AI753792 | 8.8349E-04 |
| 201034_at | ADD3 | adducin 3 (gamma) | BE545756 | 8.8904E-04 |
| 205158_at | RNASE4 | ribonuclease RNase A family 4 | NM_002937 | 8.9603E-04 |
| 204793_at | GPRASP1 | G protein-coupled receptor associated sorting protein 1 | NM_014710 | 8.9876E-04 |
| 202928_s_at | PHF1 | PHD finger protein 1 | NM_024165 | 8.9963E-04 |
| 203717_at | DPP4 | dipeptidyl-peptidase 4 | NM_001935 | 9.1050E-04 |
| 206157_at | PTX3 | pentraxin-related gene rapidly induced by IL-1 beta | NM_002852 | 9.2166E-04 |
| 219355_at | CXorf57 | chromosome X open reading frame 57 | NM_018015 | 9.2632E-04 |
| 204070_at | RARRES3 | retinoic acid receptor responder (tazarotene induced) 3 | NM_004585 | 9.2641E-04 |
| 204428_s_at | LCAT | lecithin-cholesterol acyltransferase | NM_000229 | 9.4980E-04 |
| 204897_at | PTGER4 | prostaglandin E receptor 4 (subtype EP4) | AA897516 | 9.5926E-04 |
| 209612_s_at | ADH1B | alcohol dehydrogenase 1B (class I) beta polypeptide | M24317 | 9.7983E-04 |
| 222001_x_at | LOC728855 | hypothetical LOC728855 | AI160126 | 9.8111E-04 |
| 218486_at | KLF11 | Kruppel-like factor 11 | AA149594 | 9.8974E-04 |
| 217816_s_at | PCNP | PEST proteolytic signal containing nuclear protein | NM_020357 | 9.9522E-04 |
| 209780_at | PHTF2 | putative homeodomain transcription factor 2 | AL136883 | 1.0108E-03 |
| 214683_s_at | CLK1 | CDC-like kinase 1 | AI251890 | 1.0113E-03 |
| 216620_at | ARHGEF10 | Rho guanine nucleotide exchange factor (GEF) 10 | AF009205 | 1.0159E-03 |
| 213158_at | | null | AA045174 | 1.0352E-03 |
| 210273_at | PCDH7 | protocadherin 7 | AB006757 | 1.0391E-03 |
| 212793_at | DAAM2 | dishevelled associated activator of morphogenesis 2 | BF513244 | 1.0515E-03 |
| 205545_x_at | DNAJC8 | DnaJ (Hsp40) homolog subfamily C member 8 | NM_014280 | 1.0523E-03 |
| 204310_s_at | NPR2 | natriuretic peptide receptor B/guanylate cyclase B (atrionatriuretic peptide receptor B) | NM_003995 | 1.0523E-03 |
| 216250_s_at | LPXN | leupaxin | X77598 | 1.0558E-03 |
| 202748_at | GBP2 | guanylate binding protein 2 interferon-inducible | NM_004120 | 1.0592E-03 |
| 208248_x_at | APLP2 | amyloid beta (A4) precursor-like protein 2 | NM_001642 | 1.0602E-03 |
| 216973_s_at | HOXB7 | homeobox B7 | S49765 | 1.0759E-03 |
| 221044_s_at | TRIM6 | tripartite motif-containing 34 | NM_021616 | 1.0950E-03 |
| 217853_at | TNS3 | tensin 3 | NM_022748 | 1.0951E-03 |
| 209009_at | ESD | esterase D/formylglutathione hydrolase | BC001169 | 1.0953E-03 |
| 220127_s_at | FBXL12 | F-box and leucine-rich repeat protein 12 | NM_017703 | 1.0997E-03 |
| 218196_at | OSTM1 | osteopetrosis associated transmembrane protein 1 | NM_014028 | 1.1047E-03 |
| 200986_at | SERPING1 | serpin peptidase inhibitor clade G (C1 inhibitor) member 1 | NM_000062 | 1.1056E-03 |
| 214044_at | RYR2 | ryanodine receptor 2 (cardiac) | BE968750 | 1.1145E-03 |

TABLE A-continued

| Probe Set ID | Gene Symbol | Gene Name | Representative Public ID | p value |
|---|---|---|---|---|
| 205549_at | PCP4 | Purkinje cell protein 4 | NM_006198 | 1.1168E-03 |
| 212761_at | TCF7L2 | transcription factor 7-like 2 (T-cell specific HMG-box) | AI949687 | 1.1230E-03 |
| 204994_at | MX2 | myxovirus (influenza virus) resistance 2 (mouse) | NM_002463 | 1.1250E-03 |
| 218919_at | ZFAND1 | zinc finger AN1-type domain 1 | NM_024699 | 1.1391E-03 |
| 204438_at | MRC1L1 | mannose receptor C type 1 | NM_002438 | 1.1392E-03 |
| 218146_at | GLT8D1 | glycosyltransferase 8 domain containing 1 | NM_018446 | 1.1414E-03 |
| 222229_x_at | RPL26P37 | 60S ribosomal protein L26 pseudogene | AL121871 | 1.1749E-03 |
| 212509_s_at | MXRA7 | matrix-remodelling associated 7 | BF968134 | 1.1781E-03 |
| 204938_s_at | PLN | phospholamban | M60411 | 1.1841E-03 |
| 216241_s_at | TCEA1 | transcription elongation factor A (SII) 1 | X57198 | 1.1997E-03 |
| 214703_s_at | MAN2B2 | mannosidase alpha class 2B member 2 | AW954107 | 1.2028E-03 |
| 203336_s_at | ITGB1BP1 | integrin beta 1 binding protein 1 | AL548363 | 1.2099E-03 |
| 65718_at | GPR124 | G protein-coupled receptor 124 | AI655903 | 1.2271E-03 |
| 211679_x_at | GABBR2 | gamma-aminobutyric acid (GABA) B receptor 2 | AF095784 | 1.2692E-03 |
| 202552_s_at | CRIM1 | cysteine rich transmembrane BMP regulator 1 (chordin-like) | NM_016441 | 1.2732E-03 |
| 202853_s_at | RYK | RYK receptor-like tyrosine kinase | NM_002958 | 1.3008E-03 |
| 213703_at | LOC150759 | hypothetical protein LOC150759 | W95043 | 1.3148E-03 |
| 206167_s_at | ARHGAP6 | Rho GTPase activating protein 6 | NM_001174 | 1.3166E-03 |
| 213294_at | EIF2AK2 | eukaryotic translation initiation factor 2-alpha kinase 2 | AV755522 | 1.3257E-03 |
| 212343_at | YIPF6 | Yip1 domain family member 6 | AL117461 | 1.3337E-03 |
| 212586_at | CAST | calpastatin | AA195244 | 1.3533E-03 |
| 212077_at | CALD1 | caldesmon 1 | AL583520 | 1.3697E-03 |
| 213309_at | PLCL2 | phospholipase C-like 2 | AL117515 | 1.3761E-03 |
| 203774_at | MTR | 5-methyltetrahydrofolate-homocysteine methyltransferase | NM_000254 | 1.4049E-03 |
| 209621_s_at | PDLIM3 | PDZ and LIM domain 3 | AF002280 | 1.4120E-03 |
| 203249_at | EZH1 | enhancer of zeste homolog 1 (Drosophila) | AB002386 | 1.4127E-03 |
| 201784_s_at | C11orf58 | chromosome 11 open reading frame 58 | NM_014267 | 1.4222E-03 |
| 203156_at | AKAP11 | A kinase (PRKA) anchor protein 11 | NM_016248 | 1.4238E-03 |
| 213165_at | CEP350 | centrosomal protein 350kDa | AI041204 | 1.4348E-03 |
| 212984_at | ATF2 | activating transcription factor 2 | BE786164 | 1.4415E-03 |
| 202907_s_at | NBN | nibrin | NM_002485 | 1.4488E-03 |
| 205260_s_at | ACYP1 | acylphosphatase 1 erythrocyte (common) type | NM_001107 | 1.4518E-03 |
| 206332_s_at | IFI16 | interferon gamma-inducible protein 16 | NM_005531 | 1.4578E-03 |
| 212390_at | LOC727893 | similar to phosphodiesterase 4D interacting protein (myomegalin) | AB007923 | 1.4580E-03 |
| 212455_at | YTHDC1 | YTH domain containing 1 | N36997 | 1.4597E-03 |
| 209337_at | PSIP1 | PC4 and SFRS1 interacting protein 1 | AF063020 | 1.4630E-03 |
| 213375_s_at | N4BP2L1 | NEDD4 binding protein 2-like 1 | N80918 | 1.4697E-03 |
| 34031_i_at | KRIT1 | KRIT1 ankyrin repeat containing | U90269 | 1.4716E-03 |
| 210538_s_at | BIRC3 | baculoviral IAP repeat-containing 3 | U37546 | 1.4849E-03 |
| 216949_s_at | PKD1 | polycystic kidney disease 1 (autosomal dominant) | L39891 | 1.4913E-03 |
| 219778_at | ZFPM2 | zinc finger protein multitype 2 | NM_012082 | 1.4980E-03 |
| 203505_at | ABCA1 | ATP-binding cassette sub-family A (ABC1) member 1 | AF285167 | 1.4984E-03 |
| 202328_s_at | PKD1 | polycystic kidney disease 1 (autosomal dominant) | NM_000296 | 1.5072E-03 |
| 219820_at | SLC6A16 | solute carrier family 6 member 16 | NM_014037 | 1.5190E-03 |
| 207558_s_at | PITX2 | paired-like homeodomain 2 | NM_000325 | 1.5248E-03 |
| 209236_at | SLC23A2 | solute carrier family 23 (nucleobase transporters) member 2 | AL389886 | 1.5384E-03 |
| 201038_s_at | ANP32A | Cerebellar leucine rich acidic nuclear protein (LANP) | T67821 | 1.5626E-03 |
| 205407_at | RECK | reversion-inducing-cysteine-rich protein with kazal motifs | NM_021111 | 1.5697E-03 |
| 203281_s_at | UBA7 | ubiquitin-like modifier activating enzyme 7 | NM_003335 | 1.5792E-03 |
| 206201_s_at | MEOX2 | mesenchyme homeobox 2 | NM_005924 | 1.5832E-03 |
| 209815_s_at | PTCH1 | patched homolog 1 (Drosophila) | BG054916 | 1.5922E-03 |
| 213295_at | CYLD | cylindromatosis (turban tumor syndrome) | AA555096 | 1.6088E-03 |
| 211742_s_at | EVI2B | ecotropic viral integration site 2B | BC005926 | 1.6282E-03 |
| 203035_s_at | PIAS3 | protein inhibitor of activated STAT 3 | NM_006099 | 1.6319E-03 |
| 212233_at | MAP1B | microtubule-associated protein 1B | AL523076 | 1.6369E-03 |
| 211743_s_at | PRG2 | proteoglycan 2 bone marrow (natural killer cell activator eosinophil granule major basic protein) | BC005929 | 1.6770E-03 |
| 213388_at | PDE4DIP | phosphodiesterase 4D interacting protein | H15535 | 1.6837E-03 |
| 206159_at | GDF10 | growth differentiation factor 10 | NM_004962 | 1.6866E-03 |
| 219654_at | PTPLA | protein tyrosine phosphatase-like (proline instead of catalytic arginine) member A | NM_014241 | 1.6959E-03 |
| 210312_s_at | IFT20 | intraflagellar transport 20 homolog (Chlamydomonas) | BC002640 | 1.7097E-03 |
| 210794_s_at | MEG3 | maternally expressed 3 (non-protein coding) | AF119863 | 1.7106E-03 |
| 202136_at | ZMYND11 | zinc finger MYND domain containing 11 | BE250417 | 1.7169E-03 |
| 201395_at | RBM5 | RNA binding motif protein 5 | NM_005778 | 1.7384E-03 |
| 203881_at | DMD | dystrophin | NM_004010 | 1.7474E-03 |
| 208861_s_at | ATRX | alpha thalassemia/mental retardation syndrome X-linked (RAD54 homolog S. cerevisiae) | U72937 | 1.7816E-03 |
| 202104_s_at | SPG7 | spastic paraplegia 7 (pure and complicated autosomal recessive) | NM_003119 | 1.7951E-03 |
| 209656_s_at | TMEM47 | transmembrane protein 47 | AL136550 | 1.7975E-03 |
| 210644_s_at | LAIR1 | leukocyte-associated immunoglobulin-like receptor 1 | AF109683 | 1.8453E-03 |
| 213849_s_at | PPP2R2B | protein phosphatase 2 (formerly 2A) regulatory subunit B beta isoform | AA974416 | 1.8555E-03 |
| 212547_at | BRD3 | bromodomain containing 3 | N34842 | 1.8672E-03 |
| 213880_at | LGR5 | leucine-rich repeat-containing G protein-coupled receptor 5 | AL524520 | 1.8699E-03 |
| 212698_s_at | SEPT10 | septin 10 | BF966021 | 1.8766E-03 |
| 204215_at | C7orf23 | chromosome 7 open reading frame 23 | NM_024315 | 1.8796E-03 |
| 204277_s_at | TK2 | thymidine kinase 2 mitochondrial | BE895437 | 1.8964E-03 |

TABLE A-continued

| Probe Set ID | Gene Symbol | Gene Name | Representative Public ID | p value |
|---|---|---|---|---|
| 217954_s_at | PHF3 | PHD finger protein 3 | NM_015153 | 1.9020E-03 |
| 207845_s_at | ANAPC10 | anaphase promoting complex subunit 10 | NM_014885 | 1.9148E-03 |
| 213071_at | DPT | dermatopontin | AL049798 | 1.9353E-03 |
| 210829_s_at | SSBP2 | single-stranded DNA binding protein 2 | AF077048 | 1.9382E-03 |
| 217989_at | HSD17B11 | hydroxysteroid (17-beta) dehydrogenase 11 | NM_016245 | 1.9516E-03 |
| 219862_s_at | NARF | nuclear prelamin A recognition factor | NM_012336 | 1.9592E-03 |
| 212726_at | PHF2 | PHD finger protein 2 | AB014562 | 1.9691E-03 |
| 205933_at | SETBP1 | SET binding protein 1 | NM_015559 | 1.9781E-03 |
| 204894_s_at | AOC3 | amine oxidase copper containing 3 (vascular adhesion protein 1) | NM_003734 | 1.9794E-03 |
| 209894_at | LEPR | leptin receptor | U50748 | 1.9798E-03 |
| 202363_at | SPOCK1 | sparc/osteonectin cwcv and kazal-like domains proteoglycan (testican) 1 | AF231124 | 1.9920E-03 |
| 202265_at | BMI1 | BMI1 polycomb ring finger oncogene | NM_005180 | 1.9971E-03 |
| 214494_s_at | SPG7 | spastic paraplegia 7 (pure and complicated autosomal recessive) | NM_005200 | 2.0054E-03 |
| 218518_at | FAM13B | family with sequence similarity 13 member B1 | NM_016603 | 2.0060E-03 |
| 210105_s_at | FYN | FYN oncogene related to SRC FGR YES | M14333 | 2.0099E-03 |

TABLE B

| Probe Set ID | Gene Symbol | Gene Name | Representative Public ID | p value |
|---|---|---|---|---|
| 213330_s_at | STIP1 | stress-induced-phosphoprotein 1 | BE886580 | 1.9219E-07 |
| 213887_s_at | POLR2E | polymerase (RNA) II (DNA directed) polypeptide E 25kDa | AI554759 | 5.9774E-07 |
| 201631_s_at | IER3 | immediate early response 3 | NM_003897 | 8.6381E-07 |
| 221610_s_at | STAP2 | signal transducing adaptor family member 2 | BC000795 | 3.7342E-06 |
| 205847_at | PRSS22 | protease serine 22 | NM_022119 | 4.7883E-06 |
| 208928_at | POR | P450 (cytochrome) oxidoreductase | AF258341 | 5.1845E-06 |
| 201530_x_at | EIF4A1 | eukaryotic translation initiation factor 4A isoform 1 | NM_001416 | 1.0859E-05 |
| 217835_x_at | C20orf24 | chromosome 20 open reading frame 24 | NM_018840 | 1.0871E-05 |
| 222231_s_at | LRRC59 | leucine rich repeat containing 59 | AK025328 | 1.1501E-05 |
| 201118_at | PGD | phosphogluconate dehydrogenase | NM_002631 | 1.1705E-05 |
| 206426_at | MLANA | melan-A | NM_005511 | 1.4820E-05 |
| 210719_s_at | HMG20B | high-mobility group 20B | BC002552 | 1.5452E-05 |
| 208909_at | UQCRFS1 | ubiquinol-cytochrome c reductase Rieske iron-sulfur polypeptide 1 | BC000649 | 1.8592E-05 |
| 208336_s_at | GPSN2 | glycoprotein synaptic 2 | NM_004868 | 2.3068E-05 |
| 201195_s_at | SLC7A5 | solute carrier family 7 (cationic amino acid transporter y+ system) member 5 | AB018009 | 2.3348E-05 |
| 211787_s_at | EIF4A1 | eukaryotic translation initiation factor 4A isoform 1 | BC006210 | 2.8418E-05 |
| 202435_s_at | CYP1B1 | cytochrome P450 family 1 subfamily B polypeptide 1 | AU154504 | 2.9878E-05 |
| 204039_at | CEBPA | CCAAT/enhancer binding protein (C/EBP) alpha | NM_004364 | 3.0309E-05 |
| 212070_at | GPR56 | G protein-coupled receptor 56 | AL554008 | 3.6504E-05 |
| 209126_x_at | KRT6B | keratin 6B | L42612 | 3.7302E-05 |
| 220174_at | LRRC8E | leucine rich repeat containing 8 family member E | NM_025061 | 4.2418E-05 |
| 219402_s_at | DERL1 | Der1-like domain family member 1 | NM_024295 | 5.1192E-05 |
| 212858_at | PAQR4 | progestin and adipoQ receptor family member IV | AL520675 | 5.2306E-05 |
| 203702_s_at | TTLL4 | tubulin tyrosine ligase-like family member 4 | AL043927 | 5.8383E-05 |
| 217854_s_at | POLR2E | polymerase (RNA) II (DNA directed) polypeptide E 25kDa | NM_002695 | 5.8400E-05 |
| 201287_s_at | SDC1 | syndecan 1 | NM_002997 | 5.8419E-05 |
| 212041_at | ATP6V0D1 | ATPase H+ transporting lysosomal 38kDa V0 subunit d1 | AL566172 | 6.4338E-05 |
| 212531_at | LCN2 | lipocalin 2 | NM_005564 | 6.5499E-05 |
| 220013_at | ABHD9 | abhydrolase domain containing 9 | NM_024794 | 6.8876E-05 |
| 209792_s_at | KLK10 | kallikrein-related peptidase 10 | BC002710 | 6.9165E-05 |
| 212085_at | SLC25A6 | solute carrier family 25 (mitochondrial carrier; adenine nucleotide translocator) member 6 | AA916851 | 7.4951E-05 |
| 213680_at | KRT6B | keratin 6B | AI831452 | 7.5036E-05 |
| 210020_x_at | CALML3 | calmodulin-like 3 | M58026 | 7.9243E-05 |
| 208002_s_at | ACOT7 | acyl-CoA thioesterase 7 | NM_007274 | 8.1836E-05 |
| 216607_at | CYP51A1 | cytochrome P450 family 51 subfamily A polypeptide 1 | U40053 | 8.3548E-05 |
| 202005_at | ST14 | suppression of tumorigenicity 14 (colon carcinoma) | NM_021978 | 8.4956E-05 |
| 216512_s_at | DCT | dopachrome tautomerase (dopachrome delta-isomerase tyrosine-related protein 2) | AL139318 | 9.5957E-05 |
| 204331_s_at | MRPS12 | mitochondrial ribosomal protein S12 | NM_021107 | 1.0048E-04 |
| 213571_s_at | EIF4E2 | eukaryotic translation initiation factor 4E family member 2 | BF516289 | 1.0230E-04 |
| 212075_s_at | CSNK2A1 | casein kinase 2 alpha 1 polypeptide | AI161318 | 1.1634E-04 |
| 212501_at | CEBPB | CCAAT/enhancer binding protein (C/EBP) beta | AL564683 | 1.1968E-04 |
| 203663_s_at | COX5A | cytochrome c oxidase subunit Va | NM_004255 | 1.2510E-04 |
| 36994_at | ATP6V0C | ATPase H+ transporting lysosomal 16kDa V0 subunit c | M62762 | 1.2780E-04 |
| 201976_s_at | MYO10 | myosin X | NM_012334 | 1.3176E-04 |
| 209502_s_at | BAIAP2 | BAI1-associated protein 2 | BC002495 | 1.4026E-04 |
| 200658_s_at | PHB | prohibitin | AL560017 | 1.4366E-04 |
| 206630_at | TYR | tyrosinase (oculocutaneous albinism IA) | NM_000372 | 1.4525E-04 |
| 200895_s_at | FKBP4 | FK506 binding protein 4 59kDa | NM_002014 | 1.4549E-04 |
| 204532_x_at | UGT1A10 | UDP glucuronosyltransferase 1 family polypeptide A1 | NM_021027 | 1.5004E-04 |
| 221676_s_at | CORO1C | coronin actin binding protein 1C | BC002342 | 1.5064E-04 |
| 204132_s_at | FOXO3 | forkhead box O3 | NM_001455 | 1.5795E-04 |

TABLE B-continued

| Probe Set ID | Gene Symbol | Gene Name | Representative Public ID | p value |
|---|---|---|---|---|
| 217999_s_at | PHLDA1 | pleckstrin homology-like domain family A member 1 | NM_007350 | 1.6252E-04 |
| 206498_at | OCA2 | oculocutaneous albinism II | NM_000275 | 1.6286E-04 |
| 201310_s_at | C5orf13 | chromosome 5 open reading frame 13 | NM_004772 | 1.6328E-04 |
| 209125_at | KRT6A | keratin 6A | J00269 | 1.6608E-04 |
| 209149_s_at | TM9SF1 | transmembrane 9 superfamily member 1 | BE899402 | 1.6635E-04 |
| 206427_at | MLANA | melan-A | U06654 | 1.6829E-04 |
| 219752_at | RASAL1 | RAS protein activator like 1 (GAP1 like) | NM_004658 | 1.7105E-04 |
| 201322_at | ATP5B | ATP synthase H+ transporting mitochondrial F1 complex beta polypeptide | NM_001686 | 1.7170E-04 |
| 208918_s_at | NADK | NAD kinase | AI334128 | 1.7531E-04 |
| 218548_x_at | TEX264 | testis expressed 264 | NM_015926 | 1.7787E-04 |
| 206595_at | CST6 | cystatin E/M | NM_001323 | 1.8189E-04 |
| 217947_at | CMTM6 | CKLF-like MARVEL transmembrane domain containing 6 | NM_017801 | 1.9994E-04 |
| 218028_at | ELOVL1 | elongation of very long chain fatty acids (FEN1/Elo2 SUR4/Elo3 yeast)-like 1 | NM_016031 | 2.0196E-04 |
| 202068_s_at | LDLR | low density lipoprotein receptor | NM_000527 | 2.1143E-04 |
| 221295_at | CIDEA | cell death-inducing DFFA-like effector a | NM_001279 | 2.1176E-04 |
| 209482_at | POP7 | processing of precursor 7 ribonuclease P/MRP subunit (S. cerevisiae) | BC001430 | 2.1329E-04 |
| 214580_x_at | KRT6C | keratin 6A | AL569511 | 2.1776E-04 |
| 201131_s_at | CDH1 | cadherin 1 type 1 E-cadherin (epithelial) | NM_004360 | 2.2275E-04 |
| 206094_x_at | UGT1A10 | UDP glucuronosyltransferase 1 family polypeptide A1 | NM_001072 | 2.2335E-04 |
| 208906_at | BSCL2 | Bernardinelli-Seip congenital lipodystrophy 2 (seipin) | BC004911 | 2.2965E-04 |
| 207986_x_at | CYB561 | cytochrome b-561 | NM_001915 | 2.3248E-04 |
| 222138_at | WDR13 | WD repeat domain 13 | AF158978 | 2.5149E-04 |
| 201577_at | NME1 | non-metastatic cells 1 protein (NM23A) expressed in | NM_000269 | 2.5496E-04 |
| 210613_s_at | SYNGR1 | synaptogyrin 1 | BC000731 | 2.5878E-04 |
| 206445_s_at | PRMT1 | protein arginine methyltransferase 1 | NM_001536 | 2.6001E-04 |
| 57163_at | ELOVL1 | elongation of very long chain fatty acids (FEN1/Elo2 SUR4/Elo3 yeast)-like 1 | H93026 | 2.6427E-04 |
| 218368_x_at | TNFRSF12A | tumor necrosis factor receptor superfamily member 12A | NM_016639 | 2.7727E-04 |
| 218897_at | TMEM177 | transmembrane protein 177 | NM_030577 | 2.7927E-04 |
| 205749_at | CYP1A1 | cytochrome P450 family 1 subfamily A polypeptide 1 | NM_000499 | 2.8164E-04 |
| 203287_at | LAD1 | ladinin 1 | NM_005558 | 2.9269E-04 |
| 218189_s_at | NANS | N-acetylneuraminic acid synthase | NM_018946 | 2.9981E-04 |
| 201489_at | PPIF | peptidylprolyl isomerase F | BC005020 | 3.0445E-04 |
| 202799_at | CLPP | ClpP caseinolytic peptidase ATP-dependent proteolytic subunit homolog (E. coli) | NM_006012 | 3.1644E-04 |
| 215206_at | | null | AK025143 | 3.1867E-04 |
| 208700_s_at | TKT | transketolase | L12711 | 3.2294E-04 |
| 207126_x_at | UGT1A10 | UDP glucuronosyltransferase 1 family polypeptide A1 | NM_000463 | 3.2300E-04 |
| 204941_s_at | ALDH3B2 | aldehyde dehydrogenase 3 family member B2 | AA071510 | 3.2381E-04 |
| 212826_s_at | SLC25A6 | solute carrier family 25 (mitochondrial carrier; adenine nucleotide translocator) member 6 | AI961224 | 3.2556E-04 |
| 218739_at | ABHD5 | abhydrolase domain containing 5 | NM_016006 | 3.2819E-04 |
| 209208_at | MPDU1 | mannose-P-dolichol utilization defect 1 | AF059752 | 3.3424E-04 |
| 200846_at | PPP1CA | protein phosphatase 1 catalytic subunit alpha isoform | NM_002708 | 3.5337E-04 |
| 200750_s_at | RAN | RAN member RAS oncogene family | AF054183 | 3.5383E-04 |
| 201739_at | SGK1 | serum/glucocorticoid regulated kinase 1 | NM_005627 | 3.5459E-04 |
| 212165_at | TMEM183B | transmembrane protein 183A | AF070537 | 3.5638E-04 |
| 218756_s_at | DHRS11 | dehydrogenase/reductase (SDR family) member 11 | NM_024308 | 3.6110E-04 |
| 204733_at | KLK6 | kallikrein-related peptidase 6 | NM_002774 | 3.8374E-04 |
| 213726_x_at | TUBB2C | tubulin beta 2C | AA515698 | 3.9114E-04 |
| 214549_x_at | SPRR1A | small proline-rich protein 1A | NM_005987 | 3.9410E-04 |
| 211800_s_at | USP4 | ubiquitin specific peptidase 4 (proto-oncogene) | AF017306 | 4.0198E-04 |
| 202712_s_at | LOC100133623 | creatine kinase mitochondrial 1A | NM_020990 | 4.0457E-04 |
| 213796_at | SPRR1A | small proline-rich protein 1A | AI923984 | 4.1153E-04 |
| 209036_s_at | MDH2 | malate dehydrogenase 2 NAD (mitochondrial) | BC001917 | 4.1608E-04 |
| 31846_at | RHOD | ras homolog gene family member D | AW003733 | 4.1843E-04 |
| 217140_s_at | LOC100133724 | similar to Voltage-dependent anion-selective channel protein 1 (VDAC-1) (hVDAC1) (Outer mitochondrial membrane protein porin 1) (Plasmalemmal porin) ( Porin 31HL) (Porin 31HM) | AJ002428 | 4.1935E-04 |
| 207367_at | ATP12A | ATPase H+/K+ transporting nongastric alpha polypeptide | NM_001676 | 4.1960E-04 |
| 203109_at | UBE2M | ubiquitin-conjugating enzyme E2M (UBC12 homolog yeast) | NM_003969 | 4.2473E-04 |
| 202421_at | IGSF3 | immunoglobulin superfamily member 3 | AB007935 | 4.2745E-04 |
| 208977_x_at | TUBB2C | tubulin beta 2C | BC004188 | 4.2872E-04 |
| 201231_s_at | ENO1 | enolase 1 (alpha) | NM_001428 | 4.3258E-04 |
| 207507_s_at | ATP5G3 | ATP synthase H+ transporting mitochondrial F0 complex subunit C3 (subunit 9) | NM_001689 | 4.3401E-04 |
| 217973_at | DCXR | dicarbonyl/L-xylulose reductase | NM_016286 | 4.3576E-04 |
| 213132_s_at | MCAT | malonyl CoA:ACP acyltransferase (mitochondrial) | AL022237 | 4.3749E-04 |
| 212236_x_at | KRT17 | keratin 17 | Z19574 | 4.3848E-04 |
| 207192_at | DNASE1L2 | deoxyribonuclease I-like 2 | NM_001374 | 4.4267E-04 |
| 202376_at | SERPINA3 | serpin peptidase inhibitor clade A (alpha-1 antiproteinase antitrypsin) member 3 | NM_001085 | 4.4762E-04 |
| 208813_at | GOT1 | glutamic-oxaloacetic transaminase 1 soluble (aspartate aminotransferase 1) | BC000498 | 4.5160E-04 |
| 205157_s_at | KRT17 | keratin 17 | NM_000422 | 4.5700E-04 |
| 200862_at | DHCR24 | 24-dehydrocholesterol reductase | NM_014762 | 4.6729E-04 |
| 205293_x_at | BAIAP2 | BAI1-associated protein 2 | AB017120 | 4.6882E-04 |
| 202436_s_at | CYP1B1 | cytochrome P450 family 1 subfamily B polypeptide 1 | AU144855 | 4.7083E-04 |
| 220994_s_at | STXBP6 | syntaxin binding protein 6 (amisyn) | NM_014178 | 4.7382E-04 |
| 216475_at | | null | AL133269 | 4.8343E-04 |
| 204341_at | TRIM16 | tripartite motif-containing 16 | NM_006470 | 4.8792E-04 |

TABLE B-continued

| Probe Set ID | Gene Symbol | Gene Name | Representative Public ID | p value |
|---|---|---|---|---|
| 201175_at | TMX2 | thioredoxin domain containing 14 | NM_015959 | 5.0497E-04 |
| 203462_x_at | EIF3B | eukaryotic translation initiation factor 3 subunit B | NM_003751 | 5.1683E-04 |
| 205064_at | SPRR1B | small proline-rich protein 1B (cornifin) | NM_003125 | 5.3559E-04 |
| 210959_s_at | SRD5A1 | steroid-5-alpha-reductase alpha polypeptide 1 (3-oxo-5 alpha-steroid 4-deltadehydrogenase alpha 1) | AF113128 | 5.3596E-04 |
| 220976_s_at | LOC728946 | keratin associated protein 1-1 | NM_030967 | 5.3814E-04 |
| 215626_at | | null | AU144887 | 5.4582E-04 |
| 209800_at | KRT16 | keratin 16 | AF061812 | 5.4918E-04 |
| 206714_at | ALOX15B | arachidonate 15-lipoxygenase type B | NM_001141 | 5.5543E-04 |
| 206302_s_at | NUDT4 | nudix (nucleoside diphosphate linked moiety X)-type motif 4 | NM_019094 | 5.6492E-04 |
| 212861_at | MFSD5 | major facilitator superfamily domain containing 5 | BF690150 | 5.7171E-04 |
| 208756_at | EIF3I | eukaryotic translation initiation factor 3 subunit I | U36764 | 5.8834E-04 |
| 205338_s_at | DCT | dopachrome tautomerase (dopachrome delta-isomerase tyrosine-related protein 2) | NM_001922 | 5.9284E-04 |
| 205436_s_at | H2AFX | H2A histone family member X | NM_002105 | 5.9320E-04 |
| 215952_s_at | OAZ1 | ornithine decarboxylase antizyme 1 | AF090094 | 5.9942E-04 |
| 210130_s_at | TM7SF2 | transmembrane 7 superfamily member 2 | AF096304 | 6.0308E-04 |
| 215100_at | C6orf105 | chromosome 6 open reading frame 105 | AL022724 | 6.1457E-04 |
| 205417_s_at | DAG1 | dystroglycan 1 (dystrophin-associated glycoprotein 1) | NM_004393 | 6.2276E-04 |
| 216237_s_at | MCM5 | minichromosome maintenance complex component 5 | AA807529 | 6.2290E-04 |
| 201113_at | TUFM | Tu translation elongation factor mitochondrial | NM_003321 | 6.2822E-04 |
| 205694_at | TYRP1 | tyrosinase-related protein 1 | NM_000550 | 6.3022E-04 |
| 202315_s_at | BCR | breakpoint cluster region | NM_004327 | 6.3140E-04 |
| 203391_at | FKBP2 | FK506 binding protein 2 13kDa | NM_004470 | 6.3385E-04 |
| 218880_at | FOSL2 | FOS-like antigen 2 | N36408 | 6.3536E-04 |
| 220978_at | LOC728951 | keratin associated protein 1-3 | NM_030966 | 6.3713E-04 |
| 207670_at | KRT85 | keratin 85 | NM_002283 | 6.4259E-04 |
| 201463_s_at | LOC100133665 | similar to transaldolase | NM_006755 | 6.4937E-04 |
| 210589_s_at | GBA | glucosidase beta; acid (includes glucosylceramidase) | D13287 | 6.6217E-04 |
| 219395_at | ESRP2 | RNA binding motif protein 35B | NM_024939 | 6.6704E-04 |
| 204675_at | SRD5A1 | steroid-5-alpha-reductase alpha polypeptide 1 (3-oxo-5 alpha-steroid delta 4-dehydrogenase alpha 1) | NM_001047 | 6.6827E-04 |
| 215808_at | KLK10 | kallikrein-related peptidase 10 | AK026045 | 6.7220E-04 |
| 33646_g_at | GM2A | GM2 ganglioside activator | X61094 | 6.8424E-04 |
| 207508_at | ATP5G3 | ATP synthase H+ transporting mitochondrial F0 complex subunit C3 (subunit 9) | NM_001689 | 6.8567E-04 |
| 214370_at | S100A8 | Calcium-binding protein in macrophages (MRP-8) macrophage migration inhibitory factor (MIF)-related protein | AW238654 | 6.8779E-04 |
| 200803_s_at | TMBIM6 | transmembrane BAX inhibitor motif containing 6 | AF033095 | 6.8912E-04 |
| 221872_at | RARRES1 | retinoic acid receptor responder (tazarotene induced) 1 | AI669229 | 6.9158E-04 |
| 207088_s_at | SLC25A11 | solute carrier family 25 (mitochondrial carrier; oxoglutarate carrier) member 11 | NM_003562 | 6.9700E-04 |
| 219412_at | RAB38 | RAB38 member RAS oncogene family | NM_022337 | 7.0409E-04 |
| 218893_at | ISOC2 | isochorismatase domain containing 2 | NM_024710 | 7.1390E-04 |
| 202917_s_at | S100A8 | S100 calcium binding protein A8 | NM_002964 | 7.1637E-04 |
| 220970_s_at | LOC644350 | keratin associated protein 2.1B | NM_030977 | 7.2209E-04 |
| 219911_s_at | LOC100134295 | similar to Solute carrier organic anion transporter family member 4A1 | NM_016354 | 7.2592E-04 |
| 200894_s_at | FKBP4 | FK506 binding protein 4 59kDa | AA894574 | 7.3446E-04 |
| 206709_x_at | GPT | glutamic-pyruvate transaminase (alanine aminotransferase) | NM_005309 | 7.3607E-04 |
| 219723_x_at | AGPAT3 | 1-acylglycerol-3-phosphate O-acyltransferase 3 | NM_020132 | 7.4330E-04 |
| 209372_x_at | TUBB2B | tubulin beta 2A | BF971587 | 7.4649E-04 |
| 203535_at | S100A9 | S100 calcium binding protein A9 | NM_002965 | 7.6032E-04 |
| 218214_at | C12orf44 | chromosome 12 open reading frame 44 | NM_021934 | 7.6225E-04 |
| 206391_at | RARRES1 | retinoic acid receptor responder (tazarotene induced) 1 | NM_002888 | 7.6289E-04 |
| 206605_at | P11 | 26 serine protease | NM_006025 | 7.7125E-04 |
| 201490_s_at | PPIF | peptidylprolyl isomerase F | NM_005729 | 7.7571E-04 |
| 219850_s_at | EHF | ets homologous factor | NM_012153 | 7.7583E-04 |
| 221256_s_at | HDHD3 | haloacid dehalogenase-like hydrolase domain containing 3 | NM_031219 | 7.7612E-04 |
| 218105_s_at | MRPL4 | mitochondrial ribosomal protein L4 | NM_015956 | 7.8720E-04 |
| 216810_at | KRTAP4-7 | keratin associated protein 4-7 | AJ406939 | 7.9938E-04 |
| 218556_at | ORMDL2 | ORM1-like 2 (*S. cerevisiae*) | NM_014182 | 8.2452E-04 |
| 201286_at | SDC1 | syndecan 1 | Z48199 | 8.2815E-04 |
| 211715_s_at | BDH1 | 3-hydroxybutyrate dehydrogenase type 1 | BC005844 | 8.2925E-04 |
| 220189_s_at | MGAT4B | mannosyl (alpha-13-)-glycoprotein beta-14-N-acetylglucosaminyltransferase isozyme B | NM_014275 | 8.3956E-04 |
| 217208_s_at | DLG1 | discs large homolog 1 (*Drosophila*) | AL121981 | 8.4322E-04 |
| 208653_s_at | CD164 | CD164 molecule sialomucin | AF263279 | 8.4956E-04 |
| 207065_at | KRT75 | keratin 75 | NM_004693 | 8.5476E-04 |
| 202122_s_at | M6PRBP1 | mannose-6-phosphate receptor binding protein 1 | NM_005817 | 8.6534E-04 |
| 221561_at | SOAT1 | sterol O-acyltransferase 1 | L21934 | 8.6953E-04 |
| 203119_at | CCDC86 | coiled-coil domain containing 86 | NM_024098 | 8.7851E-04 |
| 203431_s_at | RICS | Rho GTPase-activating protein | NM_014715 | 8.7902E-04 |
| 208699_x_at | TKT | transketolase | BF696840 | 8.8246E-04 |
| 206392_at | RARRES1 | retinoic acid receptor responder (tazarotene induced) 1 | NM_002888 | 8.8393E-04 |
| 210715_s_at | SPINT2 | serine peptidase inhibitor Kunitz type 2 | AF027205 | 8.9891E-04 |
| 200837_at | BCAP31 | B-cell receptor-associated protein 31 | NM_005745 | 9.0194E-04 |
| 209025_s_at | SYNCRIP | synaptotagmin binding cytoplasmic RNA interacting protein | AF037448 | 9.0260E-04 |
| 211047_x_at | AP2S1 | adaptor-related protein complex 2 sigma 1 subunit | BC006337 | 9.0723E-04 |

TABLE B-continued

| Probe Set ID | Gene Symbol | Gene Name | Representative Public ID | p value |
|---|---|---|---|---|
| 204942_s_at | ALDH3B2 | aldehyde dehydrogenase 3 family member B2 | NM_000695 | 9.1058E-04 |
| 208919_s_at | NADK | NAD kinase | BC001709 | 9.1552E-04 |
| 210074_at | CTSL2 | cathepsin L2 | AF070448 | 9.3602E-04 |
| 208963_x_at | FADS1 | fatty acid desaturase 1 | BG165833 | 9.5738E-04 |
| 208799_at | PSMB5 | proteasome (prosome macropain) subunit beta type 5 | BC004146 | 9.6091E-04 |
| 219429_at | FA2H | fatty acid 2-hydroxylase | NM_024306 | 9.6450E-04 |
| 36475_at | GCAT | glycine C-acetyltransferase (2-amino-3-ketobutyrate coenzyme A ligase) | Z97630 | 9.6676E-04 |
| 215093_at | NSDHL | NAD(P) dependent steroid dehydrogenase-like | U82671 | 9.6805E-04 |
| 215189_at | LOC100134394 | keratin 86 | X99142 | 9.7401E-04 |
| 209078_s_at | TXN2 | thioredoxin 2 | AF276920 | 9.7751E-04 |
| 208852_s_at | CANX | calnexin | AI761759 | 9.7992E-04 |
| 204253_s_at | VDR | vitamin D (125- dihydroxyvitamin D3) receptor | AA454701 | 9.8319E-04 |
| 209457_at | DUSP5 | dual specificity phosphatase 5 | U16996 | 9.9441E-04 |
| 207595_s_at | BMP1 | bone morphogenetic protein 1 | NM_006132 | 1.0199E-03 |
| 211752_s_at | NDUFS7 | NADH dehydrogenase (ubiquinone) Fe-S protein 7 20kDa (NADH-coenzyme Q reductase) | BC005954 | 1.0313E-03 |
| 219843_at | IPP | intracisternal A particle-promoted polypeptide | NM_005897 | 1.0419E-03 |
| 218582_at | MARCH5 | membrane-associated ring finger (C3HC4) 5 | NM_017824 | 1.0479E-03 |
| 201119_s_at | COX8A | cytochrome c oxidase subunit 8A (ubiquitous) | NM_004074 | 1.0583E-03 |
| 210334_x_at | BIRC5 | baculoviral IAP repeat-containing 5 | AB028869 | 1.0585E-03 |
| 201201_at | CSTB | cystatin B (stefin B) | NM_000100 | 1.0624E-03 |
| 207787_s_at | KRT33B | keratin 33B | NM_002279 | 1.0655E-03 |
| 208688_x_at | EIF3B | eukaryotic translation initiation factor 3 subunit B | U78525 | 1.1028E-03 |
| 201433_s_at | PTDSS1 | phosphatidylserine synthase 1 | NM_014754 | 1.1096E-03 |
| 91684_g_at | EXOSC4 | exosome component 4 | AI571298 | 1.1230E-03 |
| 213288_at | MBOAT2 | membrane bound O-acyltransferase domain containing 2 | AI761250 | 1.1339E-03 |
| 206074_s_at | HMGA1 | high mobility group AT-hook 1 | NM_002131 | 1.1423E-03 |
| 220486_x_at | LOC100130886 | hypothetical protein LOC100130886 | NM_017698 | 1.1621E-03 |
| 200734_s_at | ARF3 | ADP-ribosylation factor 3 | BG341906 | 1.1713E-03 |
| 203971_at | SLC31A1 | solute carrier family 31 (copper transporters) member 1 | NM_001859 | 1.1747E-03 |
| 201284_s_at | APEH | N-acylaminoacyl-peptide hydrolase | NM_001640 | 1.1833E-03 |
| 204014_at | DUSP4 | dual specificity phosphatase 4 | NM_001394 | 1.1864E-03 |
| 217806_s_at | POLDIP2 | polymerase (DNA-directed) delta interacting protein 2 | NM_015584 | 1.1923E-03 |
| 210236_at | PPFIA1 | protein tyrosine phosphatase receptor type f polypeptide (PTPRF) interacting protein (liprin) alpha 1 | U22815 | 1.2081E-03 |
| 208527_x_at | HIST1H2BG | histone cluster 1 H2bc | NM_003523 | 1.2099E-03 |
| 208962_s_at | FADS1 | fatty acid desaturase 1 | BE540552 | 1.2236E-03 |
| 206873_at | CA6 | carbonic anhydrase VI | NM_001215 | 1.2902E-03 |
| 212048_s_at | YARS | tyrosyl-tRNA synthetase | AW245400 | 1.3124E-03 |
| 205916_at | S100A7 | S100 calcium binding protein A7 | NM_002963 | 1.3187E-03 |
| 210655_s_at | FOXO3 | forkhead box O3 | AF041336 | 1.3616E-03 |
| 220163_s_at | HR | hairless homolog (mouse) | NM_018411 | 1.3692E-03 |
| 204836_at | GLDC | glycine dehydrogenase (decarboxylating) | NM_000170 | 1.4104E-03 |
| 202218_s_at | FADS2 | fatty acid desaturase 2 | NM_004265 | 1.4192E-03 |
| 214786_at | MAP3K1 | mitogen-activated protein kinase kinase kinase 1 | AA361361 | 1.4341E-03 |
| 211906_s_at | SERPINB4 | serpin peptidase inhibitor clade B (ovalbumin) member 4 | AB046400 | 1.4392E-03 |
| 220615_s_at | FAR2 | fatty acyl CoA reductase 2 | NM_018099 | 1.4407E-03 |
| 205759_s_at | SULT2B1 | sulfotransferase family cytosolic 2B member 1 | NM_004605 | 1.4410E-03 |
| 209605_at | TST | thiosulfate sulfurtransferase (rhodanese) | D87292 | 1.4493E-03 |
| 212218_s_at | FASN | fatty acid synthase | AI954041 | 1.4565E-03 |
| 206465_at | ACSBG1 | acyl-CoA synthetase bubblegum family member 1 | BE856376 | 1.4571E-03 |
| 205661_s_at | FLAD1 | FAD1 flavin adenine dinucleotide synthetase homolog (S. cerevisiae) | NM_025207 | 1.4794E-03 |
| 218062_x_at | CDC42EP4 | CDC42 effector protein (Rho GTPase binding) 4 | NM_012121 | 1.4836E-03 |
| 205783_at | KLK13 | kallikrein-related peptidase 13 | NM_015596 | 1.4883E-03 |
| 212807_s_at | SORT1 | sortilin 1 | BF447105 | 1.5110E-03 |
| 210816_s_at | CYB561 | cytochrome b-561 | BC000021 | 1.5129E-03 |
| 205856_at | SLC14A1 | solute carrier family 14 (urea transporter) member 1 (Kidd blood group) | NM_015865 | 1.5262E-03 |
| 204471_at | GAP43 | growth associated protein 43 | NM_002045 | 1.5287E-03 |
| 208708_x_at | EIF5 | eukaryotic translation initiation factor 5 | AL080102 | 1.5349E-03 |
| 202826_at | SPINT1 | serine peptidase inhibitor Kunitz type 1 | NM_003710 | 1.5419E-03 |
| 200971_s_at | SERP1 | stress-associated endoplasmic reticulum protein 1 | NM_014445 | 1.5589E-03 |
| 201695_s_at | NP | nucleoside phosphorylase | NM_000270 | 1.5658E-03 |
| 201760_s_at | WSB2 | WD repeat and SOCS box-containing 2 | NM_018639 | 1.5795E-03 |
| 209624_s_at | MCCC2 | methylcrotonoyl-Coenzyme A carboxylase 2 (beta) | AB050049 | 1.6326E-03 |
| 216396_s_at | EI24 | etoposide induced 2.4 mRNA | AF131850 | 1.6335E-03 |
| 209832_s_at | CDT1 | chromatin licensing and DNA replication factor 1 | AF321125 | 1.6426E-03 |
| 215066_at | PTPRF | protein tyrosine phosphatase receptor type F | AU158443 | 1.6528E-03 |
| 207114_at | LY6G6C | lymphocyte antigen 6 complex locus G6C | NM_025261 | 1.6553E-03 |
| 202671_s_at | PDXK | pyridoxal (pyridoxine vitamin B6) kinase | NM_003681 | 1.6560E-03 |
| 214665_s_at | CHP | calcium binding protein P22 | AK000095 | 1.6605E-03 |
| 219369_s_at | OTUB2 | OTU domain ubiquitin aldehyde binding 2 | NM_023112 | 1.6717E-03 |
| 219172_at | TRIM62 | tripartite motif-containing 62 | NM_018207 | 1.6780E-03 |
| 209093_s_at | GBA | glucosidase beta; acid (includes glucosylceramidase) | K02920 | 1.6857E-03 |
| 212088_at | PMPCA | peptidase (mitochondrial processing) alpha | BF570122 | 1.6997E-03 |
| 218580_x_at | AURKAIP1 | aurora kinase A interacting protein 1 | NM_017900 | 1.7063E-03 |
| 220972_s_at | KRTAP9-9 | keratin associated protein 9-4 | NM_030975 | 1.7166E-03 |
| 201274_at | PSMA5 | proteasome (prosome macropain) subunit alpha type 5 | NM_002790 | 1.7264E-03 |

TABLE B-continued

| Probe Set ID | Gene Symbol | Gene Name | Representative Public ID | p value |
|---|---|---|---|---|
| 202788_at | MAPKAPK3 | mitogen-activated protein kinase-activated protein kinase 3 | NM_004635 | 1.7807E-03 |
| 216641_s_at | LAD1 | ladinin 1 | U58994 | 1.7904E-03 |
| 201277_s_at | HNRNPAB | heterogeneous nuclear ribonucleoprotein A/B | NM_004499 | 1.7905E-03 |
| 205942_s_at | ACSM3 | acyl-CoA synthetase medium-chain family member 3 | NM_005622 | 1.7973E-03 |
| 217188_s_at | C14orf1 | chromosome 14 open reading frame 1 | AC007182 | 1.8045E-03 |
| 201879_at | ARIH1 | ariadne homolog ubiquitin-conjugating enzyme E2 binding protein 1 (Drosophila) | AI694332 | 1.8359E-03 |
| 200890_s_at | SSR1 | signal sequence receptor alpha | AW006345 | 1.8454E-03 |
| 210337_s_at | ACLY | ATP citrate lyase | U18197 | 1.8472E-03 |
| 208301_at |  | null | NM_025033 | 1.8565E-03 |
| 202831_at | GPX2 | glutathione peroxidase 2 (gastrointestinal) | NM_002083 | 1.8811E-03 |
| 208351_s_at | MAPK1 | mitogen-activated protein kinase 1 | NM_002745 | 1.8879E-03 |
| 202418_at | YIF1A | Yip1 interacting factor homolog A (S. cerevisiae) | NM_020470 | 1.9069E-03 |
| 216979_at | NR4A3 | nuclear receptor subfamily 4 group A member 3 | X89894 | 1.9090E-03 |
| 219980_at | C4orf29 | chromosome 4 open reading frame 29 | NM_025097 | 1.9117E-03 |
| 207457_s_at | LY6G6D | lymphocyte antigen 6 complex locus G6D | NM_021246 | 1.9129E-03 |
| 209885_at | RHOD | ras homolog gene family member D | BC001338 | 1.9191E-03 |
| 220431_at | TMPRSS11E | transmembrane protease serine 11E | NM_014058 | 1.9354E-03 |
| 213553_x_at | APOC1 | apolipoprotein C-I | W79394 | 1.9760E-03 |
| 200824_at | GSTP1 | glutathione S-transferase pi 1 | NM_000852 | 1.9764E-03 |
| 221934_s_at | LOC100133719 | DALR anticodon binding domain containing 3 | BF941492 | 1.9812E-03 |
| 206969_at | KRT34 | keratin 34 | NM_021013 | 1.9840E-03 |
| 213059_at | CREB3L1 | cAMP responsive element binding protein 3-like 1 | AF055009 | 1.9924E-03 |
| 218951_s_at | PLCXD1 | phosphatidylinositol-specific phospholipase C X domain containing 1 | NM_018390 | 1.9969E-03 |
| 219131_at | UBIAD1 | UbiA prenyltransferase domain containing 1 | NM_013319 | 2.0022E-03 |
| 39729_at | PRDX2 | peroxiredoxin 2 | L19185 | 2.0334E-03 |
| 220675_s_at | PNPLA3 | patatin-like phospholipase domain containing 3 | NM_025225 | 2.0480E-03 |
| 211695_x_at | MUC1 | mucin 1 cell surface associated | AF348143 | 2.0496E-03 |
| 206027_at | S100A3 | S100 calcium binding protein A3 | NM_002960 | 2.0599E-03 |
| 208660_at | CS | citrate synthase | BC000105 | 2.0731E-03 |
| 218018_at | PDXK | pyridoxal (pyridoxine vitamin B6) kinase | AW449022 | 2.0955E-03 |

TABLE C

| Probe set ID | Gene Symbol | Gene Name | Representative Public ID | p value |
|---|---|---|---|---|
| 205236_x_at | SOD3 | superoxide dismutase 3 extracellular | NM_003102 | 4.1207E-10 |
| 213247_at | SVEP1 | sushi von Willebrand factor type A EGF and pentraxin domain containing 1 | AA716107 | 5.1550E-10 |
| 212796_s_at | TBC1D2B | TBC1 domain family member 2B | BF195608 | 3.6373E-09 |
| 213113_s_at | SLC43A3 | solute carrier family 43 member 3 | AI630178 | 1.0187E-08 |
| 202510_s_at | TNFAIP2 | tumor necrosis factor alpha-induced protein 2 | NM_006291 | 2.4861E-08 |
| 213364_s_at | SNX1 | sorting nexin 1 | AI052536 | 2.7627E-08 |
| 202291_s_at | MGP | matrix Gla protein | NM_000900 | 6.9902E-08 |
| 219304_s_at | PDGFD | platelet derived growth factor D | NM_025208 | 7.2053E-08 |
| 213258_at | TFPI | tissue factor pathway inhibitor (lipoprotein-associated coagulation inhibitor) | BF511231 | 7.6953E-08 |
| 213071_at | DPT | dermatopontin | AL049798 | 8.6564E-08 |
| 202912_at | ADM | adrenomedullin | NM_001124 | 1.1154E-07 |
| 202363_at | SPOCK1 | sparc/osteonectin cwcv and kazal-like domains proteoglycan (testican) 1 | AF231124 | 1.3816E-07 |
| 212067_s_at | C1R | complement component 1 r subcomponent | AL573058 | 1.7318E-07 |
| 203088_at | FBLN5 | fibulin 5 | NM_006329 | 1.8181E-07 |
| 212589_at | RRAS2 | related RAS viral (r-ras) oncogene homolog 2 | AI753792 | 2.0143E-07 |
| 202994_s_at | FBLN1 | fibulin 1 | Z95331 | 2.4381E-07 |
| 213164_at | SLC5A3 | solute carrier family 5 (sodium/myo-inositol cotransporter) member 3 | AI867198 | 3.0577E-07 |
| 212761_at | TCF7L2 | transcription factor 7-like 2 (T-cell specific HMG-box) | AI949687 | 3.3288E-07 |
| 216620_s_at | ARHGEF10 | Rho guanine nucleotide exchange factor (GEF) 10 | AF009205 | 3.6027E-07 |
| 217800_s_at | NDFIP1 | Nedd4 family interacting protein 1 | NM_030571 | 3.8336E-07 |
| 206157_at | PTX3 | pentraxin-related gene rapidly induced by IL-1 beta | NM_002852 | 4.0587E-07 |
| 209763_at | CHRDL1 | chordin-like 1 | AL049176 | 4.1288E-07 |
| 207606_s_at | ARHGAP12 | Rho GTPase activating protein 12 | NM_018287 | 4.3253E-07 |
| 213348_at | CDKN1C | cyclin-dependent kinase inhibitor 1C (p57 Kip2) | N33167 | 4.6161E-07 |
| 208747_s_at | C1S | complement component 1 s subcomponent | M18767 | 4.8744E-07 |
| 213150_at | HOXA10 | homeobox A10 | BF792917 | 4.9645E-07 |
| 210155_at | MYOC | myocilin trabecular meshwork inducible glucocorticoid response | D88214 | 5.0664E-07 |
| 212558_at | SPRY1 | sprouty homolog 1 antagonist of FGF signaling (Drosophila) | BF508662 | 5.2222E-07 |
| 205794_s_at | NOVA1 | neuro-oncological ventral antigen 1 | NM_002515 | 5.5567E-07 |
| 200785_s_at | LOC100134190 | similar to low density lipoprotein-related protein 1 (alpha-2-macroglobulin receptor) | NM_002332 | 6.7345E-07 |
| 205422_s_at | ITGBL1 | integrin beta-like 1 (with EGF-like repeat domains) | NM_004791 | 6.8540E-07 |
| 204749_at | NAP1L3 | nucleosome assembly protein 1-like 3 | NM_004538 | 7.3357E-07 |
| 204963_at | SSPN | sarcospan (Kras oncogene-associated gene) | AL136756 | 7.4308E-07 |
| 220327_at | VGLL3 | vestigial like 3 (Drosophila) | NM_016206 | 9.2218E-07 |
| 217853_at | TNS3 | tensin 3 | NM_022748 | 9.6113E-07 |
| 213068_at | DPT | dermatopontin | AI146848 | 9.9396E-07 |

TABLE C-continued

| Probe set ID | Gene Symbol | Gene Name | Representative Public ID | p value |
|---|---|---|---|---|
| 212944_at | SLC5A3 | solute carrier family 5 (sodium/myo-inositol cotransporter) member 3 | AK024896 | 1.0012E-06 |
| 209335_at | DCN | decorin | AI281593 | 1.0494E-06 |
| 200986_at | SERPING1 | serpin peptidase inhibitor clade G (C1 inhibitor) member 1 | NM_000062 | 1.0535E-06 |
| 201842_s_at | EFEMP1 | EGF-containing fibulin-like extracellular matrix protein 1 | AI826799 | 1.1054E-06 |
| 212224_at | ALDH1A1 | aldehyde dehydrogenase 1 family member A1 | NM_000689 | 1.1206E-06 |
| 221950_at | EMX2 | empty spiracles homeobox 2 | AI478455 | 1.1299E-06 |
| 203939_at | NT5E | 5'-nucleotidase ecto (CD73) | NM_002526 | 1.1852E-06 |
| 217904_s_at | BACE1 | beta-site APP-cleaving enzyme 1 | NM_012104 | 1.2008E-06 |
| 213568_at | OSR2 | odd-skipped related 2 (Drosophila) | AI811298 | 1.2131E-06 |
| 212419_at | ZCCHC24 | zinc finger CCHC domain containing 24 | AA131324 | 1.2940E-06 |
| 204846_at | CP | ceruloplasmin (ferroxidase) | NM_000096 | 1.3807E-06 |
| 203217_s_at | ST3GAL5 | ST3 beta-galactoside alpha-23-sialyltransferase 5 | NM_003896 | 1.4759E-06 |
| 206373_at | ZIC1 | Zic family member 1 (odd-paired homolog Drosophila) | NM_003412 | 1.4967E-06 |
| 202897_at | SIRPA | signal-regulatory protein alpha | AB023430 | 1.6045E-06 |
| 201787_at | LOC100133843 | fibulin 1 | NM_001996 | 1.6142E-06 |
| 218505_at | WDR59 | WD repeat domain 59 | NM_024673 | 1.6525E-06 |
| 221019_s_at | COLEC12 | collectin sub-family member 12 | NM_030781 | 1.6596E-06 |
| 201744_s_at | LUM | lumican | NM_002345 | 1.7389E-06 |
| 220037_s_at | LYVE1 | lymphatic vessel endothelial hyaluronan receptor 1 | NM_016164 | 1.7506E-06 |
| 213429_at | BICC1 | bicaudal C homolog 1 (Drosophila) | AW025579 | 1.7710E-06 |
| 218901_at | PLSCR4 | phospholipid scramblase 4 | NM_020353 | 1.8289E-06 |
| 221016_s_at | TCF7L1 | transcription factor 7-like 1 (T-cell specific HMG-box) | NM_031283 | 1.8590E-06 |
| 213800_at | CFH | complement factor H | X04697 | 2.0989E-06 |
| 202995_s_at | FBLN1 | fibulin 1 | NM_006486 | 2.1038E-06 |
| 207977_s_at | DPT | dermatopontin | NM_001937 | 2.1423E-06 |
| 205612_at | MMRN1 | multimerin 1 | NM_007351 | 2.1544E-06 |
| 201811_x_at | SH3BP5 | SH3-domain binding protein 5 (BTK-associated) | NM_004844 | 2.2599E-06 |
| 201792_at | AEBP1 | AE binding protein 1 | NM_001129 | 2.2845E-06 |
| 202664_at | WIPF1 | WAS/WASL interacting protein family member 1 | AW058622 | 2.3077E-06 |
| 214494_s_at | SPG7 | spastic paraplegia 7 (pure and complicated autosomal recessive) | NM_005200 | 2.3371E-06 |
| 202729_s_at | LTBP1 | latent transforming growth factor beta binding protein 1 | NM_000627 | 2.3760E-06 |
| 201843_s_at | EFEMP1 | EGF-containing fibulin-like extracellular matrix protein 1 | NM_004105 | 2.4011E-06 |
| 218418_s_at | KANK2 | KN motif and ankyrin repeat domains 2 | NM_015493 | 2.4190E-06 |
| 205407_at | RECK | reversion-inducing-cysteine-rich protein with kazal motifs | NM_021111 | 2.4567E-06 |
| 210135_s_at | SHOX2 | short stature homeobox 2 | AF022654 | 2.4688E-06 |
| 215116_s_at | DNM1 | dynamin 1 | AF035321 | 2.5340E-06 |
| 221556_at | CDC14B | CDC14 cell division cycle 14 homolog B (S. cerevisiae) | BF792631 | 2.5893E-06 |
| 205011_at | VWA5A | von Willebrand factor A domain containing 5A | NM_014622 | 2.6449E-06 |
| 200771_at | LAMC1 | laminin gamma 1 (formerly LAMB2) | NM_002293 | 2.6594E-06 |
| 203083_at | THBS2 | thrombospondin 2 | NM_003247 | 2.7220E-06 |
| 201116_s_at | CPE | carboxypeptidase E | AI922855 | 2.7262E-06 |
| 205802_at | TRPC1 | transient receptor potential cation channel subfamily C member 1 | NM_003304 | 2.7777E-06 |
| 200945_s_at | SEC31A | SEC31 homolog A (S. cerevisiae) | NM_014933 | 2.8298E-06 |
| 203813_s_at | SLIT3 | slit homolog 3 (Drosophila) | NM_003062 | 2.9973E-06 |
| 200784_s_at | LOC100134190 | similar to low density lipoprotein-related protein 1 (alpha-2-macroglobulin receptor) | BF304759 | 3.1301E-06 |
| 201818_at | LPCAT1 | lysophosphatidylcholine acyltransferase 1 | NM_024830 | 3.1321E-06 |
| 205382_s_at | CFD | complement factor D (adipsin) | NM_001928 | 3.3053E-06 |
| 210105_s_at | FYN | FYN oncogene related to SRC FGR YES | M14333 | 3.3891E-06 |
| 221796_at | NTRK2 | neurotrophic tyrosine kinase receptor type 2 | AA707199 | 3.4378E-06 |
| 219173_at | MYO15B | myosin XVB pseudogene | NM_024957 | 3.4389E-06 |
| 218276_s_at | SAV1 | salvador homolog 1 (Drosophila) | NM_021818 | 3.5175E-06 |
| 211743_s_at | PRG2 | proteoglycan 2 bone marrow (natural killer cell activator eosinophil granule major basic protein) | BC005929 | 3.5818E-06 |
| 218162_at | OLFML3 | olfactomedin-like 3 | NM_020190 | 3.6798E-06 |
| 202202_s_at | LAMA4 | laminin alpha 4 | NM_002290 | 3.6835E-06 |
| 213249_at | FBXL7 | F-box and leucine-rich repeat protein 7 | AU145127 | 3.7131E-06 |
| 202220_at | KIAA0907 | KIAA0907 | NM_014949 | 3.8586E-06 |
| 212736_at | C16orf45 | chromosome 16 open reading frame 45 | BE299456 | 3.9881E-06 |
| 209550_at | NDN | necdin homolog (mouse) | U35139 | 4.0364E-06 |
| 213422_s_at | MXRA8 | matrix-remodelling associated 8 | AW888223 | 4.0854E-06 |
| 209568_s_at | RGL1 | ral guanine nucleotide dissociation stimulator-like 1 | AF186779 | 4.1032E-06 |
| 212713_at | MFAP4 | microfibrillar-associated protein 4 | R72286 | 4.2791E-06 |
| 203131_at | PDGFRA | platelet-derived growth factor receptor alpha polypeptide | NM_006206 | 4.2993E-06 |
| 204140_at | TPST1 | tyrosylprotein sulfotransferase 1 | NM_003596 | 4.4001E-06 |
| 209265_s_at | METTL3 | methyltransferase like 3 | BC001650 | 4.6265E-06 |
| 218715_at | UTP6 | UTP6 small subunit (SSU) processome component homolog (yeast) | NM_018428 | 4.6383E-06 |
| 204671_s_at | ANKRD6 | ankyrin repeat domain 6 | BE677131 | 4.7769E-06 |
| 201535_at | UBL3 | ubiquitin-like 3 | NM_007106 | 4.8034E-06 |
| 218146_at | GLT8D1 | glycosyltransferase 8 domain containing 1 | NM_018446 | 4.8282E-06 |
| 204042_at | WASF3 | WAS protein family member 3 | AB020707 | 4.8795E-06 |
| 204345_at | COL16A1 | collagen type XVI alpha 1 | NM_001856 | 4.9731E-06 |
| 216033_s_at | FYN | FYN oncogene related to SRC FGR YES | S74774 | 5.0274E-06 |
| 36030_at | IFFO1 | intermediate filament family orphan 1 | AL080214 | 5.0956E-06 |
| 218718_at | PDGFC | platelet derived growth factor C | NM_016205 | 5.1266E-06 |
| 203706_s_at | FZD7 | frizzled homolog 7 (Drosophila) | NM_003507 | 5.4817E-06 |
| 219093_at | PID1 | phosphotyrosine interaction domain containing 1 | NM_017933 | 5.7633E-06 |

TABLE C-continued

| Probe set ID | Gene Symbol | Gene Name | Representative Public ID | p value |
|---|---|---|---|---|
| 203583_at | UNC50 | unc-50 homolog (*C. elegans*) | NM_014044 | 5.7712E-06 |
| 205609_at | ANGPT1 | angiopoietin 1 | NM_001146 | 5.7795E-06 |
| 204457_s_at | GAS1 | growth arrest-specific 1 | NM_002048 | 5.7891E-06 |
| 205083_at | AOX1 | aldehyde oxidase 1 | NM_001159 | 5.9671E-06 |
| 203812_at | | null | AB011538 | 6.2204E-06 |
| 212621_at | TMEM194A | transmembrane protein 194A | AB006624 | 6.3362E-06 |
| 206404_at | FGF9 | fibroblast growth factor 9 (glia-activating factor) | NM_002010 | 6.5054E-06 |
| 204606_at | CCL21 | chemokine (C-C motif) ligand 21 | NM_002989 | 6.5807E-06 |
| 201117_s_at | CPE | carboxypeptidase E | NM_001873 | 6.8179E-06 |
| 213802_at | | null | AI810767 | 7.0439E-06 |
| 212486_s_at | FYN | FYN oncogene related to SRC FGR YES | N20923 | 7.2524E-06 |
| 201278_at | DAB2 | disabled homolog 2 mitogen-responsive phosphoprotein (*Drosophila*) | N21202 | 7.7092E-06 |
| 218656_s_at | LHFP | lipoma HMGIC fusion partner | NM_005780 | 7.9930E-06 |
| 212230_at | PPAP2B | phosphatidic acid phosphatase type 2B | AV725664 | 8.1114E-06 |
| 221760_at | MAN1A1 | CDNA: FLJ21946 fis clone HEP04860 highly similar to HSHUMM9 *Homo sapiens* HUMM9 mRNA | BG287153 | 8.1833E-06 |
| 210139_s_at | PMP22 | peripheral myelin protein 22 | L03203 | 8.8249E-06 |
| 212877_at | KLC1 | kinesin light chain 1 | AA284075 | 9.1329E-06 |
| 217767_at | C3 | complement component 3 | NM_000064 | 9.1495E-06 |
| 212503_s_at | DIP2C | DIP2 disco-interacting protein 2 homolog C (*Drosophila*) | N22859 | 9.3817E-06 |
| 218204_s_at | FYCO1 | FYVE and coiled-coil domain containing 1 | NM_024513 | 9.6526E-06 |
| 212793_at | DAAM2 | dishevelled associated activator of morphogenesis 2 | BF513244 | 1.0235E-05 |
| 202920_at | ANK2 | ankyrin 2 neuronal | BF726212 | 1.0636E-05 |
| 203476_at | TPBG | trophoblast glycoprotein | NM_006670 | 1.0681E-05 |
| 217122_s_at | LOC728661 | similar to solute carrier family 35 member E2 | AL031282 | 1.0828E-05 |
| 211896_s_at | DCN | decorin | AF138302 | 1.0835E-05 |
| 204453_at | ZNF84 | zinc finger protein 84 | NM_003428 | 1.0897E-05 |
| 211535_s_at | FGFR1 | fibroblast growth factor receptor 1 | M60485 | 1.1017E-05 |
| 211548_s_at | HPGD | hydroxyprostaglandin dehydrogenase 15-(NAD) | J05594 | 1.1089E-05 |
| 213880_at | LGR5 | leucine-rich repeat-containing G protein-coupled receptor 5 | AL524520 | 1.1094E-05 |
| 202273_at | PDGFRB | platelet-derived growth factor receptor beta polypeptide | NM_002609 | 1.1180E-05 |
| 207808_s_at | PROS1 | protein S (alpha) | NM_000313 | 1.1272E-05 |
| 220744_s_at | IFT122 | intraflagellar transport 122 homolog (*Chlamydomonas*) | NM_018262 | 1.2426E-05 |
| 205542_at | STEAP1 | six transmembrane epithelial antigen of the prostate 1 | NM_012449 | 1.2639E-05 |
| 205933_at | SETBP1 | SET binding protein 1 | NM_015559 | 1.2646E-05 |
| 214323_s_at | UPF3A | UPF3 regulator of nonsense transcripts homolog A (yeast) | N36842 | 1.2818E-05 |
| 212597_s_at | HMGXB4 | HMG box domain containing 4 | AL079310 | 1.2979E-05 |
| 204112_s_at | HNMT | histamine N-methyltransferase | NM_006895 | 1.3109E-05 |
| 213652_at | PCSK5 | Protease PC6 isoform A (PCSK5) | AU152579 | 1.3167E-05 |
| 215388_s_at | CFH | complement factor H | X56210 | 1.3176E-05 |
| 204036_at | LPAR1 | lysophosphatidic acid receptor 1 | AW269335 | 1.3211E-05 |
| 209884_s_at | SLC4A7 | solute carrier family 4 sodium bicarbonate cotransporter member 7 | AF047033 | 1.4144E-05 |
| 205452_at | PIGB | phosphatidylinositol glycan anchor biosynthesis class B | NM_004855 | 1.4354E-05 |
| 207177_at | PTGFR | prostaglandin F receptor (FP) | NM_000959 | 1.4808E-05 |
| 219059_s_at | LYVE1 | lymphatic vessel endothelial hyaluronan receptor 1 | AL574194 | 1.4902E-05 |
| 201150_s_at | TIMP3 | TIMP metallopeptidase inhibitor 3 | NM_000362 | 1.4957E-05 |
| 200770_s_at | LAMC1 | laminin gamma 1 (formerly LAMB2) | J03202 | 1.5246E-05 |
| 212327_at | LIMCH1 | LIM and calponin homology domains 1 | AK026815 | 1.6143E-05 |
| 206958_s_at | UPF3A | UPF3 regulator of nonsense transcripts homolog A (yeast) | AF318575 | 1.6235E-05 |
| 39650_s_at | PCNXL2 | pecanex-like 2 (*Drosophila*) | AB007895 | 1.6512E-05 |
| 207417_s_at | ZNF177 | zinc finger protein 177 | NM_003451 | 1.6676E-05 |
| 213293_s_at | TRIM22 | tripartite motif-containing 22 | AA083478 | 1.6798E-05 |
| 218686_at | RHBDF1 | rhomboid 5 homolog 1 (*Drosophila*) | NM_022450 | 1.7255E-05 |
| 212195_at | IL6ST | interleukin 6 signal transducer (gp130 oncostatin M receptor) | AL049265 | 1.7471E-05 |
| 202598_at | S100A13 | S100 calcium binding protein A13 | NM_005979 | 1.7872E-05 |
| 203893_at | TAF9 | TAF9 RNA polymerase II TATA box binding protein (TBP)-associated factor 32kDa | NM_016283 | 1.7916E-05 |
| 218093_s_at | ANKRD10 | ankyrin repeat domain 10 | NM_017664 | 1.8440E-05 |
| 216840_s_at | LAMA2 | laminin alpha 2 | AK026829 | 1.8901E-05 |
| 219552_at | SVEP1 | sushi von Willebrand factor type A EGF and pentraxin domain containing 1 | NM_024500 | 1.9057E-05 |
| 203914_x_at | HPGD | hydroxyprostaglandin dehydrogenase 15-(NAD) | NM_000860 | 1.9929E-05 |
| 218793_s_at | SCML1 | sex comb on midleg-like 1 (*Drosophila*) | NM_006746 | 2.0086E-05 |
| 209612_s_at | ADH1B | alcohol dehydrogenase 1B (class I) beta polypeptide | M24317 | 2.0211E-05 |
| 209580_s_at | MBD4 | methyl-CpG binding domain protein 4 | AF114784 | 2.0320E-05 |
| 221897_at | TRIM52 | tripartite motif-containing 52 | AA205660 | 2.0818E-05 |
| 219283_at | C1GALT1C1 | C1GALT1-specific chaperone 1 | NM_014158 | 2.1265E-05 |
| 202478_at | TRIB2 | tribbles homolog 2 (*Drosophila*) | NM_021643 | 2.1280E-05 |
| 214703_s_at | MAN2B2 | mannosidase alpha class 2B member 2 | AW954107 | 2.1437E-05 |
| 59375_at | MYO15B | myosin XVB pseudogene | AI825877 | 2.1605E-05 |
| 204719_at | ABCA8 | ATP-binding cassette sub-family A (ABC1) member 8 | NM_007168 | 2.1721E-05 |
| 211675_s_at | MDFIC | MyoD family inhibitor domain containing | AF054589 | 2.1807E-05 |
| 213161_at | C9orf97 | chromosome 9 open reading frame 97 | AI583393 | 2.2081E-05 |
| 202951_at | STK38 | serine/threonine kinase 38 | BE048506 | 2.2195E-05 |
| 213519_s_at | LAMA2 | laminin alpha 2 | AI078169 | 2.2351E-05 |
| 209409_at | GRB10 | growth factor receptor-bound protein 10 | D86962 | 2.2881E-05 |
| 201034_at | ADD3 | adducin 3 (gamma) | BE545756 | 2.3091E-05 |
| 206227_at | CILP | cartilage intermediate layer protein nucleotide pyrophosphohydrolase | NM_003613 | 2.3220E-05 |

TABLE C-continued

| Probe set ID | Gene Symbol | Gene Name | Representative Public ID | p value |
|---|---|---|---|---|
| 212651_at | RHOBTB1 | Rho-related BTB domain containing 1 | AB018283 | 2.3246E-05 |
| 215016_x_at | DST | dystonin | BC004912 | 2.3884E-05 |
| 212958_x_at | PAM | peptidylglycine alpha-amidating monooxygenase | AI022882 | 2.4348E-05 |
| 219949_at | LRRC2 | leucine rich repeat containing 2 | NM_024512 | 2.4451E-05 |
| 219639_x_at | PARP6 | poly (ADP-ribose) polymerase family member 6 | NM_020213 | 2.4585E-05 |
| 220992_s_at | C1orf25 | chromosome 1 open reading frame 25 | NM_030934 | 2.4860E-05 |
| 203600_s_at | C4orf8 | chromosome 4 open reading frame 8 | NM_003704 | 2.5273E-05 |
| 219729_at | PRRX2 | paired related homeobox 2 | NM_016307 | 2.5432E-05 |
| 212855_at | DCUN1D4 | DCN1 defective in cullin neddylation 1 domain containing 4 (*S. cerevisiae*) | D87466 | 2.5564E-05 |
| 212328_at | LIMCH1 | LIM and calponin homology domains 1 | AB029025 | 2.6031E-05 |
| 201395_at | RBM5 | RNA binding motif protein 5 | NM_005778 | 2.6282E-05 |
| 203139_at | DAPK1 | death-associated protein kinase 1 | NM_004938 | 2.6335E-05 |
| 222043_at | CLU | clusterin | AI982754 | 2.6684E-05 |
| 203886_s_at | FBLN2 | fibulin 2 | NM_001998 | 2.7202E-05 |
| 212979_s_at | FAM115A | family with sequence similarity 115 member A | AW293343 | 2.7293E-05 |
| 209220_at | GPC3 | glypican 3 | L47125 | 2.7421E-05 |
| 212148_at | PBX1 | pre-B-cell leukemia homeobox 1 | AL049381 | 2.7560E-05 |
| 202142_at | COPS8 | COP9 constitutive photomorphogenic homolog subunit 8 (*Arabidopsis*) | BC003090 | 2.7754E-05 |
| 222235_s_at | CSGALNACT2 | chondroitin sulfate N-acetylgalactosaminyltransferase 2 | AL139812 | 2.8031E-05 |
| 212764_at | ZEB1 | zinc finger E-box binding homeobox 1 | AI806174 | 2.8104E-05 |
| 214749_s_at | ARMCX6 | armadillo repeat containing X-linked 6 | AK000818 | 2.8574E-05 |
| 201944_at | HEXB | hexosaminidase B (beta polypeptide) | NM_000521 | 2.8860E-05 |
| 205515_at | PRSS12 | protease serine 12 (neurotrypsin motopsin) | NM_003619 | 2.8866E-05 |
| 213698_at | LOC100130633 | similar to ZMYM6 protein | AI805560 | 2.8874E-05 |
| 203824_at | TSPAN8 | tetraspanin 8 | NM_004616 | 2.9175E-05 |
| 203117_s_at | PAN2 | PAN2 poly(A) specific ribonuclease subunit homolog (*S. cerevisiae*) | NM_014871 | 3.0053E-05 |
| 204605_at | CGRRF1 | cell growth regulator with ring finger domain 1 | NM_006568 | 3.0162E-05 |
| 219778_at | ZFPM2 | zinc finger protein multitype 2 | NM_012082 | 3.0400E-05 |
| 217892_s_at | LIMA1 | LIM domain and actin binding 1 | NM_016357 | 3.0815E-05 |
| 212681_at | EPB41L3 | erythrocyte membrane protein band 4.1-like 3 | AI770004 | 3.0884E-05 |
| 204085_s_at | CLN5 | ceroid-lipofuscinosis neuronal 5 | NM_006493 | 3.0907E-05 |
| 210102_at | VWA5A | von Willebrand factor A domain containing 5A | BC001234 | 3.0936E-05 |
| 220351_at | CCRL1 | chemokine (C-C motif) receptor-like 1 | NM_016557 | 3.1140E-05 |
| 210406_s_at | RAB6A | RAB6A member RAS oncogene family | AL136727 | 3.1167E-05 |
| 221569_at | AHI1 | Abelson helper integration site 1 | AL136797 | 3.1574E-05 |
| 219550_at | ROBO3 | roundabout axon guidance receptor homolog 3 (*Drosophila*) | NM_022370 | 3.1855E-05 |
| 200762_at | DPYSL2 | dihydropyrimidinase-like 2 | NM_001386 | 3.1884E-05 |
| 201086_x_at | SON | SON DNA binding protein | NM_003103 | 3.2222E-05 |
| 218285_at | BDH2 | 3-hydroxybutyrate dehydrogenase type 2 | NM_020139 | 3.2876E-05 |
| 213397_x_at | RNASE4 | ribonuclease RNase A family 4 | AI761728 | 3.3089E-05 |
| 219908_at | DKK2 | dickkopf homolog 2 (Xenopus laevis) | NM_014421 | 3.4237E-05 |
| 213262_at | SACS | spastic ataxia of Charlevoix-Saguenay (sacsin) | AI932370 | 3.4386E-05 |
| 208944_at | TGFBR2 | transforming growth factor beta receptor II (70/80kDa) | D50683 | 3.4404E-05 |
| 209946_at | VEGFC | vascular endothelial growth factor C | U58111 | 3.4474E-05 |
| 219700_at | PLXDC1 | plexin domain containing 1 | NM_020405 | 3.4923E-05 |
| 213737_x_at | GOLGA9P | golgi autoantigen golgin subfamily a 9 pseudogene | AI620911 | 3.5009E-05 |
| 201669_s_at | MARCKS | myristoylated alanine-rich protein kinase C substrate | NM_002356 | 3.5037E-05 |
| 204897_at | PTGER4 | prostaglandin E receptor 4 (subtype EP4) | AA897516 | 3.5257E-05 |
| 220642_x_at | GPR89B | G protein-coupled receptor 89A | NM_016334 | 3.5976E-05 |
| 206159_at | GDF10 | growth differentiation factor 10 | NM_004962 | 3.6140E-05 |
| 201798_s_at | MYOF | myoferlin | NM_013451 | 3.7082E-05 |
| 215000_s_at | FEZ2 | fasciculation and elongation protein zeta 2 (zygin II) | AL117593 | 3.7115E-05 |
| 212985_at | APBB2 | amyloid beta (A4) precursor protein-binding family B member 2 | BF115739 | 3.7441E-05 |
| 209101_at | CTGF | connective tissue growth factor | M92934 | 3.7465E-05 |
| 221447_s_at | GLT8D2 | glycosyltransferase 8 domain containing 2 | NM_031302 | 3.7495E-05 |
| 218303_x_at | KRCC1 | lysine-rich coiled-coil 1 | NM_016618 | 3.7642E-05 |
| 203241_at | UVRAG | UV radiation resistance associated gene | NM_003369 | 3.7762E-05 |
| 209659_s_at | CDC16 | cell division cycle 16 homolog (*S. cerevisiae*) | AF164598 | 3.8581E-05 |
| 216321_s_at | NR3C1 | nuclear receptor subfamily 3 group C member 1 (glucocorticoid receptor) | X03348 | 3.8658E-05 |
| 201063_at | RCN1 | reticulocalbin 1 EF-hand calcium binding domain | NM_002901 | 3.8695E-05 |
| 202304_at | FNDC3A | fibronectin type III domain containing 3A | NM_014923 | 3.9178E-05 |
| 206484_s_at | XPNPEP2 | X-prolyl aminopeptidase (aminopeptidase P) 2 membrane-bound | NM_003399 | 3.9464E-05 |
| 210312_s_at | IFT20 | intraflagellar transport 20 homolog (*Chlamydomonas*) | BC002640 | 4.0492E-05 |
| 220065_at | TNMD | tenomodulin | NM_022144 | 4.0580E-05 |
| 209356_x_at | EFEMP2 | EGF-containing fibulin-like extracellular matrix protein 2 | AB030655 | 4.0584E-05 |
| 202336_s_at | PAM | peptidylglycine alpha-amidating monooxygenase | NM_000919 | 4.0770E-05 |
| 208669_s_at | EID1 | EP300 interacting inhibitor of differentiation 1 | AF109873 | 4.1682E-05 |
| 202446_s_at | PLSCR1 | phospholipid scramblase 1 | AI825926 | 4.1757E-05 |
| 209497_s_at | RBM4B | RNA binding motif protein 4B | BC003503 | 4.1986E-05 |
| 201139_s_at | SSB | Sjogren syndrome antigen B (autoantigen La) | NM_003142 | 4.2098E-05 |
| 212169_at | FKBP9 | FK506 binding protein 9 63 kDa | AL050187 | 4.2116E-05 |
| 201753_s_at | ADD3 | adducin 3 (gamma) | NM_019903 | 4.2645E-05 |
| 217525_at | OLFML1 | olfactomedin-like 1 | AW305097 | 4.2856E-05 |
| 218616_at | INTS12 | integrator complex subunit 12 | NM_020395 | 4.3996E-05 |
| 205100_at | GFPT2 | glutamine-fructose-6-phosphate transaminase 2 | NM_005110 | 4.4073E-05 |
| 218801_at | UGCGL2 | UDP-glucose ceramide glucosyltransferase-like 2 | NM_020121 | 4.4535E-05 |
| 201398_s_at | TRAM1 | translocation associated membrane protein 1 | BC000687 | 4.4699E-05 |

TABLE C-continued

| Probe set ID | Gene Symbol | Gene Name | Representative Public ID | p value |
|---|---|---|---|---|
| 213455_at | FAM114A1 | family with sequence similarity 114 member A1 | W87466 | 4.4874E-05 |
| 219493_at | SHCBP1 | SHC SH2-domain binding protein 1 | NM_024745 | 4.5019E-05 |
| 219073_s_at | OSBPL10 | oxysterol binding protein-like 10 | NM_017784 | 4.5703E-05 |
| 216044_x_at | FAM69A | family with sequence similarity 69 member A | AK027146 | 4.6409E-05 |
| 208986_at | TCF12 | transcription factor 12 | AL559478 | 4.6942E-05 |
| 205792_at | WISP2 | WNT1 inducible signaling pathway protein 2 | NM_003881 | 4.7104E-05 |
| 204735_at | PDE4A | phosphodiesterase 4A cAMP-specific (phosphodiesterase E2 dunce homolog Drosophila) | NM_006202 | 4.7153E-05 |
| 202382_s_at | GNPDA1 | glucosamine-6-phosphate deaminase 1 | NM_005471 | 4.7273E-05 |
| 214434_at | HSPA12A | heat shock 70kDa protein 12A | AB007877 | 4.8185E-05 |
| 211864_s_at | MYOF | myoferlin | AF207990 | 4.9709E-05 |
| 211719_x_at | FN1 | fibronectin 1 | BC005858 | 5.0797E-05 |
| 205728_at |  | null | AL022718 | 5.1523E-05 |
| 218885_s_at | GALNT12 | UDP-N-acetyl-alpha-D-galactosamine:polypeptide N-acetylgalactosaminyl transferase 12 (GalNAc-T12) | NM_024642 | 5.1829E-05 |
| 218076_s_at | ARHGAP17 | Rho GTPase activating protein 17 | NM_018054 | 5.2424E-05 |
| 217792_at | SNX5 | sorting nexin 5 | NM_014426 | 5.2561E-05 |
| 212779_at | KIAA1109 | KIAA1109 | AB029032 | 5.2993E-05 |
| 212254_s_at | DST | dystonin | AI798790 | 5.3772E-05 |
| 202863_at | SP100 | SP100 nuclear antigen | NM_003113 | 5.4231E-05 |
| 218084_x_at | FXYD5 | FXYD domain containing ion transport regulator 5 | NM_014164 | 5.4271E-05 |
| 205573_s_at | SNX7 | sorting nexin 7 | NM_015976 | 5.4748E-05 |
| 221020_s_at | SLC25A32 | solute carrier family 25 member 32 | NM_030780 | 5.5194E-05 |
| 202104_s_at | SPG7 | spastic paraplegia 7 (pure and complicated autosomal recessive) | NM_003119 | 5.5970E-05 |
| 201780_s_at | RNF13 | ring finger protein 13 | NM_007282 | 5.6181E-05 |
| 204093_at | CCNH | cyclin H | NM_001239 | 5.6217E-05 |
| 208016_s_at | AGTR1 | angiotensin II receptor type 1 | NM_004835 | 5.6967E-05 |
| 221773_at | ELK3 | ELK3 ETS-domain protein (SRF accessory protein 2) mRNA (cDNA clone MGC:13551 IMAGE:4287696) | AW575374 | 5.7036E-05 |
| 213392_at | IQCK | IQ motif containing K | AW070229 | 5.7402E-05 |
| 212798_s_at | ANKMY2 | ankyrin repeat and MYND domain containing 2 | AK001389 | 5.7754E-05 |
| 221645_s_at | ZNF83 | zinc finger protein 83 | M27877 | 5.9654E-05 |
| 218999_at | TMEM140 | transmembrane protein 140 | NM_018295 | 5.9756E-05 |
| 203799_at | CD302 | CD302 molecule | NM_014880 | 5.9942E-05 |
| 214093_s_at | FUBP1 | far upstream element (FUSE) binding protein 1 | AA156865 | 6.0566E-05 |
| 202958_at | PTPN9 | protein tyrosine phosphatase non-receptor type 9 | NM_002833 | 6.1062E-05 |
| 203903_s_at | HEPH | hephaestin | NM_014799 | 6.1829E-05 |
| 210495_x_at | FN1 | fibronectin 1 | AF130095 | 6.1983E-05 |
| 218007_s_at | RPS27L | ribosomal protein S27-like | NM_015920 | 6.2147E-05 |
| 205139_s_at | UST | uronyl-2-sulfotransferase | NM_005715 | 6.2337E-05 |

TABLE D

| Probe set ID | Gene Symbol | Gene Name | Representative Public ID | p value |
|---|---|---|---|---|
| 212291_at | HIPK1 | homeodomain interacting protein kinase 1 | AI393355 | 1.4712E-08 |
| 205187_at | SMAD5 | SMAD family member 5 | AF010601 | 2.3661E-08 |
| 216022_at |  | null | AL049278 | 1.5264E-07 |
| 211074_at | FOLR1 | folate receptor 1 (adult) | AF000381 | 2.3573E-07 |
| 208711_s_at | CCND1 | cyclin D1 | BC000076 | 2.4510E-07 |
| 214265_at | ITGA8 | integrin alpha 8 | AI193623 | 3.5683E-07 |
| 202102_s_at | BRD4 | bromodomain containing 4 | BF718610 | 4.5386E-07 |
| 222024_s_at | AKAP13 | A kinase (PRKA) anchor protein 13 | AK022014 | 6.8737E-07 |
| 210717_at |  | null | AF116659 | 8.8389E-07 |
| 211081_s_at | MAP4K5 | mitogen-activated protein kinase kinase kinase kinase 5 | Z25426 | 1.0560E-06 |
| 215024_at | C7orf28B | chromosome 7 open reading frame 28B | AK000993 | 1.0617E-06 |
| 209936_at | RBM5 | RNA binding motif protein 5 | AF107493 | 1.2081E-06 |
| 206061_s_at | DICER1 | dicer 1 ribonuclease type III | NM_030621 | 1.5719E-06 |
| 217649_at | ZFAND5 | zinc finger AN1-type domain 5 | AV702306 | 1.6384E-06 |
| 216858_x_at |  | null | AL080112 | 2.8178E-06 |
| 220071_x_at | CEP27 | centrosomal protein 27kDa | NM_018097 | 2.8584E-06 |
| 216187_x_at |  | null | AF222691 | 2.8639E-06 |
| 214041_x_at | RPL37A | Ribosomal protein L37a | BE857772 | 2.9005E-06 |
| 209088_s_at | UBN1 | ubinuclein 1 | T70262 | 3.0772E-06 |
| 210807_s_at | SLC16A7 | solute carrier family 16 member 7 (monocarboxylic acid transporter 2) | AF049608 | 3.7623E-06 |
| 214153_at | ELOVL5 | ELOVL family member 5 elongation of long chain fatty acids (FEN1/Elo2 SUR4/Elo3-like yeast) | BE467941 | 3.8401E-06 |
| 212057_at | KIAA0182 | KIAA0182 | AA206161 | 3.8589E-06 |
| 213718_at | RBM4 | RNA binding motif protein 4 | BE222257 | 3.9440E-06 |
| 207291_at | PRRG4 | proline rich Gla (G-carboxyglutamic acid) 4 (transmembrane) | NM_024081 | 4.4222E-06 |
| 203742_s_at | LOC645233 | thymine-DNA glycosylase pseudogene | BF674842 | 4.5161E-06 |
| 221943_x_at | RPL38 | Ribosomal protein L38 mRNA (cDNA clone MGC:1637 IMAGE:3346447) | AW303136 | 4.7760E-06 |
| 204881_s_at | UGCG | UDP-glucose ceramide glucosyltransferase | NM_003358 | 4.9560E-06 |

TABLE D-continued

| Probe set ID | Gene Symbol | Gene Name | Representative Public ID | p value |
|---|---|---|---|---|
| 206036_s_at | REL | v-rel reticuloendotheliosis viral oncogene homolog (avian) | NM_002908 | 5.0576E-06 |
| 202940_at | WNK1 | KIAA0344 gene | NM_014823 | 5.0700E-06 |
| 217538_at | SGSM2 | small G protein signaling modulator 2 | BF347113 | 5.3480E-06 |
| 212492_s_at | JMJD2B | jumonji domain containing 2B | AW237172 | 5.3779E-06 |
| 211503_s_at | RAB14 | RAB14 member RAS oncogene family | AF112206 | 6.0532E-06 |
| 203803_at | PCYOX1 | prenylcysteine oxidase 1 | N45309 | 6.5416E-06 |
| 211993_at | WNK1 | WNK lysine deficient protein kinase 1 | AI768512 | 6.7386E-06 |
| 202040_s_at | JARID1A | jumonji AT rich interactive domain 1A | NM_005056 | 6.7560E-06 |
| 214807_at | | null | AI278204 | 7.1860E-06 |
| 201195_s_at | SLC7A5 | solute carrier family 7 (cationic amino acid transporter y+ system) member 5 | AB018009 | 7.2298E-06 |
| 213517_at | PCBP2 | poly(rC) binding protein 2 | AW103422 | 7.3423E-06 |
| 201299_s_at | MOBKL1B | MOB1 Mps One Binder kinase activator-like 1B (yeast) | NM_018221 | 7.3742E-06 |
| 63825_at | ABHD2 | abhydrolase domain containing 2 | AI557319 | 7.6414E-06 |
| 214902_x_at | | null | AL080232 | 7.8481E-06 |
| 221664_s_at | F11R | F11 receptor | AF154005 | 8.1916E-06 |
| 212659_s_at | IL1RN | interleukin 1 receptor antagonist | AW083357 | 8.3955E-06 |
| 219024_at | PLEKHA1 | pleckstrin homology domain containing family A (phosphoinositide binding specific) member 1 | NM_021622 | 8.6942E-06 |
| 204524_at | PDPK1 | 3-phosphoinositide dependent protein kinase-1 | NM_002613 | 9.1327E-06 |
| 203318_s_at | ZNF148 | zinc finger protein 148 | NM_021964 | 9.1431E-06 |
| 213229_at | DICER1 | dicer 1 ribonuclease type III | BF590131 | 9.7278E-06 |
| 214422_at | LOC131185 | similar to RAD23B protein | T93562 | 9.7480E-06 |
| 209945_s_at | GSK3B | glycogen synthase kinase 3 beta | BC000251 | 1.0201E-05 |
| 205322_at | MTF1 | metal-regulatory transcription factor 1 | AW182367 | 1.0323E-05 |
| 204181_s_at | ZBTB43 | zinc finger and BTB domain containing 43 | T90308 | 1.0792E-05 |
| 203321_s_at | ADNP2 | ADNP homeobox 2 | AK022688 | 1.1043E-05 |
| 201901_s_at | YY1 | YY1 transcription factor | Z14077 | 1.1154E-05 |
| 212525_at | H2AFX | H2A histone family member X | AA760862 | 1.1321E-05 |
| 201917_s_at | SLC25A36 | solute carrier family 25 member 36 | AI694452 | 1.1789E-05 |
| 211337_s_at | TUBGCP4 | tubulin gamma complex associated protein 4 | BC000966 | 1.1823E-05 |
| 215179_x_at | PGF | Placenta growth factor 2 (PlGF-2) | AK023843 | 1.2046E-05 |
| 205967_at | HIST1H4A | histone cluster 1 H4a | NM_003542 | 1.2155E-05 |
| 210943_s_at | LYST | lysosomal trafficking regulator | U84744 | 1.2287E-05 |
| 221753_at | SSH1 | slingshot homolog 1 (*Drosophila*) | AI651213 | 1.2405E-05 |
| 221705_s_at | SIKE | suppressor of IKK epsilon | BC005934 | 1.3958E-05 |
| 215892_at | ZNF440 | Zinc finger protein 440 mRNA (cDNA clone MGC:46665 IMAGE:5556302) | AK021474 | 1.4065E-05 |
| 208624_s_at | EIF4G1 | eukaryotic translation initiation factor 4 gamma 1 | BE966878 | 1.4201E-05 |
| 208610_s_at | SRRM2 | serine/arginine repetitive matrix 2 | AI655799 | 1.4389E-05 |
| 222366_at | | null | W86781 | 1.4392E-05 |
| 220085_at | HELLS | helicase lymphoid-specific | NM_018063 | 1.4498E-05 |
| 207657_x_at | TNPO1 | transportin 1 | NM_002270 | 1.4524E-05 |
| 214815_at | TRIM33 | tripartite motif-containing 33 | AU136587 | 1.5331E-05 |
| 212520_s_at | SMARCA4 | SWI/SNF related matrix associated actin dependent regulator of chromatin subfamily a member 4 | AI684141 | 1.5496E-05 |
| 221986_s_at | KLHL24 | kelch-like 24 (*Drosophila*) | AW006750 | 1.5586E-05 |
| 217007_s_at | ADAM15 | ADAM metallopeptidase domain 15 | AK000667 | 1.5851E-05 |
| 210479_s_at | RORA | RAR-related orphan receptor A | L14611 | 1.6006E-05 |
| 204021_s_at | PURA | purine-rich element binding protein A | NM_005859 | 1.7428E-05 |
| 220572_at | DKFZp547G183 | hypothetical LOC55525 | NM_018705 | 1.8600E-05 |
| 206462_s_at | NTRK3 | neurotrophic tyrosine kinase receptor type 3 | NM_002530 | 1.8602E-05 |
| 207057_at | SLC16A7 | solute carrier family 16 member 7 (monocarboxylic acid transporter 2) | NM_004731 | 1.9146E-05 |
| 207911_s_at | TGM5 | transglutaminase 5 | NM_004245 | 1.9378E-05 |
| 207730_x_at | | null | NM_017932 | 1.9989E-05 |
| 217620_s_at | PIK3CB | phosphoinositide-3-kinase catalytic beta polypeptide | AA805318 | 2.0764E-05 |
| 208345_s_at | POU3F1 | POU class 3 homeobox 1 | NM_002829 | 2.1059E-05 |
| 220796_x_at | SLC35E1 | solute carrier family 35 member E1 | NM_024881 | 2.1364E-05 |
| 210613_s_at | SYNGR1 | synaptogyrin 1 | BC000731 | 2.1806E-05 |
| 214305_s_at | SF3B1 | splicing factor 3b subunit 1 155kDa | AW003030 | 2.2116E-05 |
| 201867_s_at | TBL1X | transducin (beta)-like 1X-linked | AW968555 | 2.2119E-05 |
| 213748_at | TRIM66 | tripartite motif-containing 66 | AW271713 | 2.2307E-05 |
| 220688_s_at | MRTO4 | mRNA turnover 4 homolog (*S. cerevisiae*) | NM_016183 | 2.2339E-05 |
| 204180_s_at | ZBTB43 | zinc finger and BTB domain containing 43 | AI745225 | 2.2691E-05 |
| 202669_s_at | EFNB2 | ephrin-B2 | U16797 | 2.2926E-05 |
| 208003_s_at | NFAT5 | nuclear factor of activated T-cells 5 tonicity-responsive | NM_006599 | 2.3205E-05 |
| 212106_at | FAF2 | Fas associated factor family member 2 | BF116183 | 2.3380E-05 |
| 211921_x_at | PTMA | prothymosin alpha | AF348514 | 2.3625E-05 |
| 220901_at | GPR157 | G protein-coupled receptor 157 | NM_024980 | 2.4153E-05 |
| 218930_s_at | TMEM106B | transmembrane protein 106B | NM_018374 | 2.4608E-05 |
| 211992_at | WNK1 | WNK lysine deficient protein kinase 1 | AI445745 | 2.4613E-05 |
| 215206_at | | null | AK025143 | 2.4978E-05 |
| 203181_x_at | SRPK2 | SFRS protein kinase 2 | AW149364 | 2.5494E-05 |
| 209030_s_at | CADM1 | cell adhesion molecule 1 | NM_014333 | 2.5571E-05 |
| 211316_x_at | CFLAR | CASP8 and FADD-like apoptosis regulator | AF009616 | 2.6699E-05 |
| 211387_x_at | RNGTT | RNA guanylyltransferase and 5′-phosphatase | AB012143 | 2.7582E-05 |
| 219633_at | TTPAL | tocopherol (alpha) transfer protein-like | NM_024331 | 2.8430E-05 |
| 200637_s_at | PTPRF | protein tyrosine phosphatase receptor type F | AI762627 | 2.8541E-05 |
| 213298_at | NFIC | nuclear factor I/C (CCAAT-binding transcription factor) | X12492 | 2.8753E-05 |

TABLE D-continued

| Probe set ID | Gene Symbol | Gene Name | Representative Public ID | p value |
| --- | --- | --- | --- | --- |
| 212079_s_at | MLL | myeloid/lymphoid or mixed-lineage leukemia (trithorax homolog Drosophila) | AA715041 | 2.9516E-05 |
| 219235_s_at | PHACTR4 | phosphatase and actin regulator 4 | NM_023923 | 3.0091E-05 |
| 212229_s_at | FBXO21 | F-box protein 21 | AK001699 | 3.0649E-05 |
| 220720_x_at | FAM128B | family with sequence similarity 128 member B | NM_025029 | 3.1771E-05 |
| 219717_at | C4orf30 | chromosome 4 open reading frame 30 | NM_017741 | 3.4671E-05 |
| 210426_x_at | RORA | RAR-related orphan receptor A | U04897 | 3.5549E-05 |
| 207382_at | TP63 | tumor protein p63 | NM_003722 | 3.6289E-05 |
| 202082_s_at | SEC14L1 | SEC14-like 1 (*S. cerevisiae*) | AV748469 | 3.6797E-05 |
| 215628_x_at | | null | AL049285 | 3.6881E-05 |
| 210057_at | SMG1 | SMG1 homolog phosphatidylinositol 3-kinase-related kinase (*C. elegans*) | U32581 | 3.7071E-05 |
| 212808_at | NFATC2IP | nuclear factor of activated T-cells cytoplasmic calcineurin-dependent 2 interacting protein | AI884627 | 3.9473E-05 |
| 215066_at | PTPRF | protein tyrosine phosphatase receptor type F | AU158443 | 3.9879E-05 |
| 205370_x_at | DBT | dihydrolipoamide branched chain transacylase E2 | NM_001918 | 4.0073E-05 |
| 218489_s_at | ALAD | aminolevulinate delta- dehydratase | NM_000031 | 4.1739E-05 |
| 209024_s_at | SYNCRIP | synaptotagmin binding cytoplasmic RNA interacting protein | AI472757 | 4.1961E-05 |
| 210407_at | PPM1A | protein phosphatase 1A (formerly 2C) magnesium-dependent alpha isoform | AF070670 | 4.2137E-05 |
| 204290_s_at | ALDH6A1 | aldehyde dehydrogenase 6 family member A1 | NM_005589 | 4.2320E-05 |
| 33646_g_at | GM2A | GM2 ganglioside activator | X61094 | 4.2372E-05 |
| 201606_s_at | PWP1 | PWP1 homolog (*S. cerevisiae*) | BE796924 | 4.3138E-05 |
| 208485_x_at | CFLAR | CASP8 and FADD-like apoptosis regulator | NM_003879 | 4.3820E-05 |
| 215428_at | | null | AL109707 | 4.4947E-05 |
| 201918_at | SLC25A36 | solute carrier family 25 member 36 | AI927944 | 4.5232E-05 |
| 221416_at | PLA2G2F | phospholipase A2 group IIF | NM_022819 | 4.5850E-05 |
| 221006_s_at | SNX27 | sorting nexin family member 27 | NM_030918 | 4.6187E-05 |
| 209065_at | UQCRB | ubiquinol-cytochrome c reductase binding protein | BC005230 | 4.6351E-05 |
| 219910_at | FICD | FIC domain containing | NM_007076 | 4.6518E-05 |
| 210130_s_at | TM7SF2 | transmembrane 7 superfamily member 2 | AF096304 | 4.6563E-05 |
| 216189_at | | null | BC002465 | 4.7282E-05 |
| 39313_at | WNK1 | KIAA0344 gene | AB002342 | 4.8130E-05 |
| 208930_s_at | ILF3 | interleukin enhancer binding factor 3 90kDa | BG032366 | 4.8427E-05 |
| 208549_x_at | PTMAP7 | prothymosin alpha pseudogene 7 | NM_016171 | 4.9816E-05 |
| 201631_s_at | IER3 | immediate early response 3 | NM_003897 | 5.0093E-05 |
| 210701_at | CFDP1 | craniofacial development protein 1 | D85939 | 5.0154E-05 |
| 213998_s_at | DDX17 | DEAD (Asp-Glu-Ala-Asp) box polypeptide 17 | AW188131 | 5.0660E-05 |
| 214972_at | MGEA5 | Meningioma expressed antigen 5 (hyaluronidase) mRNA (cDNA clone MGC:48750 IMAGE:5558183) | AU144791 | 5.0939E-05 |
| 220113_x_at | POLR1B | polymerase (RNA) I polypeptide B 128kDa | NM_019014 | 5.1800E-05 |
| 209203_s_at | BICD2 | bicaudal D homolog 2 (*Drosophila*) | BC002327 | 5.2918E-05 |
| 209508_x_at | CFLAR | CASP8 and FADD-like apoptosis regulator | AF005774 | 5.4720E-05 |
| 208120_x_at | FKSG49 | FKSG49 | NM_031221 | 5.4869E-05 |
| 201683_x_at | TOX4 | TOX high mobility group box family member 4 | BE783632 | 5.5472E-05 |
| 201548_s_at | JARID1B | jumonji AT rich interactive domain 1B | W02593 | 5.7057E-05 |
| 216175_at | | null | AK025276 | 5.8353E-05 |
| 209225_x_at | TNPO1 | transportin 1 | AI653355 | 5.8424E-05 |
| 212629_s_at | PKN2 | protein kinase N2 | AI633689 | 5.8864E-05 |
| 214843_s_at | USP33 | ubiquitin specific peptidase 33 | AK022864 | 5.8995E-05 |
| 212840_at | UBXN7 | UBX domain protein 7 | BG339560 | 5.9251E-05 |
| 214374_s_at | PPFIBP1 | PTPRF interacting protein binding protein 1 (liprin beta 1) | AI962377 | 5.9916E-05 |
| 212807_s_at | SORT1 | sortilin 1 | BF447105 | 6.1077E-05 |
| 201879_at | ARIH1 | ariadne homolog ubiquitin-conjugating enzyme E2 binding protein 1 (*Drosophila*) | AI694332 | 6.1735E-05 |
| 202844_s_at | RALBP1 | ralA binding protein 1 | AW025261 | 6.2362E-05 |
| 203176_s_at | TFAM | transcription factor A mitochondrial | BE552470 | 6.3943E-05 |
| 202867_s_at | DNAJB12 | DnaJ (Hsp40) homolog subfamily B member 12 | NM_017626 | 6.5775E-05 |
| 217593_at | ZSCAN18 | zinc finger and SCAN domain containing 18 | AI375002 | 6.6413E-05 |
| 201846_s_at | RYBP | RING1 and YY1 binding protein | NM_012234 | 6.6541E-05 |
| 210734_x_at | MAX | MYC associated factor X | M64240 | 6.7154E-05 |
| 221985_at | KLHL24 | kelch-like 24 (*Drosophila*) | AW006750 | 6.8295E-05 |
| 213506_at | F2RL1 | coagulation factor II (thrombin) receptor-like 1 | BE965369 | 6.9457E-05 |
| 219915_s_at | SLC16A10 | solute carrier family 16 member 10 (aromatic amino acid transporter) | NM_018593 | 7.0225E-05 |
| 216243_s_at | IL1RN | interleukin 1 receptor antagonist | BE563442 | 7.0801E-05 |
| 210679_x_at | | null | BC002629 | 7.1307E-05 |
| 204863_s_at | IL6ST | interleukin 6 signal transducer (gp130 oncostatin M receptor) | BE856546 | 7.2636E-05 |
| 209750_at | NR1D2 | nuclear receptor subfamily 1 group D member 2 | N32859 | 7.4546E-05 |
| 204680_s_at | RAPGEF5 | Rap guanine nucleotide exchange factor (GEF) 5 | AI263837 | 7.6949E-05 |
| 205809_s_at | WASL | Wiskott-Aldrich syndrome-like | BE504979 | 7.7732E-05 |
| 217370_x_at | FUS | fusion (involved in t(12;16) in malignant liposarcoma) | S75762 | 7.8524E-05 |
| 201085_s_at | SON | SON DNA binding protein | AA664291 | 8.0308E-05 |
| 217550_at | ATF6 | ATF family member ATF6 (ATF6) | AA576497 | 8.1358E-05 |
| 213299_at | ZBTB7A | zinc finger and BTB domain containing 7A | AW027070 | 8.2767E-05 |
| 217152_at | | null | AK024136 | 8.4186E-05 |
| 204358_s_at | FLRT2 | fibronectin leucine rich transmembrane protein 2 | AF169676 | 8.5719E-05 |
| 201996_s_at | SPEN | spen homolog transcriptional regulator (*Drosophila*) | AL524033 | 8.8224E-05 |
| 213446_s_at | IQGAP1 | IQ motif containing GTPase activating protein 1 | AI679073 | 8.8686E-05 |
| 214001_x_at | RPS10 | Ribosomal protein S10 | AW302047 | 8.9790E-05 |
| 211317_s_at | CFLAR | CASP8 and FADD-like apoptosis regulator | AF041461 | 9.0579E-05 |
| 204131_s_at | FOXO3 | forkhead box O3 | N25732 | 9.2446E-05 |

TABLE D-continued

| Probe set ID | Gene Symbol | Gene Name | Representative Public ID | p value |
|---|---|---|---|---|
| 202971_s_at | DYRK2 | dual-specificity tyrosine-(Y)-phosphorylation regulated kinase 2 | NM_006482 | 9.2687E-05 |
| 209807_s_at | NFIX | nuclear factor I/X (CCAAT-binding transcription factor) | U18759 | 9.3413E-05 |
| 222180_at | | null | AU147889 | 9.4177E-05 |
| 216711_s_at | TAF1 | TAF1 RNA polymerase II TATA box binding protein (TBP)-associated factor 250kDa | M73444 | 9.4219E-05 |
| 214912_at | | null | AK022067 | 9.4601E-05 |
| 203899_s_at | CRCP | CGRP receptor component | NM_014478 | 9.4951E-05 |
| 208336_s_at | GPSN2 | glycoprotein synaptic 2 | NM_004868 | 9.7951E-05 |
| 200616_s_at | MLEC | malectin | BC000371 | 1.0015E-04 |
| 219963_at | DUSP13 | dual specificity phosphatase 13 | NM_016364 | 1.0195E-04 |
| 222263_at | SLC35E1 | solute carrier family 35 member E1 | BE904333 | 1.0454E-04 |
| 202045_s_at | GRLF1 | glucocorticoid receptor DNA binding factor 1 | AI670100 | 1.0659E-04 |
| 213650_at | GOLGA8A | golgi autoantigen golgin subfamily a 8A | AW006438 | 1.0835E-04 |
| 220675_s_at | PNPLA3 | patatin-like phospholipase domain containing 3 | NM_025225 | 1.0928E-04 |
| 211000_s_at | IL6ST | interleukin 6 signal transducer (gp130 oncostatin M receptor) | AB015706 | 1.1061E-04 |
| 208114_s_at | ISG20L2 | interferon stimulated exonuclease gene 20kDa-like 2 | NM_030980 | 1.1075E-04 |
| 203515_s_at | PMVK | phosphomevalonate kinase | NM_006556 | 1.1168E-04 |
| 209890_at | TSPAN5 | tetraspanin 5 | AF065389 | 1.1232E-04 |
| 203027_s_at | MVD | mevalonate (diphospho) decarboxylase | AI189359 | 1.1424E-04 |
| 210251_s_at | RUFY3 | RUN and FYVE domain containing 3 | AF112221 | 1.1432E-04 |
| 207993_s_at | CHP | calcium binding protein P22 | NM_007236 | 1.1696E-04 |
| 212007_at | UBXN4 | UBX domain protein 4 | AI927512 | 1.1705E-04 |
| 218150_at | ARL5A | ADP-ribosylation factor-like 5A | NM_012097 | 1.1723E-04 |
| 202035_s_at | SFRP1 | secreted frizzled-related protein 1 | AI332407 | 1.1931E-04 |
| 221765_at | UGCG | UDP-glucose ceramide glucosyltransferase | AI378044 | 1.1935E-04 |
| 201183_s_at | CHD4 | chromodomain helicase DNA binding protein 4 | AI613273 | 1.2057E-04 |
| 213579_s_at | EP300 | E1A binding protein p300 | AI459462 | 1.2148E-04 |
| 210598_at | | null | AF130051 | 1.2242E-04 |
| 208042_at | AGGF1 | angiogenic factor with G patch and FHA domains 1 | NM_013303 | 1.2329E-04 |
| 208699_x_at | TKT | transketolase | BF696840 | 1.2417E-04 |
| 204463_at | EDNRA | endothelin receptor type A | AU118882 | 1.2584E-04 |
| 216316_x_at | GK | glycerol kinase | X78713 | 1.2804E-04 |
| 203542_s_at | KLF9 | Kruppel-like factor 9 | AI690205 | 1.2986E-04 |
| 214833_at | TMEM63A | transmembrane protein 63A | AB007958 | 1.3339E-04 |
| 201072_s_at | SMARCC1 | SWI/SNF related matrix associated actin dependent regulator of chromatin subfamily c member 1 | AW152160 | 1.3391E-04 |
| 217813_s_at | SPIN1 | spindlin 1 | NM_006717 | 1.3414E-04 |
| 200635_s_at | PTPRF | protein tyrosine phosphatase receptor type F | AU145351 | 1.3466E-04 |
| 209069_s_at | H3F3A | H3 histone family 3A | BC001124 | 1.3652E-04 |
| 35436_at | GOLGA2 | golgi autoantigen golgin subfamily a 2 | L06147 | 1.3653E-04 |
| 201287_s_at | SDC1 | syndecan 1 | NM_002997 | 1.3732E-04 |
| 214670_at | ZKSCAN1 | zinc finger with KRAB and SCAN domains 1 | AA653300 | 1.4190E-04 |
| 222214_at | | null | AK024988 | 1.4292E-04 |
| 219428_s_at | PXMP4 | peroxisomal membrane protein 4 24kDa | BF057649 | 1.4316E-04 |
| 203524_s_at | MPST | mercaptopyruvate sulfurtransferase | NM_021126 | 1.4351E-04 |
| 213805_at | ABHD5 | abhydrolase domain containing 5 | AI692428 | 1.4397E-04 |
| 209193_at | PIM1 | pim-1 oncogene | M24779 | 1.4475E-04 |
| 218724_s_at | TGIF2 | TGFB-induced factor homeobox 2 | NM_021809 | 1.4720E-04 |
| 219723_x_at | AGPAT3 | 1-acylglycerol-3-phosphate O-acyltransferase 3 | NM_020132 | 1.4809E-04 |
| 220178_at | C19orf28 | chromosome 19 open reading frame 28 | NM_021731 | 1.4817E-04 |
| 222036_s_at | MCM4 | minichromosome maintenance complex component 4 | AI859865 | 1.4881E-04 |
| 203975_s_at | CHAF1A | chromatin assembly factor 1 subunit A (p150) | BF000239 | 1.4883E-04 |
| 214352_s_at | KRAS | v-Ki-ras2 Kirsten rat sarcoma viral oncogene homolog | BF673699 | 1.4977E-04 |
| 205783_at | KLK13 | kallikrein-related peptidase 13 | NM_015596 | 1.5104E-04 |
| 211040_x_at | GTSE1 | G-2 and S-phase expressed 1 | BC006325 | 1.5322E-04 |
| 207700_s_at | NCOA3 | nuclear receptor coactivator 3 | NM_006534 | 1.5903E-04 |
| 215986_at | | null | AU146999 | 1.5936E-04 |
| 222284_at | | null | AI734111 | 1.6225E-04 |
| 215355_at | POU2F3 | CDNA FLJ61459 complete cds highly similar to POU domain class 2 transcription factor 3 | AI686582 | 1.6659E-04 |
| 204712_at | WIF1 | WNT inhibitory factor 1 | NM_007191 | 1.6699E-04 |
| 204074_s_at | KIAA0562 | KIAA0562 | AI936976 | 1.6713E-04 |
| 204710_s_at | WIPI2 | WD repeat domain phosphoinositide interacting 2 | NM_016003 | 1.6842E-04 |
| 203007_x_at | LYPLA1 | lysophospholipase I | AF077198 | 1.6870E-04 |
| 218155_x_at | TSR1 | TSR1 20S rRNA accumulation homolog (S. cerevisiae) | AK026565 | 1.6954E-04 |
| 204941_s_at | ALDH3B2 | aldehyde dehydrogenase 3 family member B2 | AA071510 | 1.7220E-04 |
| 213936_x_at | SFTPB | surfactant protein B | AW276646 | 1.7285E-04 |
| 217713_x_at | | null | AA126763 | 1.7423E-04 |
| 91920_at | BCAN | brevican | AI205180 | 1.7852E-04 |
| 216641_s_at | LAD1 | ladinin 1 | U58994 | 1.7900E-04 |
| 202028_s_at | RPL38 | ribosomal protein L38 | BC000603 | 1.8201E-04 |
| 200842_s_at | EPRS | glutamyl-prolyl-tRNA synthetase | AI475965 | 1.8206E-04 |
| 215032_at | RREB1 | ras responsive element binding protein 1 | AK022442 | 1.8444E-04 |
| 211944_at | BAT2D1 | BAT2 domain containing 1 | BE729523 | 1.8445E-04 |
| 215780_s_at | SET | SET translocation (myeloid leukemia-associated) pseudogene | Z95126 | 1.8450E-04 |
| 209136_s_at | USP10 | ubiquitin specific peptidase 10 | BG390445 | 1.8544E-04 |
| 201035_s_at | HADH | hydroxyacyl-Coenzyme A dehydrogenase | BC000306 | 1.8556E-04 |

TABLE D-continued

| Probe set ID | Gene Symbol | Gene Name | Representative Public ID | p value |
|---|---|---|---|---|
| 205338_s_at | DCT | dopachrome tautomerase (dopachrome delta-isomerase tyrosine-related protein 2) | NM_001922 | 1.8660E-04 |
| 219392_x_at | PRR11 | proline rich 11 | NM_018304 | 1.8715E-04 |
| 214682_at | LOC399491 | LOC399491 protein | AK023376 | 1.8746E-04 |
| 221419_s_at | | null | NM_013307 | 1.8781E-04 |
| 201411_s_at | PLEKHB2 | pleckstrin homology domain containing family B (evectins) member 2 | NM_017958 | 1.9071E-04 |
| 202053_at | ALDH3A2 | aldehyde dehydrogenase 3 family member A2 | L47162 | 1.9195E-04 |
| 215029_at | | null | AL117451 | 1.9204E-04 |
| 217482_at | | null | AK021987 | 1.9253E-04 |
| 218521_s_at | UBE2W | ubiquitin-conjugating enzyme E2W (putative) | NM_018299 | 1.9276E-04 |
| 208200_at | IL1A | interleukin 1 alpha | NM_000575 | 1.9377E-04 |
| 200727_s_at | ACTR2 | ARP2 actin-related protein 2 homolog (yeast) | AA699583 | 1.9730E-04 |
| 215069_at | NMT2 | N-myristoyltransferase 2 | AK025065 | 1.9771E-04 |
| 215067_x_at | PRDX2 | peroxiredoxin 2 | AU147942 | 2.0142E-04 |
| 201294_s_at | WSB1 | WD repeat and SOCS box-containing 1 | N24643 | 2.0215E-04 |
| 201205_at | | null | AF006751 | 2.0372E-04 |
| 214734_at | EXPH5 | exophilin 5 | AB014524 | 2.0781E-04 |
| 210513_s_at | VEGFA | vascular endothelial growth factor A | AF091352 | 2.0886E-04 |
| 209167_at | GPM6B | glycoprotein M6B | AI419030 | 2.1021E-04 |
| 206551_x_at | KLHL24 | kelch-like 24 (Drosophila) | NM_017644 | 2.1048E-04 |
| 221830_at | RAP2A | RAP2A member of RAS oncogene family | AI302106 | 2.1126E-04 |
| 204675_at | SRD5A1 | steroid-5-alpha-reductase alpha polypeptide 1 (3-oxo-5 alpha-steroid delta 4-dehydrogenase alpha 1) | NM_001047 | 2.1270E-04 |
| 212468_at | SPAG9 | sperm associated antigen 9 | AK023512 | 2.1355E-04 |
| 213228_at | PDE8B | phosphodiesterase 8B | AK023913 | 2.1410E-04 |
| 206929_s_at | NFIC | nuclear factor I/C (CCAAT-binding transcription factor) | NM_005597 | 2.1412E-04 |
| 204347_at | AK3L1 | adenylate kinase 3-like 1 | AI653169 | 2.1420E-04 |
| 204387_x_at | MRP63 | mitochondrial ribosomal protein 63 | NM_024026 | 2.1456E-04 |
| 212290_at | SLC7A1 | solute carrier family 7 (cationic amino acid transporter y+ system) member 1 | AA527433 | 2.1475E-04 |
| 210282_at | ZMYM2 | zinc finger MYM-type 2 | AL136621 | 2.1681E-04 |
| 216503_s_at | MLLT10 | myeloid/lymphoid or mixed-lineage leukemia (trithorax homolog Drosophila); translocated to 10 | AF060927 | 2.1739E-04 |
| 216512_s_at | DCT | dopachrome tautomerase (dopachrome delta-isomerase tyrosine-related protein 2) | AL139318 | 2.2002E-04 |
| 220011_at | C1orf135 | chromosome 1 open reading frame 135 | NM_024037 | 2.2283E-04 |
| 217703_x_at | | null | AA401963 | 2.2444E-04 |
| 202122_s_at | M6PRBP1 | mannose-6-phosphate receptor binding protein 1 | NM_005817 | 2.2502E-04 |
| 219789_at | NPR3 | natriuretic peptide receptor C/guanylate cyclase C (atrionatriuretic peptide receptor C) | AI628360 | 2.2627E-04 |
| 208615_s_at | PTP4A2 | protein tyrosine phosphatase type IVA member 2 | BF795101 | 2.2678E-04 |
| 219341_at | CLN8 | ceroid-lipofuscinosis neuronal 8 (epilepsy progressive with mental retardation) | NM_018941 | 2.3705E-04 |
| 33148_at | ZFR | zinc finger RNA binding protein | AI459274 | 2.3899E-04 |
| 214383_x_at | KLHDC3 | kelch domain containing 3 | BF063121 | 2.3941E-04 |
| 1053_at | RFC2 | replication factor C (activator 1) 2 40kDa | M87338 | 2.4024E-04 |
| 215620_at | RREB1 | ras responsive element binding protein 1 | AU147182 | 2.4784E-04 |
| 214715_x_at | ZNF160 | zinc finger protein 160 | AK024789 | 2.5344E-04 |
| 205538_at | CORO2A | coronin actin binding protein 2A | NM_003389 | 2.5574E-04 |
| 202975_s_at | RHOBTB3 | Rho-related BTB domain containing 3 | N21138 | 2.5588E-04 |
| 221495_at | BNIP3L | BCL2/adenovirus E1B 19kDa interacting protein 3-like | AF060922 | 2.5978E-04 |
| 215600_x_at | FBXW12 | CDNA FLJ40275 fis clone TESTI2027185 | AK022174 | 2.6324E-04 |
| 204375_at | CLSTN3 | calsyntenin 3 | NM_014718 | 2.6950E-04 |
| 217862_at | PIAS1 | protein inhibitor of activated STAT 1 | N24868 | 2.6992E-04 |
| 215604_x_at | | null | AK023783 | 2.7098E-04 |
| 213209_at | TAF6L | TAF6-like RNA polymerase II p300/CBP-associated factor (PCAF)-associated factor 65kDa | BF058726 | 2.7694E-04 |

TABLE E

| Probe Set ID | CMP_62_13 CMapRank |
|---|---|
| 33579_i_at | 1 |
| 205182_s_at | 2 |
| 216001_at | 3 |
| 222160_at | 4 |
| 202005_at | 5 |
| 211197_s_at | 6 |
| 209325_s_at | 7 |
| 208725_at | 8 |
| 207675_x_at | 9 |
| 204397_at | 10 |
| 217516_x_at | 11 |
| 207136_at | 12 |
| 204466_s_at | 13 |
| 212823_s_at | 14 |
| 202616_s_at | 15 |
| 219853_at | 16 |
| 217171_at | 17 |
| 221176_x_at | 18 |
| 208349_at | 19 |
| 215292_s_at | 20 |
| 208340_at | 10100 |
| 214046_at | 10101 |
| 219159_s_at | 10102 |
| 207402_at | 10103 |
| 215757_at | 10104 |
| 217026_at | 10105 |
| 210163_at | 10106 |
| 207659_s_at | 10107 |
| 214470_at | 10108 |
| 203703_s_at | 10109 |
| 222114_x_at | 10110 |
| 208515_at | 10111 |

TABLE E-continued

| Probe Set ID | CMP_62_13 CMapRank |
|---|---|
| 207369_at | 10112 |
| 206865_at | 10113 |
| 214067_at | 10114 |
| 214059_at | 10115 |
| 206498_at | 10116 |
| 206957_at | 10117 |
| 206434_at | 10118 |
| 221391_at | 10119 |
| 211701_s_at | 10120 |
| 213075_at | 22193 |
| 219784_at | 22194 |
| 214283_at | 22195 |
| 215233_at | 22196 |
| 219752_at | 22197 |
| 208987_s_at | 22198 |
| 203836_s_at | 22199 |
| 216025_x_at | 22200 |
| 220178_at | 22201 |
| 210126_at | 22202 |
| 216320_x_at | 22203 |
| 222015_at | 22204 |
| 214372_x_at | 22205 |
| 205875_s_at | 22206 |
| 218720_x_at | 22207 |
| 211573_x_at | 22208 |
| 219640_at | 22209 |
| 204701_s_at | 22210 |
| 204484_at | 22211 |
| 209547_s_at | 22212 |
| 209876_at | 22213 |
| 219664_s_at | 22214 |

TABLE F

| Probe Set ID | CMP_61_13 CMapRank |
|---|---|
| 216074_x_at | 1 |
| 217391_x_at | 2 |
| 219807_x_at | 3 |
| 220538_at | 4 |
| 205654_at | 5 |
| 213710_s_at | 6 |
| 202099_s_at | 7 |
| 204307_at | 8 |
| 213141_at | 9 |
| 210974_s_at | 10 |
| 217723_x_at | 11 |
| 202991_at | 12 |
| 218272_at | 13 |
| 219057_at | 14 |
| 212487_at | 15 |
| 206485_at | 16 |
| 206289_at | 17 |
| 202669_s_at | 18 |
| 205182_s_at | 19 |
| 216472_at | 20 |
| 220630_s_at | 10100 |
| 211333_s_at | 10101 |
| 203547_at | 10102 |
| 210889_s_at | 10103 |
| 221159_at | 10104 |
| 208253_at | 10105 |
| 216188_at | 10106 |
| 216879_at | 10107 |
| 205949_at | 10108 |
| 216763_at | 10109 |
| 215186_at | 10110 |
| 221141_x_at | 10111 |
| 209145_s_at | 10112 |
| 206731_at | 10113 |
| 217514_at | 10114 |
| 213162_at | 10115 |
| 217429_at | 10116 |
| 206645_s_at | 10117 |
| 37201_at | 10118 |

TABLE F-continued

| Probe Set ID | CMP_61_13 CMapRank |
|---|---|
| 217706_at | 10119 |
| 207167_at | 10120 |
| 210357_s_at | 22194 |
| 222362_at | 22195 |
| 213303_x_at | 22196 |
| 211112_at | 22197 |
| 214879_x_at | 22198 |
| 210739_x_at | 22199 |
| 216042_at | 22200 |
| 209436_at | 22201 |
| 206063_x_at | 22202 |
| 213521_at | 22203 |
| 209926_at | 22204 |
| 218965_s_at | 22205 |
| 206911_at | 22206 |
| 222167_at | 22207 |
| 221061_at | 22208 |
| 214893_x_at | 22209 |
| 202685_s_at | 22210 |
| 218599_at | 22211 |
| 215595_x_at | 22212 |
| 221992_at | 22213 |
| 215015_at | 22214 |

TABLE G

| Probe Set ID | CMP_62_24 CMapRank |
|---|---|
| 212925_at | 1 |
| 214542_x_at | 2 |
| 206739_at | 3 |
| 214223_at | 4 |
| 222013_x_at | 5 |
| 221010_s_at | 6 |
| 205648_at | 7 |
| 207346_at | 8 |
| 208040_s_at | 9 |
| 214054_at | 10 |
| 204776_at | 11 |
| 205950_s_at | 12 |
| 221270_s_at | 13 |
| 216293_at | 14 |
| 206994_at | 15 |
| 222210_at | 16 |
| 216940_x_at | 17 |
| 215736_at | 18 |
| 205275_at | 19 |
| 222375_at | 20 |
| 217583_at | 11000 |
| 214025_at | 11001 |
| 210392_x_at | 11002 |
| 216673_at | 11003 |
| 220911_s_at | 11004 |
| 207873_x_at | 11005 |
| 219572_at | 11006 |
| 214329_x_at | 11007 |
| 213683_at | 11008 |
| 208385_at | 11009 |
| 211336_x_at | 11010 |
| 205380_at | 11011 |
| 204855_at | 11012 |
| 208593_x_at | 11013 |
| 214952_at | 11014 |
| 220893_at | 11015 |
| 215228_at | 11016 |
| 205814_at | 11017 |
| 210121_at | 11018 |
| 208208_at | 11019 |
| 215465_at | 11020 |
| 209794_at | 22194 |
| 221810_at | 22195 |
| 217107_at | 22196 |
| 212611_at | 22197 |
| 217135_x_at | 22198 |
| 221077_at | 22199 |

TABLE G-continued

| Probe Set ID | CMP_62_24 CMapRank |
|---|---|
| 211241_at | 22200 |
| 212153_at | 22201 |
| 210126_at | 22202 |
| 212475_at | 22203 |
| 209547_s_at | 22204 |
| 208987_s_at | 22205 |
| 216320_x_at | 22206 |
| 212713_at | 22207 |
| 204484_at | 22208 |
| 214880_x_at | 22209 |
| 206764_x_at | 22210 |
| 219636_s_at | 22211 |
| 210933_s_at | 22212 |
| 219664_s_at | 22213 |
| 219018_s_at | 22214 |

TABLE H

| Probe Set ID | CMP_61_23 CMapRank |
|---|---|
| 209547_s_at | 1 |
| 210974_s_at | 2 |
| 210348_at | 3 |
| 219807_x_at | 4 |
| 205743_at | 5 |
| 216243_s_at | 6 |
| 215195_at | 7 |
| 214320_x_at | 8 |
| 220940_at | 9 |
| 220694_at | 10 |
| 210325_at | 11 |
| 205950_s_at | 12 |
| 201808_s_at | 13 |
| 220319_s_at | 14 |
| 220243_at | 15 |
| 220028_at | 16 |
| 336_at | 17 |
| 215757_at | 18 |
| 207670_at | 19 |
| 211304_x_at | 20 |
| 221866_at | 11000 |

TABLE H-continued

| Probe Set ID | CMP_61_23 CMapRank |
|---|---|
| 208534_s_at | 11001 |
| 211643_x_at | 11002 |
| 219890_at | 11003 |
| 216655_s_at | 11004 |
| 216065_at | 11005 |
| 213945_s_at | 11006 |
| 215048_at | 11007 |
| 211232_x_at | 11008 |
| 220687_at | 11009 |
| 215770_at | 11010 |
| 204915_s_at | 11011 |
| 203325_s_at | 11012 |
| 212706_at | 11013 |
| 205948_at | 11014 |
| 205852_at | 11015 |
| 205155_s_at | 11016 |
| 222089_s_at | 11017 |
| 203071_at | 11018 |
| 221784_at | 11019 |
| 210794_s_at | 11020 |
| 205918_at | 22194 |
| 208347_at | 22195 |
| 215845_x_at | 22196 |
| 205662_at | 22197 |
| 208301_at | 22198 |
| 212559_at | 22199 |
| 211088_s_at | 22200 |
| 209031_at | 22201 |
| 216532_x_at | 22202 |
| 213755_s_at | 22203 |
| 211112_at | 22204 |
| 207953_at | 22205 |
| 202497_x_at | 22206 |
| 209035_at | 22207 |
| 215849_x_at | 22208 |
| 210201_x_at | 22209 |
| 219847_at | 22210 |
| 202328_s_at | 22211 |
| 219664_s_at | 22212 |
| 204757_s_at | 22213 |
| 216822_x_at | 22214 |

TABLE I

| Probe set ID | Gene Symbol | Gene Name | Representative Public ID | Log t-ttestRank |
|---|---|---|---|---|
| 205236_x_at | SOD3 | superoxide dismutase 3 extracellular | NM_003102 | 1 |
| 213113_s_at | SLC43A3 | solute carrier family 43 member 3 | AI630178 | 3 |
| 212796_s_at | TBC1D2B | TBC1 domain family member 2B | BF195608 | 4 |
| 213364_s_at | SNX1 | sorting nexin 1 | AI052536 | 7 |
| 202510_s_at | TNFAIP2 | tumor necrosis factor alpha-induced protein 2 | NM_006291 | 8 |
| 213258_at | TFPI | tissue factor pathway inhibitor (lipoprotein-associated coagulation inhibitor) | BF511231 | 9 |
| 202291_s_at | MGP | matrix Gla protein | NM_000900 | 13 |
| 219304_s_at | PDGFD | platelet derived growth factor D | NM_025208 | 14 |
| 202994_s_at | FBLN1 | fibulin 1 | Z95331 | 15 |
| 212589_at | RRAS2 | related RAS viral (r-ras) oncogene homolog 2 | AI753792 | 16 |
| 202912_at | ADM | adrenomedullin | NM_001124 | 17 |
| 203088_at | FBLN5 | fibulin 5 | NM_006329 | 20 |
| 216620_s_at | ARHGEF10 | Rho guanine nucleotide exchange factor (GEF) 10 | AF009205 | 21 |
| 212067_s_at | C1R | complement component 1 r subcomponent | AL573058 | 22 |
| 202363_at | SPOCK1 | sparc/osteonectin cwcv and kazal-like domains proteoglycan (testican) 1 | AF231124 | 23 |
| 206157_at | PTX3 | pentraxin-related gene rapidly induced by IL-1 beta | NM_002852 | 24 |
| 208747_s_at | C1S | complement component 1 s subcomponent | M18767 | 29 |
| 209763_at | CHRDL1 | chordin-like 1 | AL049176 | 30 |
| 200785_s_at | LOC100134190 | similar to low density lipoprotein-related protein 1 (alpha-2-macroglobulin receptor) | NM_002332 | 31 |
| 206373_at | ZIC1 | Zic family member 1 (odd-paired homolog Drosophila) | NM_003412 | 33 |
| 213164_at | SLC5A3 | solute carrier family 5 (sodium/myo-inositol cotransporter) member 3 | AI867198 | 34 |
| 202897_at | SIRPA | signal-regulatory protein alpha | AB023430 | 36 |
| 201787_at | LOC100133843 | fibulin 1 | NM_001996 | 37 |
| 213348_at | CDKN1C | cyclin-dependent kinase inhibitor 1C (p57 Kip2) | N33167 | 38 |
| 201842_s_at | EFEMP1 | EGF-containing fibulin-like extracellular matrix protein 1 | AI826799 | 39 |
| 217800_s_at | NDFIP1 | Nedd4 family interacting protein 1 | NM_030571 | 40 |

TABLE I-continued

| Probe set ID | Gene Symbol | Gene Name | Representative Public ID | Log t-ttestRank |
|---|---|---|---|---|
| 212761_at | TCF7L2 | transcription factor 7-like 2 (T-cell specific HMG-box) | AI949687 | 41 |
| 212944_at | SLC5A3 | solute carrier family 5 (sodium/myo-inositol cotransporter) member 3 | AK024896 | 43 |
| 217904_s_at | BACE1 | beta-site APP-cleaving enzyme 1 | NM_012104 | 44 |
| 209335_at | DCN | decorin | AI281593 | 45 |
| 213568_at | OSR2 | odd-skipped related 2 (*Drosophila*) | AI811298 | 49 |
| 205422_s_at | ITGBL1 | integrin beta-like 1 (with EGF-like repeat domains) | NM_004791 | 50 |
| 200771_at | LAMC1 | laminin gamma 1 (formerly LAMB2) | NM_002293 | 51 |
| 207606_s_at | ARHGAP12 | Rho GTPase activating protein 12 | NM_018287 | 52 |
| 213150_at | HOXA10 | homeobox A10 | BF792917 | 53 |
| 214494_s_at | SPG7 | spastic paraplegia 7 (pure and complicated autosomal recessive) | NM_005200 | 54 |
| 205802_at | TRPC1 | transient receptor potential cation channel subfamily C member 1 | NM_003304 | 55 |
| 212558_at | SPRY1 | sprouty homolog 1 antagonist of FGF signaling (*Drosophila*) | BF508662 | 57 |
| 218901_at | PLSCR4 | phospholipid scramblase 4 | NM_020353 | 58 |
| 200986_at | SERPING1 | serpin peptidase inhibitor clade G (C1 inhibitor) member 1 | NM_000062 | 59 |
| 204963_at | SSPN | sarcospan (Kras oncogene-associated gene) | AL136756 | 60 |
| 203939_at | NT5E | 5'-nucleotidase ecto (CD73) | NM_002526 | 63 |
| 201843_s_at | EFEMP1 | EGF-containing fibulin-like extracellular matrix protein 1 | NM_004105 | 64 |
| 202995_s_at | FBLN1 | fibulin 1 | NM_006486 | 65 |
| 204749_at | NAP1L3 | nucleosome assembly protein 1-like 3 | NM_004538 | 66 |
| 212419_at | ZCCHC24 | zinc finger CCHC domain containing 24 | AA131324 | 67 |
| 203217_s_at | ST3GAL5 | ST3 beta-galactoside alpha-23-sialyltransferase 5 | NM_003896 | 68 |
| 218418_s_at | KANK2 | KN motif and ankyrin repeat domains 2 | NM_015493 | 69 |
| 220327_at | VGLL3 | vestigial like 3 (*Drosophila*) | NM_016206 | 72 |
| 205612_at | MMRN1 | multimerin 1 | NM_007351 | 73 |
| 218276_s_at | SAV1 | salvador homolog 1 (*Drosophila*) | NM_021818 | 76 |
| 212224_at | ALDH1A1 | aldehyde dehydrogenase 1 family member A1 | NM_000689 | 78 |
| 221950_at | EMX2 | empty spiracles homeobox 2 | AI478455 | 79 |
| 205407_at | RECK | reversion-inducing-cysteine-rich protein with kazal motifs | NM_021111 | 80 |
| 221016_s_at | TCF7L1 | transcription factor 7-like 1 (T-cell specific HMG-box) | NM_031283 | 83 |
| 201535_at | UBL3 | ubiquitin-like 3 | NM_007106 | 87 |
| 213429_at | BICC1 | bicaudal C homolog 1 (*Drosophila*) | AW025579 | 88 |
| 217853_at | TNS3 | tensin 3 | NM_022748 | 90 |
| 201811_x_at | SH3BP5 | SH3-domain binding protein 5 (BTK-associated) | NM_004844 | 91 |
| 205011_at | VWA5A | von Willebrand factor A domain containing 5A | NM_014622 | 92 |
| 202220_at | KIAA0907 | KIAA0907 | NM_014949 | 95 |
| 221019_s_at | COLEC12 | collectin sub-family member 12 | NM_030781 | 97 |
| 218162_at | OLFML3 | olfactomedin-like 3 | NM_020190 | 98 |
| 201744_s_at | LUM | lumican | NM_002345 | 99 |
| 202664_at | WIPF1 | WAS/WASL interacting protein family member 1 | AW058622 | 101 |
| 210135_s_at | SHOX2 | short stature homeobox 2 | AF022654 | 102 |
| 203083_at | THBS2 | thrombospondin 2 | NM_003247 | 104 |
| 201792_at | AEBP1 | AE binding protein 1 | NM_001129 | 105 |
| 209265_at | METTL3 | methyltransferase like 3 | BC001650 | 106 |
| 204457_s_at | GAS1 | growth arrest-specific 1 | NM_002048 | 109 |
| 213249_at | FBXL7 | F-box and leucine-rich repeat protein 7 | AU145127 | 111 |
| 201818_at | LPCAT1 | lysophosphatidylcholine acyltransferase 1 | NM_024830 | 112 |
| 203583_at | UNC50 | unc-50 homolog (*C. elegans*) | NM_014044 | 113 |
| 212486_s_at | FYN | FYN oncogene related to SRC FGR YES | N20923 | 114 |
| 205609_at | ANGPT1 | angiopoietin 1 | NM_001146 | 117 |
| 202729_s_at | LTBP1 | latent transforming growth factor beta binding protein 1 | NM_000627 | 119 |
| 36030_at | IFFO1 | intermediate filament family orphan 1 | AL080214 | 123 |
| 204140_at | TPST1 | tyrosylprotein sulfotransferase 1 | NM_003596 | 124 |
| 217122_s_at | LOC728661 | similar to solute carrier family 35 member E2 | AL031282 | 125 |
| 200945_s_at | SEC31A | SEC31 homolog A (*S. cerevisiae*) | NM_014933 | 126 |
| 212621_at | TMEM194A | transmembrane protein 194A | AB006624 | 127 |
| 203131_at | PDGFRA | platelet-derived growth factor receptor alpha polypeptide | NM_006206 | 129 |
| 218715_at | UTP6 | UTP6 small subunit (SSU) processome component homolog (yeast) | NM_018428 | 132 |
| 212877_at | KLC1 | kinesin light chain 1 | AA284075 | 134 |
| 218204_s_at | FYCO1 | FYVE and coiled-coil domain containing 1 | NM_024513 | 138 |
| 203812_at | | null | AB011538 | 140 |
| 213422_s_at | MXRA8 | matrix-remodelling associated 8 | AW888223 | 141 |
| 212736_at | C16orf45 | chromosome 16 open reading frame 45 | BE299456 | 142 |
| 212230_at | PPAP2B | phosphatidic acid phosphatase type 2B | AV725664 | 146 |
| 209550_at | NDN | necdin homolog (mouse) | U35139 | 147 |
| 221556_at | CDC14B | CDC14 cell division cycle 14 homolog B (*S. cerevisiae*) | BF792631 | 148 |
| 213802_at | | null | AI810767 | 149 |
| 218718_at | PDGFC | platelet derived growth factor C | NM_016205 | 150 |
| 218146_at | GLT8D1 | glycosyltransferase 8 domain containing 1 | NM_018446 | 153 |
| 205083_at | AOX1 | aldehyde oxidase 1 | NM_001159 | 154 |
| 213161_at | C9orf97 | chromosome 9 open reading frame 97 | AI583393 | 155 |
| 212597_s_at | HMGXB4 | HMG box domain containing 4 | AL079310 | 159 |
| 210105_s_at | FYN | FYN oncogene related to SRC FGR YES | M14333 | 160 |
| 203706_s_at | FZD7 | frizzled homolog 7 (*Drosophila*) | NM_003507 | 163 |
| 202202_s_at | LAMA4 | laminin alpha 4 | NM_002290 | 165 |
| 216033_s_at | FYN | FYN oncogene related to SRC FGR YES | S74774 | 167 |
| 221897_at | TRIM52 | tripartite motif-containing 52 | AA205660 | 169 |
| 218656_s_at | LHFP | lipoma HMGIC fusion partner | NM_005780 | 173 |

TABLE I-continued

| Probe set ID | Gene Symbol | Gene Name | Representative Public ID | Log t-ttestRank |
|---|---|---|---|---|
| 204112_s_at | HNMT | histamine N-methyltransferase | NM_006895 | 175 |
| 204042_at | WASF3 | WAS protein family member 3 | AB020707 | 177 |
| 209568_s_at | RGL1 | ral guanine nucleotide dissociation stimulator-like 1 | AF186779 | 179 |
| 209884_s_at | SLC4A7 | solute carrier family 4 sodium bicarbonate cotransporter member 7 | AF047033 | 180 |
| 201395_at | RBM5 | RNA binding motif protein 5 | NM_005778 | 185 |
| 219552_at | SVEP1 | sushi von Willebrand factor type A EGF and pentraxin domain containing 1 | NM_024500 | 188 |
| 214323_s_at | UPF3A | UPF3 regulator of nonsense transcripts homolog A (yeast) | N36842 | 189 |
| 219093_at | PID1 | phosphotyrosine interaction domain containing 1 | NM_017933 | 191 |
| 204345_at | COL16A1 | collagen type XVI alpha 1 | NM_001856 | 198 |
| 203476_at | TPBG | trophoblast glycoprotein | NM_006670 | 202 |
| 203117_s_at | PAN2 | PAN2 poly(A) specific ribonuclease subunit homolog (*S. cerevisiae*) | NM_014871 | 208 |
| 204453_at | ZNF84 | zinc finger protein 84 | NM_003428 | 209 |
| 203600_s_at | C4orf8 | chromosome 4 open reading frame 8 | NM_003704 | 210 |
| 221760_at | MAN1A1 | CDNA: FLJ21946 fis clone HEP04860 highly similar to HSHUMM9 *Homo sapiens* HUMM9 mRNA | BG287153 | 211 |
| 218793_s_at | SCML1 | sex comb on midleg-like 1 (*Drosophila*) | NM_006746 | 213 |
| 205542_at | STEAP1 | six transmembrane epithelial antigen of the prostate 1 | NM_012449 | 215 |
| 215388_s_at | CFH | complement factor H | X56210 | 217 |
| 201278_at | DAB2 | disabled homolog 2 mitogen-responsive phosphoprotein (*Drosophila*) | N21202 | 218 |
| 206958_s_at | UPF3A | UPF3 regulator of nonsense transcripts homolog A (yeast) | AF318575 | 219 |
| 202273_at | PDGFRB | platelet-derived growth factor receptor beta polypeptide | NM_002609 | 224 |
| 218686_s_at | RHBDF1 | rhomboid 5 homolog 1 (*Drosophila*) | NM_022450 | 227 |
| 39650_s_at | PCNXL2 | pecanex-like 2 (*Drosophila*) | AB007895 | 228 |
| 219639_x_at | PARP6 | poly (ADP-ribose) polymerase family member 6 | NM_020213 | 231 |
| 222235_s_at | CSGALNACT2 | chondroitin sulfate N-acetylgalactosaminyltransferase 2 | AL139812 | 232 |
| 209580_s_at | MBD4 | methyl-CpG binding domain protein 4 | AF114784 | 234 |
| 212651_at | RHOBTB1 | Rho-related BTB domain containing 1 | AB018283 | 236 |
| 207177_at | PTGFR | prostaglandin F receptor (FP) | NM_000959 | 239 |
| 205452_at | PIGB | phosphatidylinositol glycan anchor biosynthesis class B | NM_004855 | 241 |
| 212195_at | IL6ST | interleukin 6 signal transducer (gp130 oncostatin M receptor) | AL049265 | 242 |
| 220351_at | CCRL1 | chemokine (C-C motif) receptor-like 1 | NM_016557 | 243 |
| 212503_s_at | DIP2C | DIP2 disco-interacting protein 2 homolog C (*Drosophila*) | N22859 | 246 |
| 218093_s_at | ANKRD10 | ankyrin repeat domain 10 | NM_017664 | 248 |
| 207808_s_at | PROS1 | protein S (alpha) | NM_000313 | 249 |
| 201034_at | ADD3 | adducin 3 (gamma) | BE545756 | 251 |
| 212327_at | LIMCH1 | LIM and calponin homology domains 1 | AK026815 | 252 |
| 212979_s_at | FAM115A | family with sequence similarity 115 member A | AW293343 | 253 |
| 212855_at | DCUN1D4 | DCN1 defective in cullin neddylation 1 domain containing 4 (*S. cerevisiae*) | D87466 | 257 |
| 219283_at | C1GALT1C1 | C1GALT1-specific chaperone 1 | NM_014158 | 259 |
| 211896_s_at | DCN | decorin | AF138302 | 260 |
| 210139_s_at | PMP22 | peripheral myelin protein 22 | L03203 | 263 |
| 207417_s_at | ZNF177 | zinc finger protein 177 | NM_003451 | 265 |
| 200770_s_at | LAMC1 | laminin gamma 1 (formerly LAMB2) | J03202 | 266 |
| 202920_at | ANK2 | ankyrin 2 neuronal | BF726212 | 267 |
| 221569_at | AHI1 | Abelson helper integration site 1 | AL136797 | 268 |
| 213737_x_at | GOLGA9P | golgi autoantigen golgin subfamily a 9 pseudogene | AI620911 | 269 |
| 202142_at | COPS8 | COP9 constitutive photomorphogenic homolog subunit 8 (*Arabidopsis*) | BC003090 | 270 |
| 202951_at | STK38 | serine/threonine kinase 38 | BE048506 | 272 |
| 201139_s_at | SSB | Sjogren syndrome antigen B (autoantigen La) | NM_003142 | 274 |
| 213293_s_at | TRIM22 | tripartite motif-containing 22 | AA083478 | 276 |
| 218285_s_at | BDH2 | 3-hydroxybutyrate dehydrogenase type 2 | NM_020139 | 278 |
| 213262_at | SACS | spastic ataxia of Charlevoix-Saguenay (sacsin) | AI932370 | 281 |
| 203893_at | TAF9 | TAF9 RNA polymerase II TATA box binding protein (TBP)-associated factor 32kDa | NM_016283 | 282 |
| 201086_x_at | SON | SON DNA binding protein | NM_003103 | 283 |
| 204085_s_at | CLN5 | ceroid-lipofuscinosis neuronal 5 | NM_006493 | 287 |
| 204897_at | PTGER4 | prostaglandin E receptor 4 (subtype EP4) | AA897516 | 288 |
| 212793_at | DAAM2 | dishevelled associated activator of morphogenesis 2 | BF513244 | 289 |
| 204036_at | LPAR1 | lysophosphatidic acid receptor 1 | AW269335 | 291 |
| 212958_x_at | PAM | peptidylglycine alpha-amidating monooxygenase | AI022882 | 292 |
| 211535_s_at | FGFR1 | fibroblast growth factor receptor 1 | M60485 | 295 |
| 212764_at | ZEB1 | zinc finger E-box binding homeobox 1 | AI806174 | 298 |
| 221645_s_at | ZNF83 | zinc finger protein 83 | M27877 | 300 |
| 208922_s_at | NXF1 | nuclear RNA export factor 1 | BC004904 | 301 |
| 203139_at | DAPK1 | death-associated protein kinase 1 | NM_004938 | 302 |
| 220992_s_at | C1orf25 | chromosome 1 open reading frame 25 | NM_030934 | 306 |
| 214703_s_at | MAN2B2 | mannosidase alpha class 2B member 2 | AW954107 | 307 |
| 214749_s_at | ARMCX6 | armadillo repeat containing X-linked 6 | AK000818 | 308 |
| 201150_s_at | TIMP3 | TIMP metallopeptidase inhibitor 3 | NM_000362 | 309 |
| 213455_at | FAM114A1 | family with sequence similarity 114 member A1 | W87466 | 310 |
| 203886_s_at | FBLN2 | fibulin 2 | NM_001998 | 313 |
| 202104_s_at | SPG7 | spastic paraplegia 7 (pure and complicated autosomal recessive) | NM_003119 | 316 |
| 201669_s_at | MARCKS | myristoylated alanine-rich protein kinase C substrate | NM_002356 | 318 |
| 217792_at | SNX5 | sorting nexin 5 | NM_014426 | 319 |
| 204093_at | CCNH | cyclin H | NM_001239 | 320 |
| 208669_s_at | EID1 | EP300 interacting inhibitor of differentiation 1 | AF109873 | 326 |
| 204605_at | CGRRF1 | cell growth regulator with ring finger domain 1 | NM_006568 | 328 |

TABLE I-continued

| Probe set ID | Gene Symbol | Gene Name | Representative Public ID | Log t-ttestRank |
|---|---|---|---|---|
| 211675_s_at | MDFIC | MyoD family inhibitor domain containing | AF054589 | 331 |
| 209101_at | CTGF | connective tissue growth factor | M92934 | 332 |
| 201798_s_at | MYOF | myoferlin | NM_013451 | 334 |
| 206876_at | SIM1 | single-minded homolog 1 (*Drosophila*) | AL121948 | 338 |
| 209946_at | VEGFC | vascular endothelial growth factor C | U58111 | 339 |
| 216840_s_at | LAMA2 | laminin alpha 2 | AK026829 | 340 |
| 208848_at | ADH5 | alcohol dehydrogenase 5 (class III) chi polypeptide | M30471 | 343 |
| 218014_at | NUP85 | nucleoporin 85kDa | NM_024844 | 345 |
| 202478_at | TRIB2 | tribbles homolog 2 (*Drosophila*) | NM_021643 | 346 |
| 201063_at | RCN1 | reticulocalbin 1 EF-hand calcium binding domain | NM_002901 | 347 |
| 209409_at | GRB10 | growth factor receptor-bound protein 10 | D86962 | 348 |
| 212681_at | EPB41L3 | erythrocyte membrane protein band 4.1-like 3 | AI770004 | 349 |
| 202598_at | S100A13 | S100 calcium binding protein A13 | NM_005979 | 351 |
| 209497_s_at | RBM4B | RNA binding motif protein 4B | BC003503 | 352 |
| 219949_at | LRRC2 | leucine rich repeat containing 2 | NM_024512 | 353 |
| 210312_s_at | IFT20 | intraflagellar transport 20 homolog (*Chlamydomonas*) | BC002640 | 354 |
| 213266_at | TUBGCP4 | Tubulin gamma complex associated protein 4 mRNA (cDNA clone MGC:2720 IMAGE:2821891) | BF592982 | 355 |
| 219778_at | ZFPM2 | zinc finger protein multitype 2 | NM_012082 | 357 |
| 210406_s_at | RAB6A | RAB6A member RAS oncogene family | AL136727 | 358 |
| 212148_at | PBX1 | pre-B-cell leukemia homeobox 1 | AL049381 | 359 |
| 203241_at | UVRAG | UV radiation resistance associated gene | NM_003369 | 360 |
| 218076_s_at | ARHGAP17 | Rho GTPase activating protein 17 | NM_018054 | 361 |

TABLE J

| Probe set ID | Gene Symbol | Gene Name | Representative Public ID | Log t-testRank |
|---|---|---|---|---|
| 205187_at | SMAD5 | SMAD family member 5 | AF010601 | 6 |
| 201702_s_at | PPP1R10 | protein phosphatase 1 regulatory (inhibitor) subunit 10 | AI492873 | 11 |
| 211074_at | FOLR1 | folate receptor 1 (adult) | AF000381 | 19 |
| 202102_s_at | BRD4 | bromodomain containing 4 | BF718610 | 25 |
| 214265_at | ITGA8 | integrin alpha 8 | AI193623 | 26 |
| 208711_s_at | CCND1 | cyclin D1 | BC000076 | 27 |
| 222024_s_at | AKAP13 | A kinase (PRKA) anchor protein 13 | AK022014 | 28 |
| 210717_at | | null | AF116659 | 35 |
| 206061_s_at | DICER1 | dicer 1 ribonuclease type III | NM_030621 | 42 |
| 209936_at | RBM5 | RNA binding motif protein 5 | AF107493 | 46 |
| 211081_s_at | MAP4K5 | mitogen-activated protein kinase kinase kinase kinase 5 | Z25426 | 56 |
| 217649_at | ZFAND5 | zinc finger AN1-type domain 5 | AV702306 | 70 |
| 209088_s_at | UBN1 | ubinuclein 1 | T70262 | 81 |
| 210807_s_at | SLC16A7 | solute carrier family 16 member 7 (monocarboxylic acid transporter 2) | AF049608 | 84 |
| 220071_x_at | CEP27 | centrosomal protein 27kDa | NM_018097 | 85 |
| 214153_at | ELOVL5 | ELOVL family member 5 elongation of long chain fatty acids (FEN1/Elo2 SUR4/ Elo3-like yeast) | BE467941 | 89 |
| 211993_at | WNK1 | WNK lysine deficient protein kinase 1 | AI768512 | 100 |
| 213718_at | RBM4 | RNA binding motif protein 4 | BE222257 | 103 |
| 216858_x_at | | null | AL080112 | 116 |
| 212057_at | KIAA0182 | KIAA0182 | AA206161 | 121 |
| 214041_x_at | RPL37A | Ribosomal protein L37a | BE857772 | 130 |
| 209945_s_at | GSK3B | glycogen synthase kinase 3 beta | BC000251 | 131 |
| 216187_x_at | | null | AF222691 | 133 |
| 221943_x_at | RPL38 | Ribosomal protein L38 mRNA (cDNA clone MGC:1637 IMAGE:3346447) | AW303136 | 136 |
| 217538_at | SGSM2 | small G protein signaling modulator 2 | BF347113 | 137 |
| 203803_at | PCYOX1 | prenylcysteine oxidase 1 | N45309 | 139 |
| 202040_s_at | JARID1A | jumonji AT rich interactive domain 1A | NM_005056 | 143 |
| 211503_s_at | RAB14 | RAB14 member RAS oncogene family | AF112206 | 145 |
| 210479_s_at | RORA | RAR-related orphan receptor A | L14611 | 151 |
| 205967_at | HIST1H4A | histone cluster 1 H4a | NM_003542 | 156 |
| 201195_s_at | SLC7A5 | solute carrier family 7 (cationic amino acid transporter y+ system) member 5 | AB018009 | 158 |
| 204881_s_at | UGCG | UDP-glucose ceramide glucosyltransferase | NM_003358 | 161 |
| 201867_s_at | TBL1X | transducin (beta)-like 1X-linked | AW968555 | 162 |
| 201901_s_at | YY1 | YY1 transcription factor | Z14077 | 164 |
| 211337_s_at | TUBGCP4 | tubulin gamma complex associated protein 4 | BC000966 | 166 |
| 214422_at | LOC131185 | similar to RAD23B protein | T93562 | 168 |
| 206036_s_at | REL | v-rel reticuloendotheliosis viral oncogene homolog (avian) | NM_002908 | 170 |
| 203742_s_at | LOC645233 | thymine-DNA glycosylase pseudogene | BF674842 | 171 |
| 213517_at | PCBP2 | poly(rC) binding protein 2 | AW103422 | 174 |
| 203318_s_at | ZNF148 | zinc finger protein 148 | NM_021964 | 176 |
| 214815_at | TRIM33 | tripartite motif-containing 33 | AU136587 | 178 |
| 212492_s_at | JMJD2B | jumonji domain containing 2B | AW237172 | 181 |
| 207657_x_at | TNPO1 | transportin 1 | NM_002270 | 184 |
| 213229_at | DICER1 | dicer 1 ribonuclease type III | BF590131 | 186 |

TABLE J-continued

| Probe set ID | Gene Symbol | Gene Name | Representative Public ID | Log t-testRank |
|---|---|---|---|---|
| 221705_s_at | SIKE | suppressor of IKK epsilon | BC005934 | 187 |
| 210943_s_at | LYST | lysosomal trafficking regulator | U84744 | 190 |
| 212525_s_at | H2AFX | H2A histone family member X | AA760862 | 194 |
| 208624_s_at | EIF4G1 | eukaryotic translation initiation factor 4 gamma 1 | BE966878 | 196 |
| 201917_s_at | SLC25A36 | solute carrier family 25 member 36 | AI694452 | 197 |
| 212229_s_at | FBXO21 | F-box protein 21 | AK001699 | 199 |
| 204181_s_at | ZBTB43 | zinc finger and BTB domain containing 43 | T90308 | 200 |
| 204524_at | PDPK1 | 3-phosphoinositide dependent protein kinase-1 | NM_002613 | 201 |
| 63825_at | ABHD2 | abhydrolase domain containing 2 | AI557319 | 203 |
| 221753_at | SSH1 | slingshot homolog 1 (*Drosophila*) | AI651213 | 204 |
| 214902_x_at | | null | AL080232 | 207 |
| 211387_x_at | RNGTT | RNA guanylyltransferase and 5'-phosphatase | AB012143 | 212 |
| 201299_s_at | MOBKL1B | MOB1 Mps One Binder kinase activator-like 1B (yeast) | NM_018221 | 214 |
| 205322_at | MTF1 | metal-regulatory transcription factor 1 | AW182367 | 216 |
| 215892_at | ZNF440 | Zinc finger protein 440 mRNA (cDNA clone MGC:46665 IMAGE:5556302) | AK021474 | 220 |
| 220085_at | HELLS | helicase lymphoid-specific | NM_018063 | 223 |
| 212520_s_at | SMARCA4 | SWI/SNF related matrix associated actin dependent regulator of chromatin subfamily a member 4 | AI684141 | 226 |
| 202940_at | WNK1 | KIAA0344 gene | NM_014823 | 233 |
| 222366_at | | null | W86781 | 238 |
| 210426_x_at | RORA | RAR-related orphan receptor A | U04897 | 240 |
| 215179_x_at | PGF | Placenta growth factor 2 (PlGF-2) | AK023843 | 244 |
| 221986_s_at | KLHL24 | kelch-like 24 (*Drosophila*) | AW006750 | 245 |
| 207057_at | SLC16A7 | solute carrier family 16 member 7 (monocarboxylic acid transporter 2) | NM_004731 | 247 |
| 203321_s_at | ADNP2 | ADNP homeobox 2 | AK022688 | 250 |
| 204021_s_at | PURA | purine-rich element binding protein A | NM_005859 | 254 |
| 220901_at | GPR157 | G protein-coupled receptor 157 | NM_024980 | 255 |
| 218930_s_at | TMEM106B | transmembrane protein 106B | NM_018374 | 258 |
| 207730_x_at | | null | NM_017932 | 261 |
| 211316_x_at | CFLAR | CASP8 and FADD-like apoptosis regulator | AF009616 | 262 |
| 208610_s_at | SRRM2 | serine/arginine repetitive matrix 2 | AI655799 | 264 |
| 219024_at | PLEKHA1 | pleckstrin homology domain containing family A (phosphoinositide binding specific) member 1 | NM_021622 | 271 |
| 212079_s_at | MLL | myeloid/lymphoid or mixed-lineage leukemia (trithorax homolog *Drosophila*) | AA715041 | 273 |
| 210613_s_at | SYNGR1 | synaptogyrin 1 | BC000731 | 280 |
| 219235_s_at | PHACTR4 | phosphatase and actin regulator 4 | NM_023923 | 284 |
| 220688_s_at | MRTO4 | mRNA turnover 4 homolog (*S. cerevisiae*) | NM_016183 | 290 |
| 212106_at | FAF2 | Fas associated factor family member 2 | BF116183 | 293 |
| 201606_s_at | PWP1 | PWP1 homolog (*S. cerevisiae*) | BE796924 | 294 |
| 211992_at | WNK1 | WNK lysine deficient protein kinase 1 | AI445745 | 296 |
| 208003_s_at | NFAT5 | nuclear factor of activated T-cells 5 tonicity-responsive | NM_006599 | 297 |
| 220572_at | DKFZp547G183 | hypothetical LOC55525 | NM_018705 | 303 |
| 211921_x_at | PTMA | prothymosin alpha | AF348514 | 304 |
| 209065_at | UQCRB | ubiquinol-cytochrome c reductase binding protein | BC005230 | 305 |
| 213998_s_at | DDX17 | DEAD (Asp-Glu-Ala-Asp) box polypeptide 17 | AW188131 | 311 |
| 213298_at | NFIC | nuclear factor I/C (CCAAT-binding transcription factor) | X12492 | 312 |
| 209030_s_at | CADM1 | cell adhesion molecule 1 | NM_014333 | 315 |
| 214305_s_at | SF3B1 | splicing factor 3b subunit 1 155kDa | AW003030 | 317 |
| 219910_at | FICD | FIC domain containing | NM_007076 | 322 |
| 201631_s_at | IER3 | immediate early response 3 | NM_003897 | 323 |
| 208120_x_at | FKSG49 | FKSG49 | NM_031221 | 327 |
| 204180_s_at | ZBTB43 | zinc finger and BTB domain containing 43 | AI745225 | 330 |
| 210057_at | SMG1 | SMG1 homolog phosphatidylinositol 3-kinase-related kinase (*C. elegans*) | U32581 | 335 |
| 219717_at | C4orf30 | chromosome 4 open reading frame 30 | NM_017741 | 336 |
| 203181_x_at | SRPK2 | SFRS protein kinase 2 | AW149364 | 337 |
| 216175_at | | null | AK025276 | 341 |
| 202669_s_at | EFNB2 | ephrin-B2 | U16797 | 344 |
| 220720_x_at | FAM128B | family with sequence similarity 128 member B | NM_025029 | 350 |
| 212807_s_at | SORT1 | sortilin 1 | BF447105 | 356 |
| 201918_at | SLC25A36 | solute carrier family 25 member 36 | AI927944 | 368 |
| 204290_s_at | ALDH6A1 | aldehyde dehydrogenase 6 family member A1 | NM_005589 | 369 |
| 200637_s_at | PTPRF | protein tyrosine phosphatase receptor type F | AI762627 | 371 |
| 33646_g_at | GM2A | GM2 ganglioside activator | X61094 | 381 |
| 220796_x_at | SLC35E1 | solute carrier family 35 member E1 | NM_024881 | 386 |
| 212808_at | NFATC2IP | nuclear factor of activated T-cells cytoplasmic calcineurin-dependent 2 interacting protein | AI884627 | 389 |
| 219633_at | TTPAL | tocopherol (alpha) transfer protein-like | NM_024331 | 395 |
| 215628_x_at | | null | AL049285 | 399 |
| 221006_s_at | SNX27 | sorting nexin family member 27 | NM_030918 | 400 |
| 214972_at | MGEA5 | Meningioma expressed antigen 5 (hyaluronidase) mRNA (cDNA clone MGC:48750 IMAGE:5558183) | AU144791 | 403 |
| 209203_s_at | BICD2 | bicaudal D homolog 2 (*Drosophila*) | BC002327 | 405 |
| 217620_s_at | PIK3CB | phosphoinositide-3-kinase catalytic beta polypeptide | AA805318 | 407 |
| 200616_s_at | MLEC | malectin | BC000371 | 411 |
| 215206_at | | null | AK025143 | 414 |
| 212629_s_at | PKN2 | protein kinase N2 | AI633689 | 417 |
| 214374_s_at | PPFIBP1 | PTPRF interacting protein binding protein 1 (liprin beta 1) | AI962377 | 418 |

TABLE J-continued

| Probe set ID | Gene Symbol | Gene Name | Representative Public ID | Log t-testRank |
|---|---|---|---|---|
| 202867_s_at | DNAJB12 | DnaJ (Hsp40) homolog subfamily B member 12 | NM_017626 | 423 |
| 210407_at | PPM1A | protein phosphatase 1A (formerly 2C) magnesium-dependent alpha isoform | AF070670 | 427 |
| 201846_s_at | RYBP | RING1 and YY1 binding protein | NM_012234 | 428 |
| 204131_s_at | FOXO3 | forkhead box O3 | N25732 | 429 |
| 213748_at | TRIM66 | tripartite motif-containing 66 | AW271713 | 431 |
| 210130_s_at | TM7SF2 | transmembrane 7 superfamily member 2 | AF096304 | 436 |
| 204863_s_at | IL6ST | interleukin 6 signal transducer (gp130 oncostatin M receptor) | BE856546 | 440 |
| 201879_at | ARIH1 | ariadne homolog ubiquitin-conjugating enzyme E2 binding protein 1 (Drosophila) | AI694332 | 442 |
| 209225_x_at | TNPO1 | transportin 1 | AI653355 | 446 |
| 209750_at | NR1D2 | nuclear receptor subfamily 1 group D member 2 | N32859 | 447 |
| 205370_x_at | DBT | dihydrolipoamide branched chain transacylase E2 | NM_001918 | 449 |
| 209024_s_at | SYNCRIP | synaptotagmin binding cytoplasmic RNA interacting protein | AI472757 | 451 |
| 201548_s_at | JARID1B | jumonji AT rich interactive domain 1B | W02593 | 452 |
| 216315_x_at | LOC100133558 | similar to hCG1642170 | AL121873 | 454 |
| 210701_at | CFDP1 | craniofacial development protein 1 | D85939 | 462 |
| 202844_s_at | RALBP1 | ralA binding protein 1 | AW025261 | 466 |
| 208930_s_at | ILF3 | interleukin enhancer binding factor 3 90kDa | BG032366 | 467 |
| 212840_at | UBXN7 | UBX domain protein 7 | BG339560 | 473 |
| 220113_x_at | POLR1B | polymerase (RNA) I polypeptide B 128kDa | NM_019014 | 477 |
| 207993_s_at | CHP | calcium binding protein P22 | NM_007236 | 484 |
| 201085_s_at | SON | SON DNA binding protein | AA664291 | 489 |
| 200727_s_at | ACTR2 | ARP2 actin-related protein 2 homolog (yeast) | AA699583 | 498 |
| 209508_x_at | CFLAR | CASP8 and FADD-like apoptosis regulator | AF005774 | 502 |
| 214843_s_at | USP33 | ubiquitin specific peptidase 33 | AK022864 | 503 |
| 201183_s_at | CHD4 | chromodomain helicase DNA binding protein 4 | AI613273 | 504 |
| 221985_at | KLHL24 | kelch-like 24 (Drosophila) | AW006750 | 509 |
| 217370_x_at | FUS | fusion (involved in t(12;16) in malignant liposarcoma) | S75762 | 511 |
| 219428_s_at | PXMP4 | peroxisomal membrane protein 4 24kDa | BF057649 | 522 |
| 208485_x_at | CFLAR | CASP8 and FADD-like apoptosis regulator | NM_003879 | 523 |
| 203515_s_at | PMVK | phosphomevalonate kinase | NM_006556 | 532 |
| 208549_x_at | PTMAP7 | prothymosin alpha pseudogene 7 | NM_016171 | 535 |
| 205809_s_at | WASL | Wiskott-Aldrich syndrome-like | BE504979 | 543 |
| 217152_at | | null | AK024136 | 551 |
| 214001_x_at | RPS10 | Ribosomal protein S10 | AW302047 | 555 |
| 202035_s_at | SFRP1 | secreted frizzled-related protein 1 | AI332407 | 556 |
| 202082_s_at | SEC14L1 | SEC14-like 1 (S. cerevisiae) | AV748469 | 565 |
| 219723_x_at | AGPAT3 | 1-acylglycerol-3-phosphate O-acyltransferase 3 | NM_020132 | 569 |
| 201072_s_at | SMARCC1 | SWI/SNF related matrix associated actin dependent regulator of chromatin subfamily c member 1 | AW152160 | 570 |
| 203176_s_at | TFAM | transcription factor A mitochondrial | BE552470 | 575 |
| 217550_at | ATF6 | ATF family member ATF6 (ATF6) | AA576497 | 576 |
| 204358_s_at | FLRT2 | fibronectin leucine rich transmembrane protein 2 | AF169676 | 577 |
| 204074_s_at | KIAA0562 | KIAA0562 | AI936976 | 578 |
| 201035_s_at | HADH | hydroxyacyl-Coenzyme A dehydrogenase | BC000306 | 579 |
| 210679_x_at | | null | BC002629 | 580 |
| 201683_s_at | TOX4 | TOX high mobility group box family member 4 | BE783632 | 587 |
| 222284_at | | null | AI734111 | 591 |
| 221765_at | UGCG | UDP-glucose ceramide glucosyltransferase | AI378044 | 596 |
| 210251_s_at | RUFY3 | RUN and FYVE domain containing 3 | AF112221 | 600 |
| 218150_at | ARL5A | ADP-ribosylation factor-like 5A | NM_012097 | 604 |
| 201294_s_at | WSB1 | WD repeat and SOCS box-containing 1 | N24643 | 609 |
| 35436_at | GOLGA2 | golgi autoantigen golgin subfamily a 2 | L06147 | 610 |
| 201996_s_at | SPEN | spen homolog transcriptional regulator (Drosophila) | AL524033 | 612 |
| 210734_x_at | MAX | MYC associated factor X | M64240 | 615 |
| 203542_s_at | KLF9 | Kruppel-like factor 9 | AI690205 | 621 |
| 214670_at | ZKSCAN1 | zinc finger with KRAB and SCAN domains 1 | AA653300 | 626 |
| 208699_x_at | TKT | transketolase | BF696840 | 627 |
| 217703_x_at | | null | AA401963 | 628 |
| 222214_at | | null | AK024988 | 630 |
| 212007_at | UBXN4 | UBX domain protein 4 | AI927512 | 631 |
| 209890_at | TSPAN5 | tetraspanin 5 | AF065389 | 634 |
| 208200_at | IL1A | interleukin 1 alpha | NM_000575 | 637 |
| 213579_at | EP300 | E1A binding protein p300 | AI459462 | 641 |
| 213650_at | GOLGA8A | golgi autoantigen golgin subfamily a 8A | AW006438 | 644 |
| 203975_s_at | CHAF1A | chromatin assembly factor 1 subunit A (p150) | BF000239 | 647 |
| 39313_at | WNK1 | KIAA0344 gene | AB002342 | 650 |
| 215069_at | NMT2 | N-myristoyltransferase 2 | AK025065 | 652 |
| 219392_x_at | PRR11 | proline rich 11 | NM_018304 | 653 |
| 213506_at | F2RL1 | coagulation factor II (thrombin) receptor-like 1 | BE965369 | 658 |
| 211000_s_at | IL6ST | interleukin 6 signal transducer (gp130 oncostatin M receptor) | AB015706 | 660 |
| 222036_s_at | MCM4 | minichromosome maintenance complex component 4 | AI859865 | 662 |
| 218155_x_at | TSR1 | TSR1 20S rRNA accumulation homolog (S. cerevisiae) | AK026565 | 670 |
| 200635_s_at | PTPRF | protein tyrosine phosphatase receptor type F | AU145351 | 674 |
| 210686_x_at | SLC25A16 | solute carrier family 25 (mitochondrial carrier; Graves disease autoantigen) member 16 | BC001407 | 678 |
| 66053_at | HNRNPUL2 | heterogeneous nuclear ribonucleoprotein U-like 2 | AI738452 | 693 |

TABLE J-continued

| Probe set ID | Gene Symbol | Gene Name | Representative Public ID | Log t-testRank |
|---|---|---|---|---|
| 213299_at | ZBTB7A | zinc finger and BTB domain containing 7A | AW027070 | 696 |
| 208336_s_at | GPSN2 | glycoprotein synaptic 2 | NM_004868 | 698 |
| 218521_s_at | UBE2W | ubiquitin-conjugating enzyme E2W (putative) | NM_018299 | 700 |
| 1053_at | RFC2 | replication factor C (activator 1) 2 40kDa | M87338 | 702 |
| 211317_s_at | CFLAR | CASP8 and FADD-like apoptosis regulator | AF041461 | 705 |
| 201205_at | | null | AF006751 | 706 |
| 222180_at | | null | AU147889 | 707 |
| 221419_s_at | | null | NM_013307 | 709 |
| 217813_s_at | SPIN1 | spindlin 1 | NM_006717 | 710 |

What is claimed is:

1. A system for identifying connections between a cosmetic agent and at least one gene associated with a skin aging condition, comprising:
  a. at least one computer readable medium having stored thereon a plurality of instances and a skin aging gene expression signature, wherein each instance comprises an ordered list of identifiers representing a plurality of up-regulated and a plurality of down regulated genes differentially expressed in response to contact between the cosmetic agent and a human fibroblast cell or a human keratinocyte cell, the skin aging gene expression signature comprises one or more lists comprising a plurality of identifiers representing a plurality of up-regulated genes and a plurality of down-regulated genes associated with a skin aging condition, and from about 80% to about 100% of the plurality of identifiers associated with the skin aging gene expression signature represent a gene set forth in any of Tables A to D; and
  b. a first computing device comprising computer-readable instructions that cause the computing device to:
    i. access the plurality of instances and the skin aging gene expression signature stored on the computer readable medium;
    ii. comparing each of the instances to the skin aging gene expression signature, wherein the comparison comprises comparing each identifier in the gene expression signature list(s) with the position of the same identifier in the instance list; and
    iii. assigning a connectivity score to each of the plurality of instances based on the comparison in (ii).

2. The system of claim 1, further comprising a microarray having a plurality of probes for hybridizing to cDNA reverse transcribed from mRNA extracted from the fibroblast cell or the keratinocyte cell.

3. The system of claim 2, further comprising a microarray scanner for scanning the microarray and translating the plurality of hybridized probes to gene expression data.

4. The system of claim 3, further comprising a second computing device for transmitting the gene expression data from the microarray scanner to the first computing device.

5. The system of claim 2, further comprising a plurality of cosmetic agents for application to the fibroblast cell or the keratinocyte cell.

6. The system of claim 5, wherein the plurality of cosmetic agents comprise a botanical derived from a root, stem, bark, leaf, seed or fruit of a plant.

7. The system of claim 1, wherein the plurality of identifiers are selected from the group consisting of a microarray probe set ID, a human gene name, a human gene symbol and combinations thereof.

8. The system of claim 7, wherein the plurality of identifiers comprises from about 50 to about 600 identifiers.

9. The system of claim 8, wherein the plurality of identifiers associated with the at least one gene expression signature are selected from the genes of Tables C and D.

10. The system of claim 8, wherein the plurality of identifiers associated with the at least one gene expression signature are selected from the genes of Tables A and B.

11. The system of claim 1, wherein each of the plurality of instances further comprises metadata associated with the fibroblast cell or the keratinocyte cell and the cosmetic agent.

12. The system of claim 1, wherein the plurality of instances comprises between about 50 and about 50,000 instances.

13. The system of claim 12, wherein the plurality of instances comprises between about 1,000 and about 20,000 instances.

14. The system of claim 1, further comprising a full thickness skin biopsy from skin having a skin aging condition associated with the at least one skin aging gene expression signature.

15. The system of claim 14, wherein the full thickness skin biopsy is from skin that is sun protected.

16. The system of claim 15, wherein where the full thickness skin biopsy is from an individual having an age from about 45 years to about 80 years.

17. The system of claim 15, further comprising a second full thickness skin biopsy from an individual having an age from about 18 years to about 25 years.

* * * * *